(12) United States Patent
Paterson et al.

(10) Patent No.: US 7,855,064 B2
(45) Date of Patent: Dec. 21, 2010

(54) ANTIBIOTIC RESISTANCE FREE VACCINES AND METHODS FOR CONSTRUCTING AND USING SAME

(75) Inventors: Yvonne Paterson, Philadelphia, PA (US); Thorsten Verch, North Wales, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 168 days.

(21) Appl. No.: 11/785,249

(22) Filed: Apr. 16, 2007

(65) Prior Publication Data

US 2008/0131456 A1 Jun. 5, 2008

Related U.S. Application Data

(63) Continuation-in-part of application No. 11/203,415, filed on Aug. 15, 2005.

(60) Provisional application No. 60/601,492, filed on Aug. 13, 2004.

(51) Int. Cl.
*A61K 39/02* (2006.01)
(52) U.S. Cl. .................. 435/252.3; 424/200.1
(58) Field of Classification Search .................. None
See application file for complete search history.

(56) References Cited

U.S. PATENT DOCUMENTS

| 4,458,066 | A |  | 7/1984 | Caruthers et al. |  |
| 6,099,848 | A | * | 8/2000 | Frankel et al. | ............ 424/246.1 |
| 6,767,542 | B2 |  | 7/2004 | Paterson et al. |  |
| 2005/0118184 | A1 |  | 6/2005 | Paterson et al. |  |

FOREIGN PATENT DOCUMENTS

| WO | WO 99/25376 | 5/1999 |
| WO | WO 01/72329 | 10/2001 |
| WO | WO 01/72329 A1 * | 10/2001 |

OTHER PUBLICATIONS

Lauer et al. (J. Bacteriol., 184:4177-4186, 2002).*
Peters et al. (Vaccine, 21:1187-1194, 2003).*
Bruhn et al., "Listeria as a vaccine vector", Microbes and Infection 9, 2007, 1226-1235.
Peters et al., "Enhancing the immunogenicity of bioengineered Listeria monocytogenes by passaging through live animal hosts." Vaccine, 21: 1187-1194, 2003.
Alexander et al., 1993, "Characterization of an aromatic amino acid-dependent Listeria monocytogenes mutant: attenuation, persistence, and ability to produce protective immunity in mice", Infection and Immunity 61:2245-2248.
Abachin et al., 2002, "Formation of D-alanyl-lipoteichoic acid is required for adhesion and virulence of Listeria monocytogenes", Mol. Microbiol. 43:1-14.
Brundage et al., 1993, "Expression and phosphorylation of the Listeria monocytogenes ActA protein in mammalian cells", Proc. Natl. Acad. Sci. USA 90:11890-11894.
Bron et al., 2002, "Use of the alr Gene as a Food-Grade Selection Marker in Lactic Acid Bacteria", Applied And Environmental Microbiology, 68(11):5663-5670.
Brown et al., 1979, "Chemical Synthesis and Cloning of a Tyrosine tRNA Gene", Meth Enzymol. 68:109-151.
Beaucage et al., 1981, "Deoxynucleoside Phosphoramidites—A New Class of Key Intermediates for Deoxypoylnucleotide Synthesis", Tetra. Lett. 22:1859-1862.
Camilli et al., 1992, "Dual Roles of plcA in Listeria monocytogenes Pathogenesis", Mol. Microbiol. 8:143-157.
Camilli et al., 1991; "Listeria monocytogenes mutants lacking phosphatidylinositol-specific phospholipase C are avirulent", J. Exp. Med., 173:751-754.
Cenatiempo, 1986, "Prokaryotic Gene Expression In Vitro. Transcription—Translation Coupled Systems", Biochimie 68:505-516.
Dermer, 1994, "Another Anniversary for the War on Cancer", Bio/Technology, vol. 12, p. 320.
De Boer et al., 1989, "A division inhibitor and a topological specificity factor coded for by the minicell locus determine proper placement of the division septum in E.coil". Cell 55:641-649.
Frankel et al., 1995, "Induction of cell-mediated immune responses to human immunodeficiency virus type 1 Gag protein by using Listeria monocytogenes as a live vaccine vector", J. immunol. 155:4775-4782.
Freshbey, 1983, "Culture of Animal Cells, A Manual of Basic Technique", Alan R, Liss Inc, pp. 3-4.
Glenting et al , 2002, "A Plasmid Selection System in Lactococcus Lactis and Its Use for Gene Expression in L. lactis and Human Kidney Fibroblasts", Applied and Environmental Microbiology, 68:5051-5056.
Gunn et al. 2001, "Two Listeria monocytogenes Vaccine Vectors That Express Different Molecular Forms of Human Papilloma Virus-16 (HPV-16) E7 Induce Qualitatively Different T Cell Immunity That Correlates with Their Ability to Induce Regression of Established Tumors Immortalized by HPV-16", J Immunol 167:6471-6479.
Gilman et al., 1984, "Isolation of sigma-28-specific promoters from Bacillus subtilis DNA", Gene 32:11-20.
Glick, 1987 "Factors affecting the expression of foreign proteins in Escherichia coli", J. Ind Microbiol. 1:277-282.
Gottesman, 1984, "Bacterial regulation: global regulatory networks", Ann. Rev. Genet 18:415-442.
Gura, 1997, "Systems for Identifying New Drugs Are Often Faulty", Science 278:1041-1042.
Greenspan et al., 1999, "Defining epitopes It's not easy as it seems", Nature Biotechnology 7:936-937.
Harris et al , 1986, "Molecular basis for heterogeneity of the human p53 protein", Mol. Cell. Biol. 6:4650-4656.

(Continued)

*Primary Examiner*—N. M Minnifield
*Assistant Examiner*—Brian J Gangle
(74) *Attorney, Agent, or Firm*—Mark S. Cohen; Pearl Cohen Zedek Latzer, LLP

(57) ABSTRACT

The present invention provides *Listeria* strains that express a heterologous antigen and a metabolic enzyme, and methods of generating same.

15 Claims, 15 Drawing Sheets

OTHER PUBLICATIONS

Ikonomidis et al., 1994, "Delivery of a viral antigen to the class I processing and presentation pathway by *Listeria monocytogenes*", J. Exp. Med. 180 2209-2218.

International Search Report of Application No. PCT/US08/04861 issued Sep. 29, 2008.

International Search Report of Application No. PCT/US05/28896 issued Oct. 26, 2006.

International Search Report of Application No. PCT/US05/28895 issued Jul. 15, 2006.

Kohler, et al., 1991, "Expression of the iap gene coding for protein p60 of *Listeria monocytogenes* is controlled on the post-transcriptional level", J Bacteriol 173: 4668-4674.

Leitner et al., 2000, "DNA and RNA-based vaccines: principles, progress and prospects", Vaccine 18:765-777.

Lauer et al., 2002, "Construction, Characterization, and Use of Two *Listeria monocytogenes* Site-Specific Phage Integration Vectors", J. Bacteriol. 184:4177-4186.

Mata et al., 2001, "Evaluation of a recombinant *Listeria monocytogenes* expressing an HIV protein that protects mice against viral challenge", Vaccine 19:1435-1445.

Miller et al., 1995, "Targeted vectors for gene therapy", FASEB J., 9:190-199.

Narang et al., 1979, "Improved Phosphotriester Method for the Synthesis of Gene Fragments", Meth. Enzymol., 68:90-99.

Pucci et al., 1995, "*Staphylococcus haemolyticus* contains two D-glutamic acid biosynthetic activities, a glutamate racemase and a D-amino acid transaminase", J Bacteriol. 177:336-342.

Pilgrim et al., 2003, "Bactofection of mammalian cells by *Listeria monocytogenes*: improvement and mechanism of DNA delivery", Gene Ther., 10(24):2036-45.

Restifo et al., 2000, "The promise of nucleic acid vaccines", Gene Therapy, 7:89-92.

Sizemore et al., 1995, "Attenuated *Shigella* as a DNA Delivery Vehicles for DNA-Mediated Immunization", Science 270:299-302.

Strych et al., 2002, "Mutant analysis shows that alanine racemases from *Pseudomonas aeruginosa* and *Escherichia coli* are dimeric", J. Bacteriol. 184:4321-4325.

Thompson et al., 1998, "Pathogenicity and immunogenicity of a *Listeria monocytogenes* strain that requires D-alanine for growth", Infec Immun 66: 3552-3561.

Tauch et al., 2002, "The alanine racemase gene *air* is an alternative to antibiotic resistance genes in cloning systems for industrial *Corynebacterium glutamicum* strains", J. Biotechnol 99:79-91.

Ulmanen et al.. 1985, "Transcription and translation of foreign genes in *Bacillus subtilis* by the aid of a secretion vector", J. Bacteriol., 162:176-182.

Verch et al., Nov. 2004. "*Listeria monocytogenes*-Based Antibiotic Resistance Gene-Free Antigen Delivery System Applicable to Other Bacterial Vectors and DNA Vaccines", Infection and Immunity, pp. 6418-6425.

Wirth et al., 1986, "Highly efficient protoplast transformation system for *Streptococcus faecalis* and a new *Escherichia coli*-S faecalis shuttle vector", J. Bacteriol. 165(3):831-6.

Ward et al , 1986, "Construction and Characterisation of a Series of Multi-copy Promoter-probe Plasmid Vectors for Streptomyces Using the Aminoglycoside Phosphotransferase Gene From Tn5 as Indicator", Mol. Gen. Genet. 203:468-478.

Yaghmai et al., 2002 "Optimized regulation of gene expression using artifical transcription factors", Mol. Therapy, 5:685-694.

http://www.biology-text.com/definition.php?word=Pest+sequence. accessed Jan. 22, 2007.

Rechsteiner et al., "PEST sequences and regulation by proteolysis", Trends Biochem Sci. Jul. 1996;21(7):267-71.

* cited by examiner

ANTIBIOTIC RESISTANCE FREE VACCINES AND METHODS FOR CONSTRUCTING AND USING SAME

CROSS-REFERENCE TO RELATED APPLICATIONS

This application is a Continuation-in-Part of U.S. application Ser. No. 11/203,415, filed Aug. 15, 2005, which claims priority of U.S. Provisional Application Ser. No. 60/601,492, filed Aug. 13, 2004. This application is hereby incorporated in its entirety by reference herein.

STATEMENT REGARDING FEDERALLY SPONSORED RESEARCH OR DEVELOPMENT

This research was supported in whole or in part by U.S. Government funds (RAID NSC 715814 and CA69632). The U.S. Government has certain rights in the invention.

FIELD OF INVENTION

The present invention provides *Listeria* strains that express a heterologous antigen and a metabolic enzyme, and methods of generating same.

BACKGROUND OF THE INVENTION

Vaccines represent the most beneficial and cost effective public health measure currently known. However, as the understanding of neoplasias and infectious diseases grows, it has become apparent that traditional vaccine strategies may not be completely effective. Traditional vaccines have employed killed or attenuated organisms or antigen subunits in order to elicit immunity in an animal. A limit with these approaches, especially with killed or subunit vaccines, is that the immune response is primarily humoral in nature, and therefore not effective in combating intracellular organism or tumors that require cell mediated immunity for their destruction. Similarly, attenuated or inactivated bacteria often only induce immunization for a short period of time and immunity is limited to a humoral response. Further, traditional attenuated or inactivated bacterial vaccines do not elicit the cytotoxic T-lymphocyte (CTL) immune response necessary for the lysis of tumor cells and cells infected with intracellular pathogens.

Viral vaccines are often used to induce a CTL response in a vaccine. Viral vaccines are usually pathogenic viruses attenuated by serial passage in cell culture or viruses killed through heat or chemical inactivation. Killed viruses are incapable of infecting cells, and thus, like subunit vaccines, primarily elicit a humoral immune response. Attenuated viruses are capable of infecting cells, and can induce a CTL response in an individual. However, attenuated virus vaccines are not without drawbacks. First, attenuating a virus is often a process of trial and error. Second, there is a serious safety issue in using attenuated viruses, especially in children, the elderly, and the immuno-compromised. A solution to the problems of traditional bacterial and viral vaccines exists with bacterial vaccine vectors such as *Listeria monocytogenes* (LM). LM is a beta hemolytic gram positive facultative intracellular microbe.

Three methods are currently used to express a heterologous antigen in *Listeria monocytogenes*, and include plasmid-based expression systems and chromosome expression systems. One chromosomal based method is described in Frankel et al. (1995, J. Immunol. 155:4775-4782) and Mata et al. (2001, Vaccine 19:1435-1445). Briefly, a gene encoding the antigen of interest is placed, along with a suitable promoter and signal sequence, between two regions of DNA homologous to a region of the *Listeria* chromosome. This homologous recombination allows specific integration of the antigen in the *Listeria* chromosome. The cassette comprising the antigen and the homologous DNA is ligated into a temperature sensitive plasmid incapable of replication at temperatures above 40° C. The plasmid further comprises drug resistance markers for selection and plasmid maintenance purposes. The manipulation and replication of this plasmid usually takes place in *E. coli*, because of its rapid replication and ease of transformation compared to *Listeria*. Because *Listeria* is a gram positive organism and *E. coli* is a gram negative organism, the drug resistance genes can be specific to each category of organism, or there may be two copies of the same drug resistance gene effective in both types of organism, but under the control of separate gram positive and gram negative promoters. After assembly, the plasmid is transformed into LM by direct conjugation with the *E. coli* comprising the plasmid, or by lysis and isolation of the plasmid from the *E. coli*, followed by electroporation of competent LM.

In order to integrate the plasmid into the desired region of the *Listeria* chromosome, the two-step allelic exchange method of Camilli et al. (1992, Mol. Microbiol. 8:143-157) is followed. Briefly, the *Listeria* is passaged at greater than 40° C. to prevent plasmid replication. Integration of the plasmid into the *Listeria* chromosome is selected by growth at 40° C. in the presence of a selecting drug, e.g. chloramphenicol. After selection of transformants, bacteria are passaged at 30° C. and selected for drug sensitivity to screen for *Listeria* in which excision of extraneous vector sequences has occurred. The disadvantage of this method is that the double allelic exchange method is time consuming and requires the selection of many clones in order to arrive at a suitable vaccine strain. A second chromosomal method of producing *Listeria* strains comprising a heterologous antigen is described by Lauer et al. (2002, J. Bacteriol. 184:4177-4186). This method does not require allelic exchange, but instead requires two phage-based integration vectors. This method utilizes one or two drug resistance genes, resulting in a *Listeria* organism comprising resistance to one or more drugs. The disadvantage of the methods of Lauer et al is the presence of drug resistance genes, which are not considered safe because of concern over the spread of antibiotic resistance to microorganisms previously susceptible to antibiotic therapy. Therefore, the presence of antibiotic resistance genes in a vaccine vector is considered a liability from a safety perspective.

A third method of expressing foreign antigen in *Listeria* is to express the antigen episomally from a plasmid. This method is described in Ikonomidis et al. (1994 J. Exp. Med. 180: 2209-2218) and Gunn et al. (2001, J Immunol 167: 6471-6479). This method has the advantage that the gene does not have to be integrated into the chromosome and can be expressed in multiple copies, which may enhance immunogenicity. However, in order to select for plasmid transformants and ensure the retention of the plasmid during propagation in vitro it is necessary to include two drug resistance genes on the plasmid, one for the construction of the plasmid in *E. coli* and one for the propagation of the transformed *Listeria monocytogenes*.

Thus, given the demonstrated uses of *Listeria* as a vaccine vector, methods for constructing *Listeria* vaccine vectors without antibiotic resistance, yet capable of eliciting a strong immune response, are needed in the field.

BRIEF SUMMARY OF THE INVENTION

The present invention provides *Listeria* strains that express a heterologous antigen and a metabolic enzyme, and methods of generating same.

In one embodiment, the present invention provides a recombinant bacterial strain, comprising an integrated nucleic acid molecule, wherein the nucleic acid molecule comprises a first open reading frame encoding a polypeptide, wherein the polypeptide comprises a protein antigen, and the nucleic acid molecule further comprises a second open reading frame encoding a metabolic enzyme. In another embodiment, the integrated nucleic acid molecule is integrated into the chromosome. In another embodiment, the recombinant bacterial strain is a recombinant *Listeria* strain. In another embodiment, the strain is a *Listeria* vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of inducing an immune response against a protein antigen of interest in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, and the nucleic acid molecule further comprises a second open reading frame encoding a metabolic enzyme, thereby inducing an immune response against a protein antigen of interest in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of inducing an immune response against a tumor of interest in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, whereby said tumor expresses said antigen, and the nucleic acid molecule further comprises a second open reading frame encoding a metabolic enzyme, thereby inducing an immune response against a protein antigen of interest in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of treating a cancer in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the cancer expresses the protein antigen of interest, and the nucleic acid molecule further comprises a second open reading frame encoding a metabolic enzyme, thereby treating a cancer in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of reducing an incidence of a cancer in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the cancer expresses the protein antigen of interest, and the nucleic acid molecule further comprises a second open reading frame encoding a metabolic enzyme, thereby reducing an incidence of a cancer in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of treating an infectious disease in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the infectious disease organism expresses the protein antigen of interest, and the nucleic acid molecule further comprises a second open reading frame encoding a metabolic enzyme, thereby treating an infectious disease in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of reducing an incidence of an infectious disease in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the infectious disease organism expresses the protein antigen of interest, and the nucleic acid molecule further comprises a second open reading frame encoding a metabolic enzyme, thereby reducing an incidence of an infectious disease in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

DETAILED DESCRIPTION OF THE INVENTION

Figure 1A:
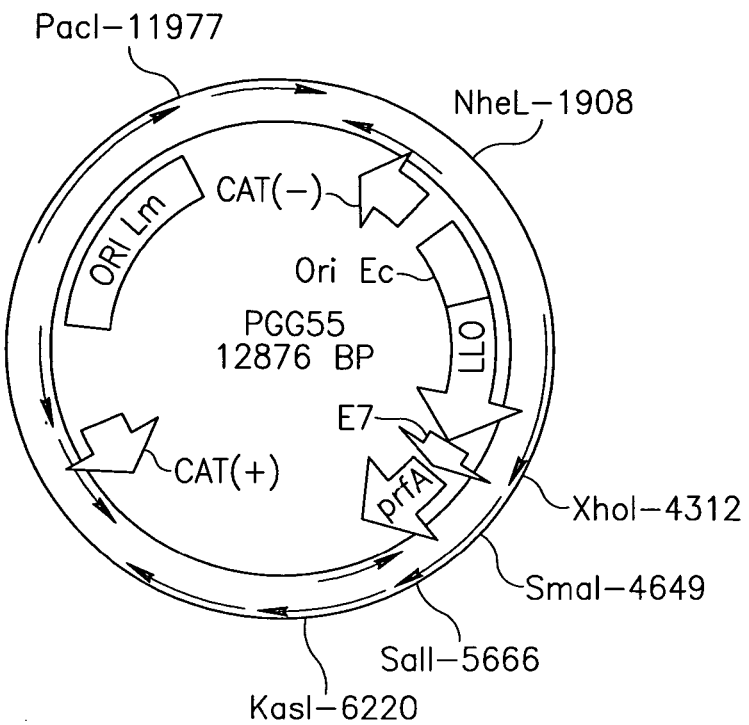
FIG. 1 is a schematic map of *E. coli-Listeria* shuttle plasmids pGG55 (above) and pTV3 (below). CAT(−): *E. coli* chloramphenicol transferase; CAT(+): *Listeria* chloramphenicol transferase; Ori Lm: replication origin for *Listeria*; Ori Ec: p15 origin of replication for *E. coli*; prfA: *Listeria* pathogenicity regulating factor A; LLO: C-terminally truncated listeriolysin O, including its promoter; E7: HPV E7; p60-dal; expression cassette of p60 promoter and *Listeria* dal gene. Selected restriction sites are also depicted.

The present invention provides *Listeria* strains that express a heterologous antigen and a metabolic enzyme, and methods of generating same.

In one embodiment, the present invention provides a recombinant bacterial strain, comprising an integrated nucleic acid molecule, wherein the nucleic acid molecule comprises a first open reading frame encoding a polypeptide, wherein the polypeptide comprises a protein antigen, and the nucleic acid molecule further comprises a second open reading frame encoding a metabolic enzyme. In another embodiment, the integrated nucleic acid molecule is integrated into the chromosome. In another embodiment, the recombinant bacterial strain is a recombinant *Listeria* strain. In another embodiment, the strain is a *Listeria* vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of inducing an immune response against a protein antigen of interest in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, and the nucleic acid molecule further comprises a second open reading frame encoding a metabolic enzyme, thereby inducing an immune response against a protein antigen of interest in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of inducing an immune response against a tumor of interest in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, whereby said tumor expresses said antigen, and the nucleic acid molecule further comprises a second open reading frame encoding a metabolic enzyme, thereby inducing an immune response against a protein antigen of interest in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of treating a cancer in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the cancer expresses the protein antigen of interest, and the nucleic acid molecule further comprises a second open reading frame encoding a metabolic enzyme, thereby treating a cancer in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of reducing an incidence of a cancer in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the cancer expresses the protein antigen of interest, and the nucleic acid molecule further comprises a second open reading frame encoding a metabolic enzyme, thereby reducing an incidence of a cancer in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of treating an infectious disease in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the infectious disease organism expresses the protein antigen of interest, and the nucleic acid molecule further comprises a second open reading frame encoding a metabolic enzyme, thereby treating an infectious disease in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of reducing an incidence of an infectious disease in a subject, comprising the step of administering to the subject a recombinant bacterial strain, comprising an integrated nucleic acid molecule, wherein the nucleic acid molecule comprises a first open reading frame encoding a polypeptide, wherein the polypeptide comprises the protein antigen of interest, the infectious disease organism expresses the protein antigen of interest, and the nucleic acid molecule further comprises a second open reading frame encoding a metabolic enzyme, thereby reducing an incidence of an infectious disease in a subject. In another embodiment, the integrated nucleic acid molecule is integrated into the chromosome. In another embodiment, the recombinant bacterial strain is a recombinant bacterial strain. In another embodiment, the strain is a bacterial vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

"Nucleic acid molecule" refers, in another embodiment, to a plasmid. In another embodiment, the term refers to an integration vector. In another embodiment, the term refers to a plasmid comprising an integration vector. In another embodiment, the integration vector is a site-specific integration vector. In another embodiment, a nucleic acid molecule of methods and compositions of the present invention can be composed of any type of nucleotide known in the art. Each possibility represents a separate embodiment of the present invention. Each possibility represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA may be, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA may be in form of plasmid DNA, viral DNA, linear DNA, or chromosomal DNA or derivatives of these groups. In addition, these forms of DNA and RNA may be single, double, triple, or quadruple stranded. The term also includes, in another embodiment, artificial nucleic acids that may contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

"Stably maintained" refers, in another embodiment, to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro. Each possibility represents a separate embodiment of the present invention.

In another embodiment, the present invention provides a method of engineering an auxotrophic bacterial strain to express a heterologous antigen, the method comprising the step of contacting the auxotrophic bacterial strain with a nucleic acid molecule, the nucleic acid construct comprising a first nucleic acid sequence encoding a polypeptide that comprises the heterologous antigen, and the nucleic acid construct further comprising a second nucleic acid sequence encoding a metabolic enzyme, thereby engineering an auxotrophic bacterial strain to express a heterologous antigen. In another embodiment, the integrated nucleic acid molecule is integrated into the chromosome. In another embodiment, the recombinant bacterial strain is a recombinant *Listeria* strain. In another embodiment, the strain is a *Listeria* vaccine strain. In another embodiment, the metabolic enzyme complements an endogenous metabolic gene that is lacking in the remainder of the chromosome of the recombinant bacterial strain. In another embodiment, the nucleic acid molecule is stably maintained in the recombinant bacterial strain in the absence of an antibiotic selection. Each possibility represents a separate embodiment of the present invention.

In another embodiment, the present invention provides a method of engineering a *Listeria* vaccine strain to express a heterologous antigen, the method comprising contacting an auxotrophic *Listeria* strain with a plasmid, the plasmid comprising a first nucleic acid sequence encoding a polypeptide that comprises the heterologous antigen, and the plasmid further comprising a second nucleic acid sequence encoding a metabolic enzyme, whereby the auxotrophic *Listeria* strain takes up the plasmid, and whereby the metabolic enzyme complements a metabolic deficiency of the auxotrophic *Listeria* strain, thereby engineering a *Listeria* vaccine strain to express a heterologous antigen.

In another embodiment, the present invention provides a method of engineering a *Listeria* vaccine strain to express a heterologous antigen, the method comprising transforming an auxotrophic *Listeria* strain with a plasmid comprising a first nucleic acid encoding the heterologous antigen and a second nucleic acid encoding a metabolic enzyme, whereby the metabolic enzyme complements a metabolic deficiency of the auxotrophic *Listeria* strain, thereby engineering a *Listeria* vaccine strain to express a heterologous antigen.

"Transforming," in one embodiment, is used identically with the term "transfecting," and refers to engineering a bacterial cell to take up a plasmid or other heterologous DNA molecule. In another embodiment, "transforming" refers to engineering a bacterial cell to express a gene of a plasmid or other heterologous DNA molecule. Each possibility represents a separate embodiment of the present invention.

In another embodiment, the plasmid or nucleic acid molecule of methods and compositions of the present invention further comprises a gene encoding a transcription factor. In another embodiment, the transcription factor is lacking in the auxotrophic *Listeria* strain or in the bacteria chromosome of a *Listeria* strain of the present invention. In one embodiment, the transcription factor is prfA (Examples herein). In another embodiment, the transcription factor is any other transcription factor known in the art. Each possibility represents a separate embodiment of the present invention.

In one embodiment, the metabolic gene, transcription factor-encoding gene, etc. is lacking in a chromosome of the bacterial strain. In another embodiment, the metabolic gene, transcription factor, etc. is lacking in all the chromosomes of the bacterial strain. In another embodiment, the metabolic gene, transcription factor, etc. is lacking in the genome of the bacterial strain.

In one embodiment, the gene encoding a transcription factor is mutated in the chromosome. In another embodiment, the gene is deleted from the chromosome. Each possibility represents a separate embodiment of the present invention.

In one embodiment, the transcription factor is mutated in the chromosome. In another embodiment, the transcription factor is deleted from the chromosome. Each possibility represents a separate embodiment of the present invention.

In another embodiment, the integration vector or plasmid of methods and compositions of the present invention does not confer antibiotic resistance to the *Listeria* vaccine strain. In another embodiment, the integration vector or plasmid does not contain an antibiotic resistance gene. Each possibility represents a separate embodiment of the present invention.

In another embodiment, the first nucleic acid sequence of methods and compositions of the present invention is operably linked to a promoter/regulatory sequence. In another embodiment, the second nucleic acid sequence is operably linked to a promoter/regulatory sequence. In another embodiment, each of the nucleic acid sequences is operably linked to a promoter/regulatory sequence. Each possibility represents a separate embodiment of the present invention.

In another embodiment, the promoter/regulatory sequence of the second nucleic acid sequence functions in *E. coli*, thereby enabling stable maintenance of the plasmid or nucleic acid molecule in the *E. coli* strain. In another embodiment, the second nucleic acid sequence is expressed in an *E. coli* strain upon transfecting the *E. coli* strain with a plasmid or nucleic acid molecule of the present invention, thereby enabling stable maintenance thereof in the *E. coli* strain.

Methods for introducing a prophage into LM are well known in the art. In another embodiment, conjugation is utilized. In another embodiment, electroporation is utilized. In another embodiment, any other method known in the art is utilized. Each possibility represents a separate embodiment of the present invention.

In another embodiment, the present invention provides a *Listeria* vaccine strain, comprising a plasmid, wherein the plasmid comprises a first nucleic acid sequence encoding a polypeptide, wherein the polypeptide comprises a protein antigen, and the plasmid further comprises a second nucleic acid sequence encoding a metabolic enzyme, whereby the metabolic enzyme complements an endogenous metabolic gene that is lacking in a chromosome of the *Listeria* vaccine strain, and whereby the plasmid is stably maintained in the *Listeria* vaccine strain in the absence of an antibiotic selection.

In one embodiment, the endogenous metabolic gene is mutated in the chromosome. In another embodiment, the endogenous metabolic gene is deleted from the chromosome. Each possibility represents a separate embodiment of the present invention.

In another embodiment, the present invention provides a method of engineering a *Listeria* vaccine strain to express a heterologous antigen, the method comprising contacting an auxotrophic *Listeria* strain with a nucleic acid construct, the nucleic acid construct comprising a first nucleic acid sequence encoding a polypeptide that comprises the heterologous antigen, and the nucleic acid construct further comprising a second nucleic acid sequence encoding a metabolic enzyme, whereby the nucleic acid construct is incorporated into a genome of the auxotrophic *Listeria* strain, and whereby the metabolic enzyme complements a metabolic deficiency of the auxotrophic *Listeria* strain, thereby engineering a *Listeria* vaccine strain to express a heterologous antigen.

In one embodiment, the nucleic acid construct lacks a *Listeria* replication region. In another embodiment, only *Listeria* that contain a copy of the nucleic acid construct that is integrated into the genome are selected upon growth in LB media. In another embodiment, the nucleic acid construct contains a *Listeria* replication region. Each possibility represents a separate embodiment of the present invention.

In one embodiment, the nucleic acid construct contains an integration site. In one embodiment, the site is a PSA attPP' integration site. In another embodiment, the site is any another integration site known in the art. Each possibility represents a separate embodiment of the present invention.

In another embodiment, the nucleic acid construct contains an integrase gene. In another embodiment, the integrase gene is a PSA integrase gene. In another embodiment, the integrase gene is any other integrase gene known in the art. Each possibility represents a separate embodiment of the present invention.

In one embodiment, the nucleic acid construct is a plasmid. In another embodiment, the nucleic acid construct is a shuttle plasmid. In another embodiment, the nucleic acid construct is an integration vector. In another embodiment, the nucleic acid construct is a site-specific integration vector. In another embodiment, the nucleic acid construct is any other type of nucleic acid construct known in the art. Each possibility represents a separate embodiment of the present invention.

The integration vector of methods and compositions of the present invention is, in another embodiment, a phage vector. In another embodiment, the integration vector is a site-specific integration vector. In another embodiment, the vector further comprises an integrase gene. In another embodiment, the vector further comprises an attPP' site. Each possibility represents a separate embodiment of the present invention.

In another embodiment, the integration vector is a U153 vector. In another embodiment, the integration vector is an A118 vector. In another embodiment, the integration vector is a PSA vector.

In another embodiment, the vector is an A511 vector (e.g. GenBank Accession No: X91069). In another embodiment, the vector is an A006 vector. In another embodiment, the vector is a B545 vector. In another embodiment, the vector is a B053 vector. In another embodiment, the vector is an A020 vector. In another embodiment, the vector is an A500 vector (e.g. GenBank Accession No: X85009). In another embodiment, the vector is a B051 vector. In another embodiment, the vector is a B052 vector. In another embodiment, the vector is a B054 vector. In another embodiment, the vector is a B055 vector. In another embodiment, the vector is a B056 vector. In another embodiment, the vector is a B101 vector. In another embodiment, the vector is a B110 vector. In another embodiment, the vector is a B111 vector. In another embodiment, the vector is an A153 vector. In another embodiment, the vector is a D441 vector. In another embodiment, the vector is an A538 vector. In another embodiment, the vector is a B653 vector. In another embodiment, the vector is an A513 vector. In another embodiment, the vector is an A507 vector. In another embodiment, the vector is an A502 vector. In another embodiment, the vector is an A505 vector. In another embodiment, the vector is an A519 vector. In another embodiment, the vector is a B604 vector. In another embodiment, the vector is a C703 vector. In another embodiment, the vector is a B025 vector. In another embodiment, the vector is an A528 vector. In another embodiment, the vector is a B024 vector. In another embodiment, the vector is a B012 vector. In another embodiment, the vector is a B035 vector. In another embodiment, the vector is a C707 vector.

In another embodiment, the vector is an A005 vector. In another embodiment, the vector is an A620 vector. In another embodiment, the vector is an A640 vector. In another embodiment, the vector is a B021 vector. In another embodiment, the vector is an HSO47 vector. In another embodiment, the vector is an H10G vector. In another embodiment, the vector is an H8/73 vector. In another embodiment, the vector is an H19 vector. In another embodiment, the vector is an H21 vector. In another embodiment, the vector is an H43 vector. In another embodiment, the vector is an H46 vector. In another embodiment, the vector is an H107 vector. In another embodiment, the vector is an H108 vector. In another embodiment, the vector is an H110 vector. In another embodiment, the vector is an H163/84 vector. In another embodiment, the vector is an H312 vector. In another embodiment, the vector is an H340 vector. In another embodiment, the vector is an H387 vector. In another embodiment, the vector is an H391/73 vector. In another embodiment, the vector is an H684/74 vector. In another embodiment, the vector is an H924A vector. In another embodiment, the vector is an fMLUP5 vector. In another embodiment, the vector is a syn (=P35) vector. In another embodiment, the vector is a 00241 vector. In another embodiment, the vector is a 00611 vector. In another embodiment, the vector is a 02971A vector. In another embodiment, the vector is a 02971C vector. In another embodiment, the vector is a 5/476 vector. In another embodiment, the vector is a 5/911 vector. In another embodiment, the vector is a 5/939 vector. In another embodiment, the vector is a 5/11302 vector. In another embodiment, the vector is a 5/11605 vector. In another embodiment, the vector is a 5/11704 vector. In another embodiment, the vector is a 184 vector. In another embodiment, the vector is a 575 vector. In another embodiment, the vector is a 633 vector. In another embodiment, the vector is a 699/694 vector. In another embodiment, the vector is a 744 vector. In another embodiment, the vector is a 900 vector. In another embodiment, the vector is a 1090 vector. In another embodiment, the vector is a 1317 vector. In another embodiment, the vector is a 1444 vector. In another embodiment, the vector is a 1652 vector. In another embodiment, the vector is a 1806 vector. In another embodiment, the vector is a 1807 vector. In another embodiment, the vector is a 1921/959 vector. In another embodiment, the vector is a 1921/11367 vector. In another embodiment, the vector is a 1921/11500 vector. In another embodiment, the vector is a 1921/11566 vector. In another embodiment, the vector is a 1921/12460 vector. In another embodiment, the vector is a 1921/12582 vector. In another embodiment, the vector is a 1967 vector. In another embodiment, the vector is a 2389 vector. In another embodiment, the vector is a 2425 vector. In another embodiment, the vector is a 2671 vector. In another embodiment, the vector is a 2685 vector. In another embodiment, the vector is a 3274 vector. In another embodiment, the vector is a 3550 vector. In another embodiment, the vector is a 3551 vector. In another embodiment, the vector is a 3552 vector. In another embodiment, the vector is a 4276 vector. In another embodiment, the vector is a 4277 vector. In another embodiment, the vector is a 4292 vector. In another embodiment, the vector is a 4477 vector. In another embodiment, the vector is a 5337 vector. In another embodiment, the vector is a 5348/11363 vector. In another embodiment, the vector is a 5348/11646 vector. In another embodiment, the vector is a 5348/12430 vector. In another embodiment, the vector is a 5348/12434 vector. In another embodiment, the vector is a 10072 vector. In another embodiment, the vector is a 11355C vector. In another embodiment, the vector is a 11711A vector. In another embodiment, the vector is a 12029 vector. In another embodiment, the vector is a 12981 vector. In another embodiment, the vector is a 13441 vector. In another embodiment, the vector is a 90666 vector. In another embodiment, the vector is a 90816 vector. In another embodiment, the vector is a 93253 vector. In another embodiment, the vector is a 907515 vector. In another embodiment, the vector is a 910716 vector. In another embodiment, the vector is a NN-*Listeria* vector. In another embodiment, the vector is a O1761 vector. In another embodiment, the vector is a 4211 vector. In another embodiment, the vector is a 4286 vector.

In another embodiment, the integration vector is any other site-specific integration vector known in the art that is capable of infecting *Listeria*. Each possibility represents a separate embodiment of the present invention.

The metabolic enzyme of methods and compositions of the present invention is, in another embodiment, an amino acid metabolism enzyme. In another embodiment, the metabolic enzyme is an alanine racemase (dal) enzyme. In another embodiment, the metabolic enzyme is a D-amino acid transferase enzyme (dat). The LM dal and dat genes were cloned and isolated from LM as described in Thompson et al (Infec Immun 66: 3552-3561, 1998).

In another embodiment, the metabolic enzyme metabolizes an amino acid (AA) that is used for a bacterial growth process. In another embodiment, the product AA is used for a replication process. In another embodiment, the product AA is used for cell wall synthesis. In another embodiment, the product AA is used for protein synthesis. In another embodiment, the product AA is used for metabolism of a fatty acid. In another embodiment, the product AA is used for any other growth or replication process known in the art. Each possibility represents a separate embodiment of the present invention.

In another embodiment, the metabolic enzyme catalyzes the formation of an AA used in cell wall synthesis. In another embodiment, the metabolic enzyme catalyzes synthesis of an AA used in cell wall synthesis. In another embodiment, the metabolic enzyme is involved in synthesis of an AA used in cell wall synthesis. In another embodiment, the AA is used in cell wall biogenesis. Each possibility represents a separate embodiment of the present invention.

In another embodiment, the metabolic enzyme is a synthetic enzyme for D-glutamic acid, a cell wall component.

In another embodiment, the metabolic enzyme is encoded by an alanine racemase gene (dal) gene. D-glutamic acid synthesis is controlled in part by the dal gene, which is involved in the conversion of D-glu+pyr to alpha-ketoglutarate+D-ala, and the reverse reaction.

The dal gene of methods and compositions of the present invention is encoded, in another embodiment, by the sequence:

```
atggtgacaggctggcatcgtccaacatggattgaaatagaccgcgcagc aattcgcgaaaatataaaaaatgaacaaaataaactcccggaaagtgtcg acttatgggcagtagtcaaagctaatgcatatggtcacggaattatcgaa gttgctaggacggcgaaagaagctggagcaaaaggtttctgcgtagccat tttagatgaggcactggctcttagagaagctggatttcaagatgacttta ttcttgtgcttggtgcaaccagaaaagaagatgctaatctggcagccaaa aaccacatttcacttactgtttttagagaagattggctagagaatctaac gctagaagcaacacttcgaattcatttaaaagtagatagcggtatgggc gtctcggtattcgtacgactgaagaagcacggcgaattgaagcaaccagt actaatgatcaccaattacaactggaaggtatttacacgcattttgcaac agccgaccagctagaaactagttattttgaacaacaattagctaagttcc aaacgattttaacgagtttaaaaaaacgaccaacttatgttcatacagcc aattcagctgcttcattgttacagccacaaatcgggtttgatgcgattcg
```

-continued

```
ctttggtatttcgatgtatggattaactccctccacagaaatcaaaacta gcttgccgtttgagcttaaacctgcacttgcactctataccgagatggtt catgtgaaagaacttgcaccaggcgatagcgttagctacggagcaactta tacagcaacagagcgagaatggggttgcgacattaccaattggctatgcgg atggattgattcgtcattacagtggtttccatgttttagtagacggtgaa ccagctccaatcattggtcgagtttgtatggatcaaaccatcataaaact accacgtgaatttcaaactggttcaaaagtaacgataattggcaaagatc atggtaacacggtaacagcagatgatgccgctcaatatttagatacaatt aattatgaggtaacttgtttgttaaatgagcgcatacctagaaaatacat ccattag
```

(SEQ ID No: 50; GenBank Accession No: AF038438). In another embodiment, the nucleotide encoding dal is homologous to SEQ ID No: 50. In another embodiment, the nucleotide encoding dal is a variant of SEQ ID No: 50. In another embodiment, the nucleotide encoding dal is a fragment of SEQ ID No: 50. In another embodiment, the dal protein is encoded by any other dal gene known in the art. Each possibility represents a separate embodiment of the present invention.

In another embodiment, the dal protein has the sequence:

```
MVTGWHRPTWIEIDRAAIRENIKNEQNKLPESVDLWAVVKANAYGHGIIE

VARTAKEAGAKGFCVAILDEALALREAGFQDDFILVLGATRKEDANLAAK

NHISLTVFREDWLENLTLEATLRIHLKVDSGMGRLGIRTTEEARRIEATS

TNDHQLQLEGIYTHFATADQLETSYFEQQLAKFQTILTSLKKRPTYVHTA

NSAASLLQPQIGFDA1RFGISMYGLTPSTEIKTSLPFELKPALALYTEMV

HVKELAPGDSVSYGATYTATEREWVATLPIGYADGLIRHYSGFHVLVDGE

PAPIIGRVCMDQTIIKLPREFQTGSKVTIIGKDHGNTVTADDAAQYLDTI

NYEVTCLLNERIPRKYIH
```

(SEQ ID No: 51; GenBank Accession No: AF038438). In another embodiment, the dal protein is homologous to SEQ ID No: δ 1. In another embodiment, the dal protein is a variant of SEQ ID No: δ 1. In another embodiment, the dal protein is an isomer of SEQ ID No: 51. In another embodiment, the dal protein is a fragment of SEQ ID No: 51. In another embodiment, the dal protein is a fragment of a homologue of SEQ ID No: 51. In another embodiment, the dal protein is a fragment of a variant of SEQ ID No: 51. In another embodiment, the dal protein is a fragment of an isomer of SEQ ID No: 51.

In another embodiment, the dal protein any other dal protein known in the art. Each possibility represents a separate embodiment of the present invention.

In another embodiment, the dal protein of methods and compositions of the present invention retains its enzymatic activity. In another embodiment, the dal protein retains 90% of wild-type activity. In another embodiment, the dal protein retains 80% of wild-type activity. In another embodiment, the dal protein retains 70% of wild-type activity. In another embodiment, the dal protein retains 60% of wild-type activity. In another embodiment, the dal protein retains 50% of wild-type activity. In another embodiment, the dal protein retains 40% of wild-type activity. In another embodiment, the dal protein retains 30% of wild-type activity. In another embodiment, the dal protein retains 20% of wild-type activity. In another embodiment, the dal protein retains 10% of wild-type activity. In another embodiment, the dal protein retains 5% of wild-type activity. Each possibility represents a separate embodiment of the present invention.

In another embodiment, the metabolic enzyme is encoded by a D-amino acid aminotransferase gene (dat). D-glutamic acid synthesis is controlled in part by the dat gene, which is involved in the conversion of D-glu+pyr to alpha-ketoglutarate+D-ala, and the reverse reaction.

In another embodiment, a dat gene utilized in the present invention has the sequence set forth in GenBank Accession Number AF038439. In another embodiment, the dat gene is any another dat gene known in the art. Each possibility represents a separate embodiment of the present invention.

The dat gene of methods and compositions of the present invention is encoded, in another embodiment, by the sequence:

```
atgaaagtattagtaaataaccatttagttgaaagagaagatgccacagt tgacattgaagaccgcggatatcagtttggtgatggtgtatatgaagtag ttcgtctatataatggaaaattcttacttataatgaacacattgatcgc ttatatgctagtgcagcaaaaattgacttagttattccttattccaaaga agagctacgtgaatacttgaaaaattagttgccgaaaataatatcaata cagggaatgtctatttacaagtgactcgtggtgttcaaaacccacgtaat catgtaatccctgatgatttccctctagaaggcgttttaacagcagcagc tcgtgaagtacctagaaacgagcgtcaattcgttgaaggtggaacggcga ttacagaagaagatgtgcgctggttacgctgtgatattaagagcttaaac cttttaggaaatattctagcaaaaaataaagcacatcaacaaaatgcttt ggaagctattttacatcgcggggaacaagtaacagaatgttctgcttcaa acgtttctattattaaagatggtgtattatggacgcatgcggcagataac ttaatcttaaatggtatcactcgtcaagttatcattgatgttgcgaaaaa gaatggcattcctgttaaagaagcggatttcactttaacagaccttcgtg aagcggatgaagtgttcatttcaagtacaactattgaaattacacctatt acgcatattgacggagttcaagtagctgacggaaaacgtggaccaattac agcgcaacttcatcaatattttgtagaagaaatcactcgtgcatgtggcg aattagagtttgcaaaataa
```

(SEQ ID No: 52; GenBank Accession No: AF038439). In another embodiment, the nucleotide encoding dat is homologous to SEQ ID No: 52. In another embodiment, the nucleotide encoding dat is a variant of SEQ ID No: 52. In another embodiment, the nucleotide encoding dat is a fragment of SEQ ID No: 52. In another embodiment, the dat protein is encoded by any other dat gene known in the art. Each possibility represents a separate embodiment of the present invention.

In another embodiment, the dat protein has the sequence:

```
MKVLVNNHLVEREDATVDIEDRGYQFGDGVYEVVRLYNGKFFTYNEHIDR

LYASAAKIDLVIPYSKEELRELLEKLVAENNINTGNVYLQVTRGVQNPRN
```

-continued

HVIPDDFPLEGVLTAAAREVPRNERQFVEGGTAITEEDVRWLRCDIKSLN

LLGNILAKN1CAHQQNALEAILHRGEQVTECSASNVSIIKDGVLWTHAAD

NLILNGITRQVIIDVAKKNGIPVICEADFTLTDLREADEVFISSTTIEIT

PITHIDGVQVADGKRGPITAQLHQYFVEEITRACGELEFAK (SEQ ID No: 53; GenBank Accession No: AF038439). In another embodiment, the dat protein is homologous to SEQ ID No: 53. In another embodiment, the dat protein is a variant of SEQ ID No: 53. In another embodiment, the dat protein is an isomer of SEQ ID No: 53. In another embodiment, the dat protein is a fragment of SEQ ID No: 53. In another embodiment, the dat protein is a fragment of a homologue of SEQ ID No: 53. In another embodiment, the dat protein is a fragment of a variant of SEQ ID No: 53. In another embodiment, the dat protein is a fragment of an isomer of SEQ ID No: 53.

In another embodiment, the dat protein any other dat protein known in the art. Each possibility represents a separate embodiment of the present invention.

In another embodiment, the dat protein of methods and compositions of the present invention retains its enzymatic activity. In another embodiment, the dat protein retains 90% of wild-type activity. In another embodiment, the dat protein retains 80% of wild-type activity. In another embodiment, the dat protein retains 70% of wild-type activity. In another embodiment, the dat protein retains 60% of wild-type activity. In another embodiment, the dat protein retains 50% of wild-type activity. In another embodiment, the dat protein retains 40% of wild-type activity. In another embodiment, the dat protein retains 30% of wild-type activity. In another embodiment, the dat protein retains 20% of wild-type activity. In another embodiment, the dat protein retains 10% of wild-type activity. In another embodiment, the dat protein retains 5% of wild-type activity. Each possibility represents a separate embodiment of the present invention.

In another embodiment, the metabolic enzyme is encoded by dga. D-glutamic acid synthesis is also controlled in part by the dga gene, and an auxotrophic mutant for D-glutamic acid synthesis will not grow in the absence of D-glutamic acid (Pucci et al, 1995, J. Bacteriol. 177: 336-342). A further example includes a gene involved in the synthesis of diaminopimelic acid. Such synthesis genes encode beta-semialdehyde dehydrogenase, and when inactivated, renders a mutant auxotrophic for this synthesis pathway (Sizemore et al, 1995, Science 270: 299-302).

In another embodiment, the metabolic enzyme is encoded by an alr (alanine racemase) gene. In another embodiment, the metabolic enzyme is any other enzyme known in the art that is involved in alanine synthesis. In another embodiment, the metabolic enzyme is any other enzyme known in the art that is involved in L-alanine synthesis. In another embodiment, the metabolic enzyme is any other enzyme known in the art that is involved in D-alanine synthesis. Bacteria auxotrophic for alanine synthesis are well known in the art, and are described in, for example, *E. coli* (Strych et al, 2002, J. Bacteriol. 184:4321-4325), *Corynebacterium glutamicum* (Tauch et al, 2002, J. Biotechnol 99:79-91), and *Listeria monocytogenes* (Frankel et al, U.S. Pat. No. 6,099,848), *Lactococcus* species, and *Lactobacillus* species, (Bron et al, 2002, Appl Environ Microbiol, 68: 5663-70). In another embodiment, any D-alanine synthesis gene known in the art is inactivated. Each possibility represents a separate embodiment of the present invention.

In another embodiment, the metabolic enzyme is an amino acid aminotransferase.

In another embodiment, the metabolic enzyme is encoded by serC, a phosphoserine aminotransferase. In another embodiment, the metabolic enzyme is encoded by asd (aspartate beta-semialdehyde dehydrogenase), involved in synthesis of the cell wall constituent diaminopimelic acid. In another embodiment, the metabolic enzyme is encoded by gsaB-glutamate-1-semialdehyde aminotransferase, which catalyzes the formation of 5-aminolevulinate from (S)-4-amino-5-oxopentanoate. In another embodiment, the metabolic enzyme is encoded by HemL, which catalyzes the formation of 5-aminolevulinate from (S)-4-amino-5-oxopentanoate. In another embodiment, the metabolic enzyme is encoded by aspB, an aspartate aminotransferase that catalyzes the formation of oxalozcetate and L-glutamate from L-aspartate and 2-oxoglutarate. In another embodiment, the metabolic enzyme is encoded by argF-1, involved in arginine biosynthesis. In another embodiment, the metabolic enzyme is encoded by aroE, involved in amino acid biosynthesis. In another embodiment, the metabolic enzyme is encoded by aroD, involved in amino acid biosynthesis. In another embodiment, the metabolic enzyme is encoded by aroC, involved in amino acid biosynthesis. In another embodiment, the metabolic enzyme is encoded by hisB, involved in histidine biosynthesis. In another embodiment, the metabolic enzyme is encoded by hisD, involved in histidine biosynthesis. In another embodiment, the metabolic enzyme is encoded by hisG, involved in histidine biosynthesis. In another embodiment, the metabolic enzyme is encoded by metX, involved in methionine biosynthesis. In another embodiment, the metabolic enzyme is encoded by proB, involved in proline biosynthesis. In another embodiment, the metabolic enzyme is encoded by argR, involved in arginine biosynthesis. In another embodiment, the metabolic enzyme is encoded by argj, involved in arginine biosynthesis. In another embodiment, the metabolic enzyme is encoded by thil, involved in thiamine biosynthesis. In another embodiment, the metabolic enzyme is encoded by LMOf2365_1652, involved in tryptophan biosynthesis. In another embodiment, the metabolic enzyme is encoded by aroA, involved in tryptophan biosynthesis. In another embodiment, the metabolic enzyme is encoded by ilvD, involved in valine and isoleucine biosynthesis. In another embodiment, the metabolic enzyme is encoded by ilvC, involved in valine and isoleucine biosynthesis. In another embodiment, the metabolic enzyme is encoded by leuA, involved in leucine biosynthesis. In another embodiment, the metabolic enzyme is encoded by dapF, involved in lysine biosynthesis. In another embodiment, the metabolic enzyme is encoded by thrB, involved in threonine biosynthesis (all GenBank Accession No. NC_002973).

In another embodiment, the metabolic enzyme is encoded by murE, involved in synthesis of diaminopimelic acid (GenBank Accession No: NC_003485).

In another embodiment, the metabolic enzyme is encoded by LMOf2365-2494, involved in teichoic acid biosynthesis.

In another embodiment, the metabolic enzyme is encoded by WecE (Lipopolysaccharide biosynthesis protein rffA; GenBank Accession No: AE014075.1). In another embodiment, the metabolic enzyme is encoded by amiA, an N-acetylmuramoyl-L-alanine amidase. In another embodiment, the metabolic enzyme is aspartate aminotransferase. In another embodiment, the metabolic enzyme is histidinol-phosphate aminotransferase (GenBank Accession No. NP_466347). In another embodiment, the metabolic enzyme is the cell wall teichoic acid glycosylation protein GtcA.

In another embodiment, the metabolic enzyme is a synthetic enzyme for a peptidoglycan component or precursor. In another embodiment, the component is UDP-N-acetylmuramyl-pentapeptide. In another embodiment, the component is UDP-N-acetylglucosamine. In another embodiment, the component is MurNAc-(pentapeptide)-pyrophosphoryl-undecaprenol. In another embodiment, the component is GlcNAc-β-(1,4)-MurNAc-(pentapeptide)-pyrophosphoryl-undecaprenol. In another embodiment, the component is any other peptidoglycan component or precursor known in the art. Each possibility represents a separate embodiment of the present invention.

In another embodiment, the metabolic enzyme is encoded by murG. In another embodiment, the metabolic enzyme is encoded by murD. In another embodiment, the metabolic enzyme is encoded by murA-1. In another embodiment, the metabolic enzyme is encoded by murA-2 (all set forth in GenBank Accession No. NC_002973). In another embodiment, the metabolic enzyme is any other synthetic enzyme for a peptidoglycan component or precursor. Each possibility represents a separate embodiment of the present invention.

In another embodiment, the metabolic enzyme is a transglycosylase. In another embodiment, the metabolic enzyme is trans-peptidase. In another embodiment, the metabolic enzyme is a carboxy-peptidase. In another embodiment, the metabolic enzyme is any other class of metabolic enzyme known in the art. Each possibility represents a separate embodiment of the present invention.

In another embodiment, the metabolic enzyme is any other *Listeria monocytogenes* metabolic enzyme known in the art.

In another embodiment, the metabolic enzyme is any other *Listeria* metabolic enzyme known in the art.

In another embodiment, the metabolic enzyme is any other metabolic enzyme known in the art. Each possibility represents a separate embodiment of the present invention.

In another embodiment, the gene encoding the metabolic enzyme is expressed under the control of the *Listeria* p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the gene encoding the metabolic enzyme is expressed under the control of any other promoter that functions in *Listeria*. The skilled artisan will appreciate that other promoters or polycistronic expression cassettes may be used to drive the expression of the gene. Each possibility represents a separate embodiment of the present invention.

The gene expressed on a plasmid of the present invention comprises, in one embodiment, an isolated nucleic acid encoding a protein that complements the auxotrophic mutant. In another embodiment, if the auxotrophic bacteria is deficient in a gene encoding a vitamin synthesis gene (e.g. pantothenic acid) necessary for bacterial growth, the plasmid DNA comprises a gene encoding a protein for pantothenic acid synthesis. Thus, the auxotrophic bacteria, when expressing the gene on the plasmid, can grow in the absence of pantothenic acid, whereas an auxotrophic bacteria not expressing the gene on the plasmid cannot grow in the absence of pantothenic acid.

In another embodiment, an auxotrophic bacterium utilized in methods and compositions of the present invention is deficient in the metabolic enzyme of methods and compositions of the present invention. In another embodiment, the gene encoding the metabolic enzyme is mutated in the genome of the bacterium. In another embodiment, the gene encoding the metabolic enzyme is deleted from the genome of the bacterium. Each possibility represents a separate embodiment of the present invention.

The attPP' of methods and compositions of the present invention is, in another embodiment, a U153 attPP' site. In another embodiment, the attPP site has a sequence contained in SEQ ID No: 26:

```
aagctttaaagaaattcaagaagaaacatcggtaactagccataaattaaccaaagttctaatctcgcttgaagagaacaaactgattgaaaaa
attggacaatctagagcaacaaaatacaaattaattgaatctacagaggaatatctaaccaatcttcaacacacatttcgaaaaattgttcaattttatgtt
gaaaatgataaataaaaatatgaatgttttttatttgttagtagtgtaactttccatgcgagaggagaacggaaatgaaggcagctatttatatacgcgta
tctactcaagaacaaatagagaattactctatacaagctcaaactgaaaagctaacagccttgtgccgctcgaaggattgggacgtatacgatattttcata
gacggcggatacagcggttcaaacatgaatcgccccgcactaaatgaaatgctaagtaaattacatgaaattgatgctgttgttgtatatcgcttagataga
ctttcccgctcacaaagagatacgataacgcttattgaagaatacttcttaaaaaacaatgtagaatttgttagtttgtctgaaactcttgacacctctagc
ccatttgggcgcgcgatgattggtatattatccgtatttgctcaattagagcgcgaaactatacgtgatcgtatggtgatggggaaaattnagcgtattgaa
gcaggtcttcctttaacgactgcaaaaggtagaacattcggctatgatgttatagatactaaattatatattaatgaagaagaagcaaaacaattacaaatg
atttatgatattttttgaggaagaaaaaagcattaccactttacagaagagactaaaaaaattaggattcaaagtgaaatcatatagcagttacaacaattgg
ctaactaatgatttatactgtggttatgtatcttatgcggataaagtgcatacaaaaggtgttcatgagcctatttatttcagaggaacaattttatcgagtt
caagaaattttttctcgcatgggtaaaaatccaaatatgaatagagattcagcatcgttgctaaataatttggtagtgtgtggaaaatgtgggttgggtttt
gttcatcggagaaaagatactgtttcccgcggaaaaaatatcattatagatattatagttgcaagacttacaaacatactcatgaactagaaaaatgtgga
aataaaatttggagagctgacaaactcgaggaattaattattgatcgcgtgaataactatagtttcgcttctaggaatgtagataaagaagacgaattagat
agcttaaatgaaaaacttaaaacagaacacgtaaaaaagaaacggctatttgatttatatatcagcggttcttacgaagtttcagaacttgatgctatgatg
gctgatatcgatgctcaaattaattattatgaagcacaaatagaagctaacgaagaattgaagaaaaataaaaagatacaagaaatttagctgatttagca
acagttgattttgactcttagagttccgagaaaagcaactttatttaaaatcactaattaataaaatttatattgacggtgaacaagttactattgaatgg
ctctagtagcttgtttatttagattgtttagttcctcgttttctctcgttggacggaaacgaatcgagaaactaaaattataaataaaaagtaacctgtttt
```

-continued

```
tctatagattgcttttatcaattatatagaagaaagccgcttttattagattataattgatgttttttgatttatatttcactccctgtgcaaataatga
tataacagcaacctcgaactttttagttcggggtattttttgaaattaatttataaaaacacttgcaattatataatacatgtattataatataaatatag
aaaggagttgagaaagtgaaagacatcttagaggaaataaaaacagtccttgaaattgtaactcttgcagtagcgctgataacattacgcaagatagacaaa
aacaaggacaagtaaccagagggtgaaactcccctccctctataaaagtatatcacgtctttcataaattatgaataaatatatctgggttatattaattg
ttatatgcgttaacggactcgctagttactttcagaacacagcattgaccatcattgctatactgactacattagcttgtttagtatatttaataaaaaata
ggaagtgattaattatgacgaaaaaaacgacctctgacgcgcagttgaaagcaaataaggaatggcaaagcaagaacaaagaacatgcaaactatttaaaat
ctcgttcagctgcgcgttctttataaagaataaagctacgttggaagatttgaaggaacttgaaaaattaattatagagggaaaaattaatcataagggaa
tgattaaggataaatgatgcacgctaagcacatgcttggcgttttttgcataaaaaaagccctaacgttgaagttagggactgacatatataaaaatagaa
gttgacaactttaaggcgactaccacgacaggcagcttacaagctatgactagccttgactaatcatttatgcgacactcaaagaattattatctaacttct
taatcaagaataacaaaaatcaaacaagttagcaagtatttcaggcatttatttataacaaatatctagatcacaaaaatgtcgcggaaaataatggtcac
aaccaatattacataaacttaaaagttctctatttctcttatcaggtttatgtgctgttacgtgatttctacatactctaaaaactgtattagcgaataagt
ctacaacttgaattaaatctttattttgtgaatcctatatgatgtttcaacagaagagaaaattggatgttccattgtaaatttaatagttaaatattctt
gtaagctatttaatgattcaattgcggtatttctatcatctatttgcattttcaaatagttatttgctgggttaattggtattttagaaatttcatttaccg
ttagataaataaaataattaaaagacaaagatgtattattcaaaagatgattgactagttggtggtatcgactatcttaaaatgaaatttagcatctgatt
ttgttgaaagcattattaaatattaattttttcatttcaaaaggcatctccgaacctttatctcttttgtaatatctaacttactagatggatacctttaa
gatattttaattttgcatctctgaactgtctaattacattatatggtttctctgtttctaaaaaagcaataacaaaatatctgttattaaaattttatttt
tagttatagttcctgattcatctacaaaaagtctcatcccagttcctccacttttttacttaaattatattactaattaagtttgaggaagtggaacgta
tgtacttataattcgaagttatgaaaaatcccccatcaatataaaacaaaaaagccccgaaataatcgagggcattaaactaaatcttttaacaaa
cttcggtgttagcagtgagatagtaaccagatttcgttttcaagcgaggtgttccgccttttgttttcgccattcctgtaatcgtgaagatagtgcctaccg
gatatgtgccaccggttttatgcttctcagtaaagtctactgaattgtatagatcacactgtactagtgttttaacttttcgcggattttctgtgtagtatg
tgttttgcttgctggtgtgtggttttcctgcttttaacttcgctaataatgttgtgttctgcgttgctgttcctttataatccttaattccgtattgat
ttgctagttttttacgattcgcaaagctt
```

(SEQ ID No: 26; att site is underlined). In another embodiment, the attPP' site, core integration site, and/or surrounding sequence are homologous to SEQ ID No: 26. In another embodiment, the attPP' site, core integration site, and/or surrounding sequence are a variant of SEQ ID No: 26. In another embodiment, the attPP' site is any other U153 attPP' site known in the art. Each possibility represents a separate embodiment of the present invention.

In another embodiment, the attPP' site is an A118 attPP' site. In another embodiment, the sequence of the site is:

```
tttagtttctcgtttcttcttct tcc aacgagagaaaacgaggaactaaa
```

(SEQ ID No: 42; att site is underlined; GenBank Accession No: AJ242593). In another embodiment, the attPP' site, core integration site, and/or surrounding sequence are homologous to SEQ ID No: 42. In another embodiment, the attPP' site, core integration site, and/or surrounding sequence are a variant of SEQ ID No: 42. In another embodiment, the attPP' site is a site set forth GenBank Accession No. NC_003216. In another embodiment, the attPP' site is any other A118 attPP' site known in the art. Each possibility represents a separate embodiment of the present invention.

In another embodiment, the attPP' site is a PSA attPP' site. In another embodiment, the sequence of the site is:

```
ttacataaaatgtttgtggtattatttgtggtatatatatccta aat ggc
tttatatcagtgtgtgttaatccctctcaggacgttaaatagtaa
```

(SEQ ID No: 43; att site is underlined; GenBank Accession No: AJ312240). In another embodiment, the attPP' site, core integration site, and/or surrounding sequence are homologous to SEQ ID No: 43. In another embodiment, the attPP' site, core integration site, and/or surrounding sequence are a variant of SEQ ID No: 43. In another embodiment, the attPP' site is any other PSA attPP' site known in the art. Each possibility represents a separate embodiment of the present invention.

In another embodiment, the attPP' site is any other attPP' site known in the art. Each possibility represents a separate embodiment of the present invention.

The attBB' site of methods and compositions of the present invention is, in another embodiment, an attBB' site for A118. In another embodiment, the attBB' site has the sequence:

```
ttacataaaatgtttgtggtattatttgtggtattccaaaaaaacttaaga
aggttcttacnattcttagtttttcatatattcttactccaaaaagctagg
catttccctgtgaatatattcattUttctgtaagtttcataaattccgcat
```

-continued

```
gttcctattatcgagagctttatcaatttcagctctaagttgttctaattt tctctcttctaggagcatcgtcaggaagcattcgataaaaacgtttgttaa ttcttttcacccttaaggacacccacctgattcatcaacgaattagaaaa atcacgcatttccacgactaccactccttcactcatatttattacaatctt aaaaaattgtaatatgccaagaaaaaacagaaaacagcttgaaaatacaac tttactaatatctaatgacttgcaaattaccatgtgctataatgacaaaaa ataactcataactaactttgatgcttagtcgttacttagaagttttgctta ttaggcaataactctaggtttcttcttagacataaatacaaacatagagga gttgaatgaaatgaaaaagaacaaatcagtactcagttttatgaagtaaa cccgcacacgatgattattttccaaaaaaatctggaagtatagtctattc agaaatttatgaagttgattctcattatacttctaaatttaccccgtttga gctaattaaaaccagctgtaacttttcggatcaagctatgaaggacgcaaa gagggaactaaacacttaattggtgttacccataagccacccattatcatt gacccagtcacttctacttatgtatttccaactgtagcaccaagttcaaca gaatgcatttggattttcccacaacatattaaagattatcatgcaattgga tttaaccacactttaataacattttctaatatggaaacctttgagattgat atgtctttagcatcttttaataatcagattgccagaacctccatgttacat atgaaattttctcaaaaaatgcgtatgatggagagtaatttcccttcaatg aataggttttcccaccaaccactcttgctgctgaacctaagacgttatta cagcaccatgcttccaaataatgaagaacctaatgatcctcaagatcccga gcaataaatttaaaactaaataaaagccagctacgtaatagtagctggctt ttccttaaaatcattttttattctcaatcgcatctgcaattcgttttaaca ttaataactcatcctctgagtatgtataaggtagttctaaataccatttct cgagttcaggatttccaattaaaggaaaggcgtttaccgaattcttttctc gcaaaccagctacatcatctaataagaaatcggttgttgttccaagaattt ctgctaatttagccaaaataaaaattggcggtcggtggttatcattttcat acttgcttattgtggatgcagttgtcccgattttcgccgccagttgttttn tgtgttaacctattttctttcgtaaatgaattaattttttctccaaattcc aatacgccacctcacttcatccagtatagcaattttttcggaaagaattcg agaaattctaaaagaaatcgcttttaggtttcaaaagacattttcccgt atttatacag
```

(SEQ ID No: 44; att site is underlined; GenBank Accession No: AF174588). In another embodiment, the attBB' site is homologous to SEQ ID No: 44. In another embodiment, the attBB' site is a variant of SEQ ID No: 44. In another embodiment, the attBB' site is any other A118 attBB' site known in the art. Each possibility represents a separate embodiment of the present invention.

In another embodiment, the attBB' site is an attBB' site for PSA. In another embodiment, the attBB' site has the sequence:

```
tgtcctgatagctcagctggatagagcaacggcctTCTaagccgtcggtcg ggggttcgaatccctctcaggacgtaaatagctatatta
```

(SEQ ID No: 45; att site is underlined; GenBank Accession No: AJ314913). In another embodiment, the attBB' site is homologous to SEQ ID No: 45. In another embodiment, the attBB' site is a variant of SEQ ID No: 45. In another embodiment, the attBB' site is any other PSA attBB' site known in the art. Each possibility represents a separate embodiment of the present invention.

In another embodiment, the attBB' site is an attBB' site for U153.

In another embodiment, the attBB' site is within the gene for tRNA$^{Arg}$. In another embodiment, the attBB' site is near the gene for tRNA$^{Arg}$. In another embodiment, the attBB' site is within the gene for comK. In another embodiment, the attBB' site is near the gene for comK. In another embodiment, the attBB' site is within any other LM gene known in the art. In another embodiment, the attBB' site is near any other LM gene known in the art. Each possibility represents a separate embodiment of the present invention.

In another embodiment, the attBB' site is any other attBB' site known in the art. Each possibility represents a separate embodiment of the present invention.

The integrase protein of methods and compositions of the present invention is, in another embodiment, a U153 integrase. In another embodiment, the integrase protein is encoded by a nucleotide molecule having the sequence set forth in residues 272-1630 of SEQ ID No: 26. In another embodiment, the nucleotide encoding the integrase is homologous to SEQ ID No: 26. In another embodiment, the nucleotide encoding the integrase is a variant of SEQ ID No: 26. In another embodiment, the nucleotide encoding the integrase is a fragment of SEQ ID No: 26. In another embodiment, the integrase protein is encoded by any other U153 integrase gene known in the art. Each possibility represents a separate embodiment of the present invention.

In another embodiment, the integrase protein has the sequence:

```
MKAAIYIRVSTQEQIENYSIQAQTEKLTALCRSKDWDVYDIFIDGGYSGSN

MNRPALNEMLSKLHEIDAVVVYRLDRLSRSQRDTITLIEEYFLKNNVEFVS

LSETLDTSSPFGRAMIGILSVFAQLERETIRDRMVMGKIXRIEAGLPLTTA

KGRTFGYDVIDTKLYINEEEAKQLQMIYDIFEEEKSITTLQICRLKKLGFK

VKSYSSYNNWLINDLYCGYVSYADKVHTKGVHEPIISEEQFYRVQEIFSRM

GKNPNMNRDSASLLNNLVVCGKCGLGFVHRRKDTVSRGKKYHYRYYSCKTY

KHTHELEKCGNKIWRADKLEELIIDRVNNYSFASRNVDKEDELDSLNEKLK

TEHVKKKRLFDLYISGSYEVSELDAMMADIDAQINYYEAQIEANEELKKNK

KIQENLADLATVDFDSLEFREKQLYLKSLINKIYIDGEQVTIEWL (SEQ

ID No: 27).
```

In another embodiment, the integrase is homologous to SEQ ID No: 27. In another embodiment, the integrase is a variant of SEQ ID No: 27. In another embodiment, the integrase is an isoform of SEQ ID No: 27. In another embodiment, the integrase is a fragment of SEQ ID No: 27. In another embodiment, the integrase is any other U153 integrase known in the art. Each possibility represents a separate embodiment of the present invention.

In another embodiment, the integrase is a PSA integrase. In another embodiment, the integrase is encoded by a gene having the sequence:

```
ttattccgttgttttgtggcatttgtggtaaaatttgtggtattttcatctgttttagtgtgaaaaaagcatctactttggactgattatgt
tgtcttaaattagagcttagatgactatagtattttaatgttgtattaatgtcatcatgaccaagcctatcagctacataaataatatccataccgcttct
acacataagcctgtatgcgtatgtcgtagcttgtgtaatgtcactggttcagaattgattgtactacatatcttcttcaaagctttattacaagacgcgttg
tctactggcttattgtggtaagtgatgaataataacatcaatggattcttaatagcatgttccttcatataatcagtatgccaatttaaatacgaatgtaaa
tattgagcggtagagttatcaatatagatcactcgtgattttttgttttggtatcaatgaatgtattagtgtacttgtaatcccaagctttattcacagtt
attgaacgtttagtgaaattaatatccttctttgttagtgcaataatttcttcgaacctcatgcctgtctggacagctagaaagataactgctcgtgatata
gaatgaaattttgcaagttcttctaatagtaaatgaactttgtctgtttccataaattgtgctttattttttcgctacgtcctgtccgcttatatgagcccct
atagtgggttttttcttcatgtaacctaaatgaacagccttgttaaaaatcgctctaattttgcggtgtctggtgtctacagtggatattgcatagtctaca
gataaatgattaataaattgttgatattgaaccgcatcaatcgaattaagtttaattttttcatcgaaataatcaacgaattgattataagcaagatcgtat
aaattaatagtagattgactacttttcccatctttaaatgttttcatgaatagcgtataaaattctttgaagttccattctttcagagaactactatcatgc
tgaacttgttttaataatttagatgctttatacattaagtttgtttcacttgtatctgtcaaacgcttttctttccattcaccatcgacttttatacgtagg
cgaacacaatatttaccgtttgctaattttttatcttcat
```

(SEQ ID No: 46; GenBank Accession No: AJ312240). In another embodiment, the nucleotide encoding the integrase is homologous to SEQ ID No: 46. In another embodiment, the nucleotide encoding the integrase is a variant of SEQ ID No: 46. In another embodiment, the nucleotide encoding the integrase is a fragment of SEQ ID No: 46. In another embodiment, the integrase protein is encoded by any other PSA integrase gene known in the art. Each possibility represents a separate embodiment of the present invention.

In another embodiment, the sequence of the integrase is:

MKIKKLANGKYCVRLRIKVDGEWKEKRLTDTSETNLMYKASKLLKQVQHDS

SSLKEWNFICEFYTLFMKTFKDGKSSQSTINLYDLAYNQFVDYFDEKIKLN

SIDAVQYQQFINHLSVDYAISTVDTRHRKIRAIFNICAVHLGYMKKNPTIG

AHISGQDVAKNKAQFMETDKVHLLLEELAKFHSISRAVIFLAVQTGMRFEE

HALTKKDINFTICRSITVNICAWDYKYTNTFIDTKTKKSRVIYIDNSTAQY

LHSYLNWHTDYMKEHAIKNPLMLLFITYHNKPVDNASCNKALKKICSTINS

EPVTLHKLRHTHTGLCVEAGMDIIYVADRLGHDDINTTLKYYSHLSSNLRQ

HNQSKVDAFFTLKTDENTTNFTTNATKTTE (SEQ ID No: 47; GenBank Accession No: AJ312240). In another embodiment, the integrase is homologous to SEQ ID No: 47. In another embodiment, the integrase is a variant of SEQ ID No: 47. In another embodiment, the integrase is an isoform of SEQ ID No: 47. In another embodiment, the integrase is a fragment of SEQ ID No: 47. In another embodiment, the integrase is any other PSA integrase known in the art. Each possibility represents a separate embodiment of the present invention.

In another embodiment, the integrase is an A118 integrase. In another embodiment, the integrase is encoded by a gene having the sequence:

```
caagctactagagccattcaatagtaacttgttcaccatcaatataaattt
tgtttattagtgattttaaataaagttgcttttctctgaactctaaagagt
caaaatcaactgttgctaaatcagctaaattacttgtatcatttgtattct
tcaattcttcgttagatctatttgtgattcataataattaatttgagcatc
aatatcattcatcatagaatcaagttctgaaacttcatacgagccatttat
atataaatcaaataatcgttttttctttgcatgttctattttaagcttttc
atttaagctatctaattcatcttctttatctacatttctggaagcgaaact
ataattattcacacgattaataattaattcttcaagtttgtcagctctcca
aattttattcccgcatttacgagttcatgagtatgtttataagtcttgcaa
ctataatatctataatgatatatttaccacgcgacattgtatctatctacg
atgaacaaagcctaacccgcatttactacaaactactaaattatttagcaa
cgatgctgaatctctattcatgttcggattttttacccatacgagtaaatat
ttcttgaactctatagaattgctcttcactgatgataggttcatgaatacc
ttttacatgaactttatctttatatgaaacataaccacaatacaaatcatt
agttagccagttgttatagcgattatatgttctaactttaaagcctaattt
ttttagtcttttctgtaaaaaagttatactttgttcttcttcgaaaatatc
ataaatcagttgtaactgttttgcttcttcttcattaatgtataattttgt
atctataacatcatagccgaacgttctacctttcgcagttgttaacggaag
acctgcttcaatacgcttaattttccccatcaccatacgatctcggattgt
ttcgcgctctagctgtgcgaatactgataatataccaatcattgcacgacc
gaaaggggaactagtatcaagcgtttcagacaaactaacaaactctacatt
gttttttaagaagtattcttcaataagcgttattgtgtctctttgtgagcg
ggatagtctgtctaatcgatatacgactacagcatcaatttcgtgtagttt
acttagcatttcatttaatgcgggacgattcatatttgagcggagtatcc
gccgtcaatgaaaatatcgtatacgtcccagtccttcgagcggcacaatgc
tgttagttttcagtttgagcttgtattgaataattttctacttgctcttg
agtagaaacacgtatataaatagctgccttcatttcc
```

(SEQ ID No: 48; GenBank Accession No: AJ242593). In another embodiment, the nucleotide encoding the integrase is homologous to SEQ ID No: 48. In another embodiment, the nucleotide encoding the integrase is a variant of SEQ ID No:

48. In another embodiment, the nucleotide encoding the integrase is a fragment of SEQ ID No: 48. In another embodiment, the integrase protein is encoded by any other A118 integrase gene known in the art. Each possibility represents a separate embodiment of the present invention.

In another embodiment, the sequence of the integrase is:

```
MKAAIYIRVSTQEQVENYSIQAQTEKLTALCRSKDWDVYDIFIDGGYSGSN

MNRPALNEMLSKLHEIDAVVVYRLDRLSRSQRDTITL1EEYFLKNNVEFVS

LSETLDTSSPFGRAMIGILSVFAQLERETIRDRMVMGKIKRIEAGLPLTTA

KGRTFGYDVIDTKLYINEEEAKQLQLIYDIFEEEQSITFLQKRLKKLGFKV

RTYNRYNNWLTNDLYCGYVSYKDKVHVKGIHEPIISEEQFYRVQEIFTRMG

KNPNMNRDSASLLNNLVVCSKCGLGFVHRRKDTMSRGKKYHYRYYSCKTYK

HTHELEKCGNKIWRADKLEELIINRVNNYSFASRNVDKEDELDSLNEKLKI

EHAKKKRLFDLYINGSYEVSELDSMMNDIDAQINYYESQIEANEELKKNKK

IQENLADLATVDFDSLEFREKQLYLKSLINKIYIDGEQVTIEWL
```

(SEQ ID No: 49; GenBank Accession No: AJ242593). In another embodiment, the integrase is homologous to SEQ ID No: 49. In another embodiment, the integrase is a variant of SEQ ID No: 49. In another embodiment, the integrase is an isoform of SEQ ID No: 49. In another embodiment, the integrase is a fragment of SEQ ID No: 49. In another embodiment, the integrase is any other A118 integrase known in the art. Each possibility represents a separate embodiment of the present invention.

In another embodiment, the integrase gene is any other integrase gene known in the art. Each possibility represents a separate embodiment of the present invention.

In another embodiment, the integrase gene is expressed under the control of the *Listeria* p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the integrase gene is expressed under the control of any other promoter that functions in *Listeria*. The skilled artisan will appreciate that other promoters or polycistronic expression cassettes may be used to drive the expression of the gene. Each possibility represents a separate embodiment of the present invention.

In another embodiment, the step of incorporating the nucleic acid construct of the present invention into the genome of the auxotrophic *Listeria* strain utilizes two-step allelic exchange. In another embodiment, the step of incorporating utilizes a phage-based integration vector. In another embodiment, the step of incorporating utilizes any other integration method known in the art.

In another embodiment, the step of incorporating the nucleic acid construct utilizes a prophage integration site of the auxotrophic *Listeria* strain. In another embodiment, the step of incorporating utilizes any other integration site known in the art. Each possibility represents a separate embodiment of the present invention.

Each possibility represents a separate embodiment of the present invention.

In another embodiment, the present invention provides a *Listeria monocytogenes*-*Escherichia coli* shuttle plasmid that is retained by complementation of mutant strains deficient in a metabolic gene both in vitro and in vivo. In one embodiment, the metabolic gene is a D-alanine racemase gene. In another embodiment, the metabolic gene is any other metabolic gene of known in the art. Each possibility represents a separate embodiment of the present invention.

In another embodiment, the present invention provides a method of attenuating a bacterial vaccine strain, comprising the steps of (a) introducing into the strain a mutation in a gene encoding a metabolic enzyme; and (b) transfecting the strain with a plasmid containing a nucleotide sequence encoding the metabolic enzyme, thereby attenuating a bacterial vaccine strain.

In another embodiment, the present invention provides a method of attenuating a *Listeria* vaccine strain, comprising the steps of (a) introducing into the strain a mutation in a gene encoding a metabolic enzyme; (b) and transfecting the strain with an integration vector containing a nucleotide sequence encoding the metabolic enzyme, thereby attenuating a metabolic enzyme vaccine strain.

In one embodiment, a metabolic gene of methods and compositions of the present invention are expressed under an inducible promoter. In another embodiment, the promoter is a constitutive promoter. In another embodiment, the promoter is any other type of promoter known in the art. Each possibility represents a separate embodiment of the present invention.

In another embodiment, the present invention provides a bacterial vaccine strain constructed by the method of the present invention.

In another embodiment, the present invention provides a *Listeria* vaccine strain constructed by the method of the present invention.

In various embodiments, the antigen of methods and compositions of the present invention includes but is not limited to antigens from the following infectious diseases, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and AIDS (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae*, *Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

In other embodiments, the antigen is one of the following tumor antigens: any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC 1-KLH antigen associated with breast carcinoma (e.g., GenBank Accession No. J0365 1), CEA (carcinoembryonic antigen) associated with colorectal cancer (e.g., GenBank Accession No. X983 11), gp100 (e.g., GenBank Accession No. S73003) or MARTI antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Tumor antigens encompassed by the present invention further include, but are not limited to, Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)), Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)). Thus, the present invention can be used as immunotherapeutics for cancers including, but not limited to, cervical, breast, colorectal, prostate, lung cancers, and for melanomas.

Each of the above antigens represents a separate embodiment of the present invention.

In another embodiment, the antigen-encoding gene is expressed under the control of the *Listeria* p60 promoter. In another embodiment, the inlA (encodes internalin) promoter is used. In another embodiment, the hly promoter is used. In another embodiment, the ActA promoter is used. In another embodiment, the integrase gene is expressed under the control of any other gram positive promoter. In another embodiment, the antigen-encoding gene is expressed under the control of any other promoter that functions in *Listeria*. The skilled artisan will appreciate that other promoters or polycistronic expression cassettes may be used to drive the expression of the gene. Each possibility represents a separate embodiment of the present invention.

In another embodiment of methods and compositions of the present invention, a polypeptide encoded by a nucleic acid sequence thereof is a fusion protein comprising the heterologous antigen and an additional polypeptide. In one embodiment, the additional polypeptide is a non-hemolytic LLO protein or fragment thereof (Examples herein). In another embodiment, the additional polypeptide is a PEST sequence. In another embodiment, the additional polypeptide is an ActA protein or a fragment thereof. ActA proteins and fragments thereof augment antigen presentation and immunity in a similar fashion to LLO.

The additional polypeptide of methods and compositions of the present invention is, in another embodiment, a listeriolysin (LLO) peptide. In another embodiment, the additional polypeptide is an ActA peptide. In another embodiment, the additional polypeptide is a PEST-like sequence peptide. In another embodiment, the additional polypeptide is any other peptide capable of enhancing the immunogenicity of an antigen peptide. Each possibility represents a separate embodiment of the present invention.

The LLO protein utilized to construct vaccines of the present invention has, in another embodiment, the sequence:

MKKIMLVFITLILVSLPIAQQTEAKDASAFNKENSISSMAPPASPPASP

KTPIEKKHADEIDKYIQGLDYNKNNVLVYHGDAVTNVPPRKGYKDGNEY

IVVEKKKKSINQNNADIQVVNAISSLTYPGALVKANSELVENQPDVLPV

KRDSLTLSIDLPGMTNQDNKIVVKNATKSNVNNAVNTLVERWNEKYAQA

YPNVSAKIDYDDEMAYSESQLIAKFGTAFKAVNNSLNVNFGAISEGKMQ

EEVISFKQIYYNVNVNEPTRPSRFFGKAVTKEQLQALGVNAENPPAYIS

SVAYGRQVYLKLSTNSHSTKVKAAFDAAVSGKSVSGDVELTNIIKNSSF

KAVIYGGSAKDEVQIIDGNLGDLRDILKKGATFNRETPGVPIAYTTNFL

KDNELAVIKNNSEYIETTSKAYTDGKINIDHSGGYVAQFNISWDEVNYD

PEGNEIVQHKNWSENNKSKLAHFTSSIYLPGNARNINVYAKECTGLAWE

WWRTVIDDRNLPLVKNRNISIWGTTLYPKYSNKVDNPIE (GenBank Accession No. P13128; SEQ ID NO: 56; nucleic acid sequence is set forth in GenBank Accession No. X15127). The first 25 amino acids of the proprotein corresponding to this sequence are the signal sequence and are cleaved from LLO when it is secreted by the bacterium. Thus, in this embodiment, the full length active LLO protein is 504 residues long. In another embodiment, the LLO protein is a homologue of SEQ ID No: 56. In another embodiment, the LLO protein is a variant of SEQ ID No: 56. In another embodiment, the LLO protein is an isomer of SEQ ID No: 56. In another embodiment, the LLO protein is a fragment of SEQ ID No: 56. Each possibility represents a separate embodiment of the present invention.

In another embodiment, "LLO peptide" and "LLO fragment" refer to an N-terminal fragment of an LLO protein. In another embodiment, the terms refer to a full-length but non-hemolytic LLO protein. In another embodiment, the terms refer to a non-hemolytic protein containing a point mutation in cysteine 484 of sequence ID No: 56 or a corresponding residue thereof in a homologous LLO protein. In another embodiment, the LLO fragment contains about the first 400-441 AA of the 529 AA full-length LLO protein. Each possibility represents a separate embodiment of the present invention.

In another embodiment, the N-terminal fragment of an LLO protein utilized in compositions and methods of the present invention has the sequence:

MKKIMLVFITLILVSLPIAQQTEAKDASAFNKENSISSVAPPASPPASP

KTPIEKKHADEIDKYIQGLDYNKNNVLVYHGDAVTNVPPRKGYKDGNEY

IVVEKKKKSINQNNADIQVVNAISSLTYPGALVKANSELVENQPDVLPV

KRDSLTLSIDLPGMTNQDNKIVVKNATKSNVNNAVNTLVERWNEKYAQA

YSNVSAKIDYDDEMAYSESQLIAKFGTAFKAVNNSLNVNFGAISEGKMQ

EEVISFKQIYYNVNVNEPTRPSRFFGKAVTKEQLQALGVNAENPPAYIS

SVAYGRQVYLKLSTNSHSTKVKAAFDAAVSGKSVSGDVELTNIIKNSSF

-continued

KAVIYGGSAKDEVQIIDGNLGDLRDILKKGATFNRETPGVPIAYTTNFL

KDNELAVIKNNSEYIETTSKAYTDGKINIDHSGGYVAQFNISWDEVNYD (SEQ ID NO: 57).

In another embodiment, the LLO fragment is a homologue of SEQ ID No: 57. In another embodiment, the LLO fragment is a variant of SEQ ID No: 57. In another embodiment, the LLO fragment is an isomer of SEQ ID No: 57. In another embodiment, the LLO fragment is a fragment of SEQ ID No: 57. Each possibility represents a separate embodiment of the present invention.

In another embodiment, the LLO fragment has the sequence:

MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTD (SEQ ID NO: 58).

In another embodiment, the LLO fragment is a homologue of SEQ ID No: 58. In another embodiment, the LLO fragment is a variant of SEQ ID No: 58. In another embodiment, the LLO fragment is an isomer of SEQ ID No: 58. In another embodiment, the LLO fragment is a fragment of SEQ ID No: 58. Each possibility represents a separate embodiment of the present invention.

In another embodiment, the LLO fragment is any other LLO fragment known in the art. Each possibility represents a separate embodiment of the present invention.

"ActA peptide" refers, in another embodiment, to a full-length ActA protein. In another embodiment, the term refers to an ActA fragment. Each possibility represents a separate embodiment of the present invention.

The ActA fragment of methods and compositions of the present invention is, in another embodiment, an N-terminal ActA fragment. In another embodiment, the fragment is any other type of ActA fragment known in the art. Each possibility represents a separate embodiment of the present invention.

In another embodiment, the N-terminal fragment of an ActA protein has the sequence:

MRAMMVVFITANCITINPDIIFAATDSEDSSLNTDEWEEEKTEEQPSEVN

TGPRYETAREVSSRDIKELEKSNKVRNTNKADLIAMLKEKAEKGPNINNN

NSEQTENAAINEEASGADRPAIQVERRHPGLPSDSAAEIKKRRKAIASSD

SELESLTYPDKPTKVNKKKVAKESVADASESDLDSSMQSADESSPQPLKA

NQQPFFPKVFKKIKDAGKWVRDKIDENPEVKKAIVDKSAGLIDQLLTKKK

SEEVNASDFPPPPTDEELRLALPETPMLLGFNAPATSEPSSFEFPPPPTD

EELRLALPETPMLLGFNAPATSEPSSFEFPPPPTEDELEIIRETASSLDS

SFTRGDLASLRNAINRHSQNFSDFPPIPTEEELNGRGGRP (SEQ ID

No: 59).

In another embodiment, the ActA fragment comprises SEQ ID No: 59. In another embodiment, the ActA fragment is a homologue of SEQ ID No: 59. In another embodiment, the ActA fragment is a variant of SEQ ID No: 59. In another embodiment, the ActA fragment is an isomer of SEQ ID No: 59. In another embodiment, the ActA fragment is a fragment of SEQ ID No: 59. Each possibility represents a separate embodiment of the present invention.

In another embodiment, the N-terminal fragment of an ActA protein has the sequence:

MRAMMVVFITANCITINPDIIFAATDSEDSSLNTDEWEEEKTEEQPSEVN

TGPRYETAREVSSRDIKELEKSNKVRNTNKADLIAMLKEKAEKGPNINNN (SEQ ID No: 60).

In another embodiment, the ActA fragment is a homologue of SEQ ID No: 60. In another embodiment, the ActA fragment is a variant of SEQ ID No: 60. In another embodiment, the ActA fragment is an isomer of SEQ ID No: 60. Each possibility represents a separate embodiment of the present invention.

In another embodiment, the ActA fragment of methods and compositions of the present invention comprises a PEST-like sequence. In another embodiment, the PEST-like sequence contained in the ActA fragment is selected from SEQ ID No: 64-67. In another embodiment, the ActA fragment comprises at least 2 of the PEST-like sequences set forth in SEQ ID No: 64-67. In another embodiment, the ActA fragment comprises at least 3 of the PEST-like sequences set forth in SEQ ID No: 64-67. In another embodiment, the ActA fragment comprises the 4 PEST-like sequences set forth in SEQ ID No: 64-67. Each possibility represents a separate embodiment of the present invention.

In another embodiment, the N-terminal ActA fragment is encoded by a nucleotide molecule having the sequence:

atgcgtgcgatgatggtggttttcattactgccaattgcattacgattaa ccccgacataatatttgcagcgacagatagcgaacattctagtctaaaca cagatgaatgggaagaagaaaaaacagaagagcaaccaagcgaggtaaat acgggaccaagatacgaaactgcacgtgaagtaagttcacgtgatattaa agaactagaaaaatcgaataaagtgagaaatacgaacaaagcagacctaa tagcaatgttgaaagaaaaagcagaaaaaggtccaaatatcaataataac aacagtgaacaaactgagaatgcggctataaatgaagaggcttcaggagc cgaccgaccagctatacaagtggagcgtcgtcatccaggattgccatcgg atagcgc agcggaaattaaaaaaagaaggaaagccatagcatcatcgga tagtgagcttgaaagccttacttatccggataaaccaacaaaagtaaata agaaaaaagtggcgaaagagtcagttgcggatgcttctgaaagtgactta gattctagcatgcagtcagcagatgagtcttcaccacaacctttaaagc aaaccaacaaccattttccctaaagtatttaaaaaaataaaagatgcgg -continued

```
ggaaatgggtacgtgataaaatcgacgaaaatcctgaagtaaagaaagcg attgttgataaaagtgcagggttaattgaccaattattaaccaaaaagaa aagtgaagaggtaaatgcttcggacttcccgccaccacctacggatgaag agttaagacttgctttgccagagacaccaatgcttcttggttttaatgct cctgctacatcagaaccgagctcattcgaatttccaccaccacctacgga tgaagagttaagacttgctttgccagagacgccaatgcttcttggtttta atgctcctgctacatcggaaccgagctcgttcgaatttccaccgcctcca acagaagatgaactagaaatcatccgggaaacagcatcctcgctagattc tagttttacaagaggggatttagctagtttgagaaatgctattaatcgcc atagtcaaaatttctctgatttcccaccaatcccaacagaagaagagttg aacgggagaggcggtagacca (SEQ No: 61).
```

In another embodiment, the ActA fragment is encoded by a nucleotide molecule that comprises SEQ ID No: 61. In another embodiment, the ActA fragment is encoded by a nucleotide molecule that is a homologue of SEQ ID No: 61. In another embodiment, the ActA fragment is encoded by a nucleotide molecule that is a variant of SEQ ID No: 61. In another embodiment, the ActA fragment is encoded by a nucleotide molecule that is an isomer of SEQ ID No: 61. In another embodiment, the ActA fragment is encoded by a nucleotide molecule that is a fragment of SEQ ID No: 61. Each possibility represents a separate embodiment of the present invention.

In another embodiment, a recombinant nucleotide of the present invention comprises any other sequence that encodes a fragment of an ActA protein. Each possibility represents a separate embodiment of the present invention.

In another embodiment, the ActA fragment is any other ActA fragment known in the art. Each possibility represents a separate embodiment of the present invention.

In another embodiment of methods and compositions of the present invention, aPEST-like AA sequence is fused to the antigen peptide. In another embodiment, the PEST-like AA sequence has a sequence selected from SEQ ID No: 62-70. In another embodiment, the PEST-like sequence is any other PEST-like sequence known in the art. Each possibility represents a separate embodiment of the present invention.

In another embodiment, the PEST-like AA sequence is

```
KENSISSMAPPASPPASPKTPIEKKHADEIDK   SEQ ID NO: 62).
```

In another embodiment, the PEST-like sequence is

```
KENSISSMAPPASPPASPK       (SEQ ID No: 63).
```

In another embodiment, fusion of an antigen peptide to any LLO sequence that includes the 1 of the PEST-like AA sequences enumerated herein is efficacious for enhancing cell-mediated immunity against an antigen.

The present invention also provides methods for enhancing cell mediated and anti-tumor immunity and compositions with enhanced immunogenicity which comprise a PEST-like amino acid sequence derived from a prokaryotic organism fused to an antigen. In another embodiment, the PEST-like sequence is embedded within an antigen. In another embodiment, the PEST-like sequence is fused to either the amino terminus of the antigen. In another embodiment, the PEST-like sequence is fused to the carboxy terminus. As demonstrated herein, fusion of an antigen to the PEST-like sequence of LM enhanced cell mediated and anti-tumor immunity of the antigen. Thus, fusion of an antigen to other PEST-like sequences derived from other prokaryotic organisms will also enhance immunogenicity of an antigen. PEST-like sequence of other prokaryotic organism can be identified routinely in accordance with methods such as described by, for example Rechsteiner and Rogers (1996, Trends Biochem. Sci. 21:267-271) for LM. In another embodiment, PEST-like AA sequences from other prokaryotic organisms are identified based by this method. In another embodiment, the PEST-like AA sequence is from another Listeria species. For example, the LM protein ActA contains 4 such sequences.

In another embodiment, the PEST-like AA sequence is a PEST-like sequence from a Listeria ActA protein. In another embodiment, the PEST-like sequence is KTEEQPSEVNT-GPR (SEQ ID NO: 64), KASVTDTSEGDLDSSM-QSADESTPQPLK (SEQ ID NO: 65), KNEEVNASDFPP-PPTDEELR (SEQ ID NO: 66), or RGGIPTSEEFSSLNSGDFTDDENSETTEEEIDR (SEQ ID NO: 67). In another embodiment, the PEST-like sequence is from Listeria seeligeri cytolysin, encoded by the lso gene. In another embodiment, the PEST-like sequence is RSEVTIS-PAETPESPPATP (SEQ ID NO: 68). In another embodiment, the PEST-like sequence is from Streptolysin O protein of Streptococcus sp. In another embodiment, the PEST-like sequence is from Streptococcus pyogenes Streptolysin O, e.g. KQNTASTETTTTNEQPK (SEQ ID NO: 69) at AA 35-51. In another embodiment, the PEST-like sequence is from Streptococcus equisimilis Streptolysin O, e.g. KQNTAN-TETTTTNEQPK (SEQ ID NO: 70) at AA 38-54. In another embodiment, the PEST-like sequence has a sequence selected from SEQ ID No: 62-70. In another embodiment, the PEST-like sequence has a sequence selected from SEQ ID No: 64-70. In another embodiment, the PEST-like sequence is another PEST-like AA sequence derived from a prokaryotic organism.

PEST-like sequences of other prokaryotic organism are identified, in another embodiment, in accordance with methods such as described by, for example Rechsteiner and Rogers (1996, Trends Biochem. Sci. 21:267-271) for LM. Alternatively, PEST-like AA sequences from other prokaryotic organisms can also be identified based by this method. Other prokaryotic organisms wherein PEST-like AA sequences would be expected to include, but are not limited to, other Listeria species. In another embodiment, the PEST-like sequence is embedded within the antigenic protein. Thus, in another embodiment, "fusion" refers to an antigenic protein comprising both the antigen peptide and the PEST-like amino acid sequence either linked at one end of the antigen peptide or embedded within the antigen peptide.

In another embodiment, the PEST-like sequence is identified using the PEST-find program. In another embodiment, a PEST-like sequence is defined as a hydrophilic stretch of at least 12 AA in length with a high local concentration of proline (P), aspartate (D), glutamate (E), serine (S), and/or threonine(T) residues. In another embodiment, a PEST-like sequence contains no positively charged AA, namely arginine (R), histidine (H) and lysine (K).

In another embodiment, identification of PEST motifs is achieved by an initial scan for positively charged AA R, H, and K within the specified protein sequence. All AA between the positively charged flanks are counted and only those motifs are considered further, which contain a number of AA equal to or higher than the window-size parameter. In another embodiment, a PEST-like sequence must contain at least 1 P, 1 D or E, and at least 1 S or T.

In another embodiment, the quality of a PEST motif is refined by means of a scoring parameter based on the local enrichment of critical AA as well as the motifs hydrophobicity. Enrichment of D, E, P, S and T is expressed in mass percent (w/w) and corrected for 1 equivalent of D or E, 1 of P and 1 of S or T. In another embodiment, calculation of hydrophobicity follows in principle the method of J. Kyte and R. F. Doolittle (Kyte, J and Doolittle, R F. J. Mol. Biol. 157, 105 (1982). For simplified calculations, Kyte-Doolittle hydropathy indices, which originally ranged from −4.5 for arginine to +4.5 for isoleucine, are converted to positive integers, using the following linear transformation, which yielded values from 0 for arginine to 90 for isoleucine.

Hydropathy index=10*Kyte-Doolittle hydropathy index+45

In another embodiment, a potential PEST motif's hydrophobicity is calculated as the sum over the products of mole percent and hydrophobicity index for each AA species. The desired PEST score is obtained as combination of local enrichment term and hydrophobicity term as expressed by the following equation:

PEST score=0.55*DEPST−0.5*hydrophobicity index.

In another embodiment, "PEST-like sequence" or "PEST-like sequence peptide" refers to a peptide having a score of at least +5, using the above algorithm. In another embodiment, the term refers to a peptide having a score of at least 6. In another embodiment, the peptide has a score of at least 7. In another embodiment, the score is at least 8. In another embodiment, the score is at least 9. In another embodiment, the score is at least 10. In another embodiment, the score is at least 11. In another embodiment, the score is at least 12. In another embodiment, the score is at least 13. In another embodiment, the score is at least 14. In another embodiment, the score is at least 15. In another embodiment, the score is at least 16. In another embodiment, the score is at least 17. In another embodiment, the score is at least 18. In another embodiment, the score is at least 19. In another embodiment, the score is at least 20. In another embodiment, the score is at least 21. In another embodiment, the score is at least 22. In another embodiment, the score is at least 22. In another embodiment, the score is at least 24. In another embodiment, the score is at least 24. In another embodiment, the score is at least 25. In another embodiment, the score is at least 26. In another embodiment, the score is at least 27. In another embodiment, the score is at least 28. In another embodiment, the score is at least 29. In another embodiment, the score is at least 30. In another embodiment, the score is at least 32. In another embodiment, the score is at least 35. In another embodiment, the score is at least 38. In another embodiment, the score is at least 40. In another embodiment, the score is at least 45. Each possibility represents a separate embodiment of the present invention.

In another embodiment, the PEST-like sequence is identified using any other method or algorithm known in the art, e.g the CaSPredictor (Garay-Malpartida H M, Occhiucci J M, Alves J, Belizario J. E. Bioinformatics. 2005 June; 21 Suppl 1:i69-76). In another embodiment, the following method is used:

A PEST index is calculated for each stretch of appropriate length (e.g. a 30-35 AA stretch) by assigning a value of 1 to the AA Ser, Thr, Pro, Glu, Asp, Asn, or Gln. The coefficient value (CV) for each of the PEST residue is 1 and for each of the other AA (non-PEST) is 0.

Each method for identifying a PEST-like sequence represents a separate embodiment of the present invention.

"Fusion to a PEST-like sequence" refers, in another embodiment, to fusion to a protein fragment comprising a PEST-like sequence. In another embodiment, the term includes cases wherein the protein fragment comprises surrounding sequence other than the PEST-like sequence. In another embodiment, the protein fragment consists of the PEST-like sequence. Each possibility represents a separate embodiment of the present invention.

In one embodiment, a vector of the present invention provides the benefits of a *Listeria* vaccine vector without the risk of increasing antibiotic resistance in bacterial organisms.

In another embodiment, an advantage of vaccine strains of the present invention is that the recombinant nucleic acid molecules or plasmids contained therein are not likely to be retained upon potential transfer to other bacteria in the gut. In another embodiment, the advantage is that the nucleic acid molecules or plasmids do not confer an evolutionary advantage on normal cells. In another embodiment, the advantage is that the nucleic acid molecules or plasmids do not contain active retention systems such as partition sequences. Thus, outside their deficient host cells, the nucleic acid molecules or plasmids will most likely be diluted out of the population and ultimately be eliminated over time. Each possibility represents a separate embodiment of the present invention.

In another embodiment, the present invention provides a kit comprising an antibiotic resistance free bacterial strain of the present invention, a pharmaceutically-acceptable carrier, an applicator, and an instructional material for use thereof.

In another embodiment, the present invention provides a kit comprising an antibiotic resistance free *Listeria* strain of the present invention, an applicator, and an instructional material for use thereof.

"Alanine racemase" refers, in one embodiment, to an enzyme that converts the L-isomer of the amino acid alanine into its D-isomer. In another embodiment, such enzymes are known by the EC number 5.1.1.1.

"Amino acid metabolism enzyme" refers, in one embodiment, to a peptide or protein that has a functional role in converting an amino acid from one form to another, such as, but not limited to, altering the stereochemistry of the amino acid, hydrolyzing or adding groups to an amino acid, cleaving amino acids, and the like. Each possibility represents a separate embodiment of the present invention.

The term "auxotrophic bacteria" refers, in one embodiment, to a bacteria strain that is not capable of growing or replicating without supplementation of a factor that will permit such growth or replication. Each factor represents a separate embodiment of the present invention.

"Fusion protein" refers, in one embodiment, to a protein that comprises two or more proteins linked together. In one embodiment, the proteins are linked by peptide bonds. In another embodiment, the proteins are linked by other chemical bonds. In another embodiment, the proteins are linked by with one or more amino acids between the two or more proteins, which may be referred to as a spacer. Each possibility represents a separate embodiment of the present invention.

In another embodiment, the tumor targeted by methods and compositions of the present invention is a breast cancer. In another embodiment, the cancer is a melanoma. In another embodiment, the cancer is a glioma tumor. In another embodiment, the cancer is an ovarian neoplasm. In another embodiment, the cancer is a mammary carcinoma. In another embodiment, the cancer is an ependymoma.

In another embodiment, the cancer is a melanoma. In another embodiment, the cancer is a sarcoma. In another embodiment, the cancer is a carcinoma. In another embodiment, the cancer is a lymphoma. In another embodiment, the cancer is a leukemia. In another embodiment, the cancer is mesothelioma. In another embodiment, the cancer is a glioma. In another embodiment, the cancer is a germ cell tumor. In another embodiment, the cancer is a choriocarcinoma. Each possibility represents a separate embodiment of the present invention.

In another embodiment, the cancer is pancreatic cancer. In another embodiment, the cancer is ovarian cancer. In another embodiment, the cancer is gastric cancer. In another embodiment, the cancer is a carcinomatous lesion of the pancreas. In another embodiment, the cancer is pulmonary adenocarcinoma. In another embodiment, the cancer is colorectal adenocarcinoma. In another embodiment, the cancer is pulmonary squamous adenocarcinoma. In another embodiment, the cancer is gastric adenocarcinoma. In another embodiment, the cancer is an ovarian surface epithelial neoplasm (e.g. a benign, proliferative or malignant variety thereof). In another embodiment, the cancer is an oral squamous cell carcinoma. In another embodiment, the cancer is non small-cell lung carcinoma. In another embodiment, the cancer is an endometrial carcinoma. In another embodiment, the cancer is a bladder cancer. In another embodiment, the cancer is a head and neck cancer. In another embodiment, the cancer is a prostate carcinoma.

In another embodiment, the cancer is an acute myelogenous leukemia (AML). In another embodiment, the cancer is a myelodysplastic syndrome (MDS). In another embodiment, the cancer is a non-small cell lung cancer (NSCLC). In another embodiment, the cancer is a Wilms' tumor. In another embodiment, the cancer is a leukemia. In another embodiment, the cancer is a lymphoma. In another embodiment, the cancer is a desmoplastic small round cell tumor. In another embodiment, the cancer is a mesothelioma (e.g. malignant mesothelioma). In another embodiment, the cancer is a gastric cancer. In another embodiment, the cancer is a colon cancer. In another embodiment, the cancer is a lung cancer. In another embodiment, the cancer is a breast cancer. In another embodiment, the cancer is a germ cell tumor. In another embodiment, the cancer is an ovarian cancer. In another embodiment, the cancer is a uterine cancer. In another embodiment, the cancer is a thyroid cancer. In another embodiment, the cancer is a hepatocellular carcinoma. In another embodiment, the cancer is a thyroid cancer. In another embodiment, the cancer is a liver cancer. In another embodiment, the cancer is a renal cancer. In another embodiment, the cancer is a kaposis. In another embodiment, the cancer is a sarcoma. In another embodiment, the cancer is another carcinoma or sarcoma. Each possibility represents a separate embodiment of the present invention.

In other embodiments, the antigen of methods and compositions of the present invention is associated with one of the above cancers.

In another embodiment, the cancer is any other cancer known in the art. Each type of cancer represents a separate embodiment of the present invention.

In other embodiments, the antigen of methods and compositions of the present invention is derived from a fungal pathogen, bacteria, parasite, helminth, or viruses. In other embodiments, the antigen is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis pilins*, *N. gonorrhoeae pilins*, or human papilloma virus antigens E1 and E2 from type HPV-16, -18, -31, -33, -35 or -45 human papilloma viruses.

In other embodiments, the antigen is associated with one of the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough3 yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

In another embodiment, the infectious disease of targeted by a method of the present invention is one of the above diseases.

In another embodiment, a sequence of the present invention is homologous to a sequence disclosed herein. The terms "homology," "homologous," etc, when in reference to any protein, peptide, or nucleotide sequence, refer, in one embodiment, to a percentage of amino acid residues in the candidate sequence that are identical with the residues of a corresponding native polypeptide, after aligning the sequences and introducing gaps, if necessary, to achieve the maximum percent homology In another embodiment, conservative substitutions are not considered as part of the sequence identity. In another embodiment, conservative substitutions are considered. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 19, 26-27, 32, and 42-70 of greater than 70%. In another embodiment, "homology" refers to identity to a sequence selected from SEQ ID No: 19, 26-27, 32, and 42-70 of greater than 72%. In another embodiment, "homology" refers to identity to one of SEQ ID No: 19, 26-27, 32, and 42-70 of greater than 75%. In another embodiment, "homology" refers to identity to a sequence selected from SEQ ID No: 19, 26-27, 32, and 42-70 of greater than 78%. In another embodiment, "homology" refers to identity to one of SEQ ID No: 19, 26-27, 32, and 42-70 of greater than 80%. In another embodiment, "homology" refers to identity to one of SEQ ID No: 19, 26-27, 32, and 42-70 of greater than 82%. In another embodiment, "homology" refers to identity to a sequence selected from SEQ ID No: 19, 26-27, 32, and 42-70 of greater than 83%. In another embodiment, "homology" refers to identity to one of SEQ ID No: 19, 26-27, 32, and 42-70 of greater than 85%. In another embodiment, "homology" refers to identity to one of SEQ ID No: 19, 26-27, 32, and 42-70 of greater than 87%. In another embodiment, "homology" refers to identity to a sequence selected from SEQ ID No: 19, 26-27, 32, and 42-70 of greater than 88%. In another embodiment, "homology" refers to identity to one of SEQ ID No: 19, 26-27, 32, and 42-70 of greater than 90%. In another embodiment, "homology" refers to identity to one of SEQ ID No: 19, 26-27, 32, 43 and 42-70 of greater than 92%. In another embodiment, "homology" refers to identity to a sequence selected from SEQ ID No: 19, 26-27, 32, and 42-70 of greater than 93%. In another embodiment, "homology" refers to identity to one of SEQ ID No: 19, 26-27, 32, and 42-70 of greater than 95%. In another embodiment, "homology" refers to identity to a sequence selected from SEQ ID No: 19, 26-27, 32, and 42-70 of greater than 96%. In another embodiment, "homology" refers to identity to one of SEQ ID No: 19, 26-27, 32, and 42-70 of greater than 97%. In another embodiment, "homology" refers to identity to one of SEQ ID No: 19, 26-27, 32, and 42-70 of greater than 98%. In another embodiment, "homology" refers to identity to one of SEQ ID No: 19, 26-27, 32, and 42-70 of greater than 99%. In another embodiment, "homology" refers to identity to one of SEQ ID No: 19, 26-27, 32, and 42-70 of 100%. Each possibility represents a separate embodiment of the present invention.

In another embodiment, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

Describing two polynucleotides as "operably linked" means, in another embodiment, that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

"Promoter/regulatory sequence" refers, in one embodiment, to a nucleic acid sequence which is required for, or enhances, expression of a gene product operably linked to the promoter/regulatory sequence. In another embodiment, this sequence is the core promoter sequence. In another embodiment, this sequence also includes an enhancer sequence and other regulatory elements that are required for expression of the gene product.

*Listeria* Vaccine Strains

The *Listeria* strain of methods and compositions of the present invention is, in another embodiment, *Listeria monocytogenes* (ATCC No. 15313). In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of any other *Listeria* species known in the art.

In other embodiments, attenuated *Listeria* strains, such as LM delta-acta mutant (Brundage et al, 1993, Proc. Natl. Acad. Sci., USA, 90:11890-11894), or *L. monocytogenes* delta-plcA (Camilli et al, 1991, J. Exp. Med., 173:751-754) are used in the present invention. In another embodiment, new attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 61:2245-2248) and mutant for the formation of lipoteichoic acids (Abachin et al, 2002, Mol. Microbiol. 43:1-14).

In another embodiment, a recombinant *Listeria* strain of the present invention has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the *Listeria* strain contains a genomic insertion of the gene encoding the antigen-containing recombinant peptide. In another embodiment, the *Listeria* strain carries a plasmid comprising the gene encoding the antigen-containing recombinant peptide. In another embodiment, the passaging is performed as described herein (e.g. in Example 1). In another embodiment, the passaging is performed by any other method known in the art. Each possibility represents a separate embodiment of the present invention.

The skilled artisan, when equipped with the present disclosure and the methods herein, will readily understand that different transcriptional promoters, terminators, carrier vectors or specific gene sequences (e.g. those in commercially available cloning vectors) can be used successfully in methods and compostions of the present invention. As is contemplated in the present invention, these functionalities are provided in, for example, the commercially available vectors known as the pUC series. In another embodiment, non-essential DNA sequences (e.g. antibiotic resistance genes) are removed.

In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art. Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present invention include, but are not limited to, gene products that confer resistance to ampicillin, penicillin, methicillin, I streptomycin, erythromycin, kanamycin, tetracycline, cloramphenicol (CAT), neomycin, hygromycin, gentamicin and others well known in the art. Each gene represents a separate embodiment of the present invention.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the *Listeria* vaccine strain of the present invention is transformed by electroporation. Each method represents a separate embodiment of the present invention.

Plasmids and other expression vectors useful in the present invention are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of bacteriophage lambda ($P_L$ and $P_R$), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and *Streptomyces* promoters (Ward et al, 1986, Mol. Gen. Genet. 203:468-478). Additional prokaryotic promoters contemplated in the present invention are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present invention include, but are not limited to the Listerial prfA promoter, the Listerial hly promoter, the Listerial p60 promoter and the Listerial ActA promoter (GenBank Acc. No. NC_003210) or fragments thereof.

In another embodiment, a plasmid of methods and compositions of the present invention comprises a gene encoding a fusion protein. In another embodiment, subsequences are cloned and the appropriate subsequences cleaved using appropriate restriction enzymes. The fragments are then, in another embodiment, ligated to produce the desired DNA sequence. In another embodiment, DNA encoding the antigen is produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid. Each method represents a separate embodiment of the present invention.

In another embodiment, the present invention further comprises a phage based chromosomal integration system for clinical applications. A host strain that is auxotrophic for essential enzymes, including, but not limited to, d-alanine racemase will be used, for example Lmdal(−)dat(−). In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current invention enables the establishment of a phage based chromosomal integration system that does not require selection with antibiotics. Instead, an auxotrophic host strain will be complemented.

The recombinant proteins of the present invention are synthesized, in another embodiment, using recombinant DNA methodology. This involves, in one embodiment, creating a DNA sequence that encodes the fusion protein, placing the DNA in an expression cassette, such as the plasmid of the present invention, under the control of a particular promoter/regulatory element, and expressing the protein. DNA encoding the fusion protein (e.g. non-hemolytic LLO/antigen) of the present invention is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then be ligated to produce the desired DNA sequence.

In another embodiment, DNA encoding the fusion protein or the recombinant protein of the present invention is cloned using DNA amplification methods such as polymerase chain reaction (PCR). Thus, the gene for non-hemolytic LLO is PCR amplified, using a sense primer comprising a suitable restriction site and an antisense primer comprising another restriction site, e.g. a non-identical restriction site to facilitate cloning. The same is repeated for the isolated nucleic acid encoding an antigen. Ligation of the non-hemolytic LLO and antigen sequences and insertion into a plasmid or vector produces a vector encoding non-hemolytic LLO joined to a terminus of the antigen. The two molecules are joined either directly or by a short spacer introduced by the restriction site.

In another embodiment, the molecules are separated by a peptide spacer consisting of one or more amino acids, generally the spacer will have no specific biological activity other than to join the proteins or to preserve some minimum distance or other spatial relationship between them. In another embodiment, the constituent AA of the spacer are selected to influence some property of the molecule such as the folding, net charge, or hydrophobicity. In another embodiment, the nucleic acid sequences encoding the fusion or recombinant proteins are transformed into a variety of host cells, including E. coli, other bacterial hosts, such as Listeria, yeast, and various higher eukaryotic cells such as the COS, CHO and HeLa cells lines and myeloma cell lines. The recombinant fusion protein gene will be operably linked to appropriate expression control sequences for each host. Promoter/regulatory sequences are described in detail elsewhere herein. In another embodiment, the plasmid further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

The antigens of these and other diseases are well known in the art, and the skilled artisan, when equipped with the present disclosure and the methods and techniques described herein will readily be able to construct a fusion protein comprising a non-hemolytic LLO protein and an antigen for use in the present invention. In another embodiment, in order to select for an auxotrophic bacteria comprising the plasmid, transformed auxotrophic bacteria are grown on a media that will select for expression of the amino acid metabolism gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present invention if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.). Each method represents a separate embodiment of the present invention.

In another embodiment, once the auxotrophic bacteria comprising the plasmid of the present invention have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the Listeria vaccine vector by adjusting the volume of the media in which the auxotrophic bacteria comprising the plasmid are growing.

The skilled artisan will appreciate that, in another embodiment, other auxotroph strains and complementation systems may be adopted for the use with this invention.

Experimental Details Section

EXAMPLE 1

A Plasmid Containing an Amino Acid Metabolism Enzyme Instead of an Antibiotic Resistance Gene is Retained in E. Coli and LM Both In Vitro and In Vivo Materials and Experimental Methods Bacterial Strains, Transformation and Selection E. coli strain MB2159 was used for transformations, using standard protocols. Bacterial cells were prepared for electroporation by washing with $H_2O$.

E. coli strain MB2159 (Strych U et al, FEMS Microbiol Lett. 2001 Mar. 15; 196(2):93-8) is an air (−)/dadX (−) deficient mutant that is not able to synthesize D-alanine racemase. Listeria strain Lm dal(−)/dat(−) (Lmdd) similarly is not able to synthesize D-alanine racemase due to partial deletions of the dal and the dat genes.

Construction of Lmdd

The dal gene was initially inactivated by means of a double-allelic exchange between the chromosomal gene and the temperature-sensitive shuttle plasmid pKSV7 (Smith K et al, Biochimie. 1992 July-August;74(7-8):705-11) carrying an erythromycin resistance gene between a 450-bp fragment from the 5' end of the original 850-bp dal gene PCR product and a 450-bp fragment from the 3' end of the dal gene PCR product. Subsequently, a dal deletion mutant covering 82% of the gene was constructed by a similar exchange reaction with pKSV7 carrying homology regions from the 5' and 3' ends of the intact gene (including sequences upstream and downstream of the gene) surrounding the desired deletion. PCR analysis was used to confirm the structure of this chromosomal deletion.

The chromosomal dat gene was inactivated by a similar allelic exchange reaction. pKSV7 was modified to carry 450-bp fragments derived by PCR from both the 5' and 3' ends of the intact dat gene (including sequences upstream and downstream of the gene). These two fragments were ligated by appropriate PCR. Exchange of this construct into the chromosome resulted in the deletion of 30% of the central bases of the dat gene, which was confirmed by PCR analysis.

Bacterial Culture and In Vivo Passaging of Listeria

E. coli were cultured following standard methods. Listeria were grown at 37° C., 250 rpm shaking in LB media (Difco, Detroit, Mich.). +50 µg/ml streptomycin, and harvested during exponential growth phase. For Lm-LLOE7, 37 µg/ml chloramphenicol was added to the media. For growth kinetics determinations, bacteria were grown for 16 hours in 10 ml of LB+ antibiotics. The $OD_{600\ nm}$ was measured and culture densities were normalized between the strains. The culture was diluted 1:50 into LB+ suitable antibiotics and D-alanine if applicable.

Passaging of Lm in Mice $1 \times 10^8$ CFU were injected intraperitoneally (ip.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Construction of Antibiotic Resistance Factor Free Plasmid pTV3

Construction of p60-dal cassette. The first step in the construction of the antibiotic resistance gene-free vector was construction of a fusion of a truncated p60 promoter to the dal gene. The LM alanine racemase (dal) gene (forward primer: 5'-CCA TGG TGA CAG GCT GGC ATC-3'; SEQ ID NO: 1) (reverse primer: 5'-GCT AGC CTA ATG GAT GTA TTT TCT AGG-3'; SEQ ID NO: 2) and a minimal p60 promoter sequence (forward primer: 5'-TTA ATT AAC AAA TAG TTG GTA TAG TCC-3'; SEQ ID No: 3) (reverse primer: 5'-GAC GAT GCC AGC CTG TCA CCA TGG AAA ACT CCT CTC-3'; SEQ ID No: 4) were isolated by PCR amplification from the genome of LM strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGTTGGTAT-AGTCCTCTTTAGCCTTTGGAGTATTATCTCATC-ATTTGTTTTTAGGTGAAAACTGGGTAAACTTA-GTATTATCAATATAAAATTAATTCTCAAATACTT- AAT-TACGTACTGGGATTTTCTGAAAAAAGAGAGG-AGTTTTCC (SEQ ID NO: 5, Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of antibiotic resistance genes from pGG55. The subsequent cloning strategy for removing the Chloramphenicol acetyltransferase (CAT) genes from pGG55 and introducing the p60-dal cassette also intermittently resulted in the removal of the gram-positive replication region (oriRep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGCCAC-TAACTCAACGCTAGTAG, SEQ ID NO: 6) and a 3'-primer that added a NheI site downstream of the sequence (GCTAGCCAGCAAAGAAAAACAAACACG, SEQ ID NO: 7). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in. pGG55 was amplified from pCR-oriRep by PCR (primer 1,5'-GTC GAC GGT CAC CGG CGC CAC TAA CTC AAC GCT AGT AG-3'; SEQ ID No: 8); (primer 2, 5'-TTA ATT AAG CTA GCC AGC AAA GAA AAA CAA ACA CG-3'; SEQ ID No: 9) to introduce additional restriction sites for EheI and NheI. The PCR product was ligated into pCR2.1-TOPO (Invitrogen, Carlsbad, Calif.), and the sequence was verified. The replication region was excised by EheI/NheI digestion, and vector pGG55 was double digested with EbeI and NheI, removing both CAT genes from the plasmid simultaneously. The two inserts, p60-dal and oriRep, and the pGG55 fragment were ligated together, yielding pTV3. pTV3 also contains a prfA (pathogenicity regulating factor A) gene. This gene is not necessary for the function of pTV3, but can be used in situations wherein an additional selected marker is required or desired.

Preparation of DNA for Real-Time PCR

Total Listeria DNA was prepared using the Masterpure® Total DNA kit (Epicentre, Madison, Wis.). Listeria were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LL0-E7 gene was PCR amplified from pGG55 (5'-AT-GAAAAAAATAATGCTAGTTTTTATTAC-3' (SEQ ID NO: 10); 5'-GCGGCCGCTTAATGATGATGATGATGAT-GTGGTTTCTGAGAACAGATG-3' (SEQ ID NO: 11)) and cloned into vector pETbluel (Novagen, San Diego, Calif.). Similarly, the plcA amplicon was cloned into pCR2.1. E. coli were transformed with pET-LLOE7 and pCR-plcA, respectively, and purified plasmid DNA was prepared for use in real-time PCR.

Real-Time PCR

Taqman primer-probe sets (Applied Biosystems, Foster City, Calif.) were designed using the ABI PrimerExpress software (Applied Biosystems) with E7 as a plasmid target, using the following primers: 5'-GCAAGTGTGACTC-TACGCTTCG-3' (SEQ ID NO: 12); 5'-TGCCCATTAA-CAGGTCTTCCA-3' (SEQ ID NO: 13); 5'-FAM-TGCGTA CAAAGCACACACGTAGACATTCGTAC-TAMRA-3' (SEQ ID NO: 14) and the one-copy gene picA (TGA-CATCGTTTGTGTTTGAGCTAG-3' (SEQ ID NO: 15), 5'-GCAGCGCTCTCTATACCAGGTAC-3' (SEQ ID NO: 16); 5'-TET-TTAATGTCCATGTTA TGTCTCCGTTAT-AGCTCATCGTA-TAMRA-3'; SEQ ID NO: 17) as a Listeria genome target.

0.4 µM primer and 0.05 mM probe were mixed with PuRE Taq RTG PCR beads (Amersham, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/picA copies were calculated based on the standard curves and calibrated by dividing the results for Lmdd-TV3 and Lm-LLOE7 with the results from Lm-E7, a Listeria strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium +/−100 micrograms (µg)/ml D-alanine and/or 37 μg/ml chloramphenicol. The starting inoculum was adjusted based on $OD_{600}$ nm measurements to be the same for all strains.

Results

Figure 1B:
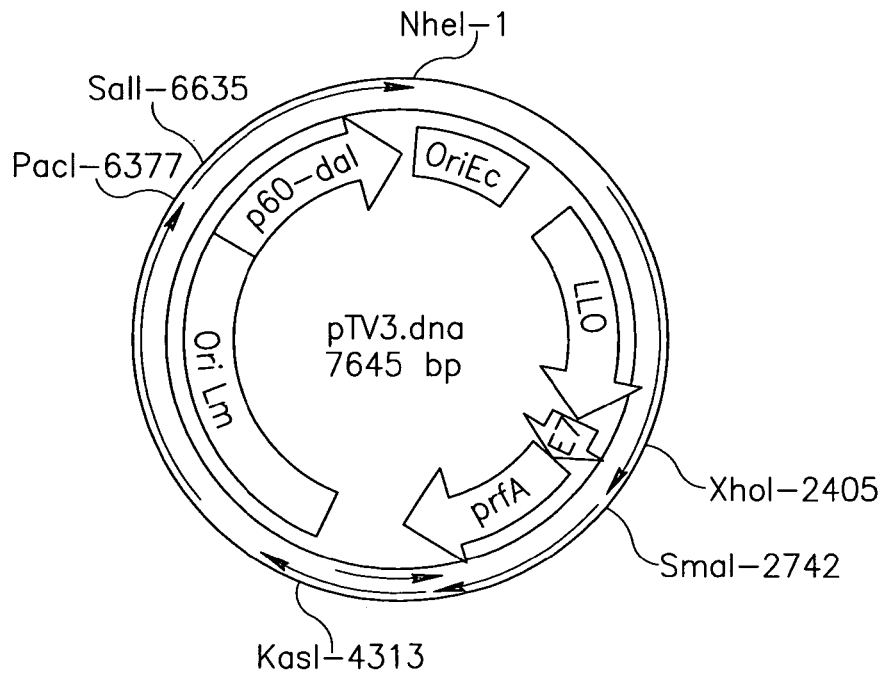
Figure 2:
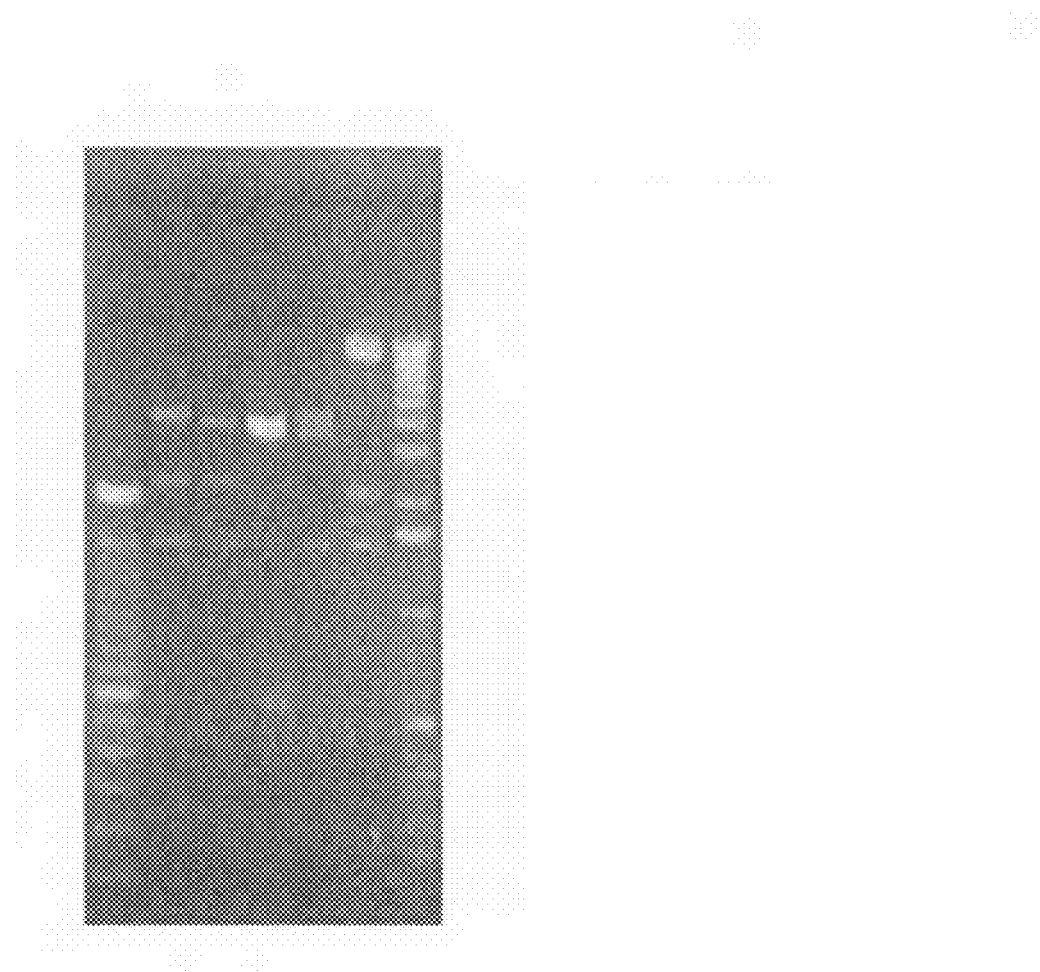
FIG. 2: Plasmid preparation of pTV3 from *E. coli* strain MB2159. Qiagen® midi-preparation of nucleic acids was following the manufacturer's protocol. Lanes from left to right: Lanes 1 and 7: Molecular Weight Marker, 100 Bp ladder (Invitrogen). Lane 2: pTV3, clone #15. Lane 3: pTV3, clone #16. Lane 4: pTV3C, clone #22. Lane 5: pTV3C, clone #24. Lane 6: pGG55 control.

An auxotroph complementation system based on D-alanine racemase was utilized to mediate plasmid retention in LM without the use of an antibiotic resistance gene. *E. coli* strain MB2159 is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes. Plasmid pGG55, which is based on *E. coli-Listeria* shuttle vector pAM401, was modified by removing both CAT genes and replacing them with a p60-dal expression cassette under control of the *Listeria* p60 promoter to generate pTV3 (FIG. 1). DNA was purified from several colonies (FIG. 2).

Figure 3A:
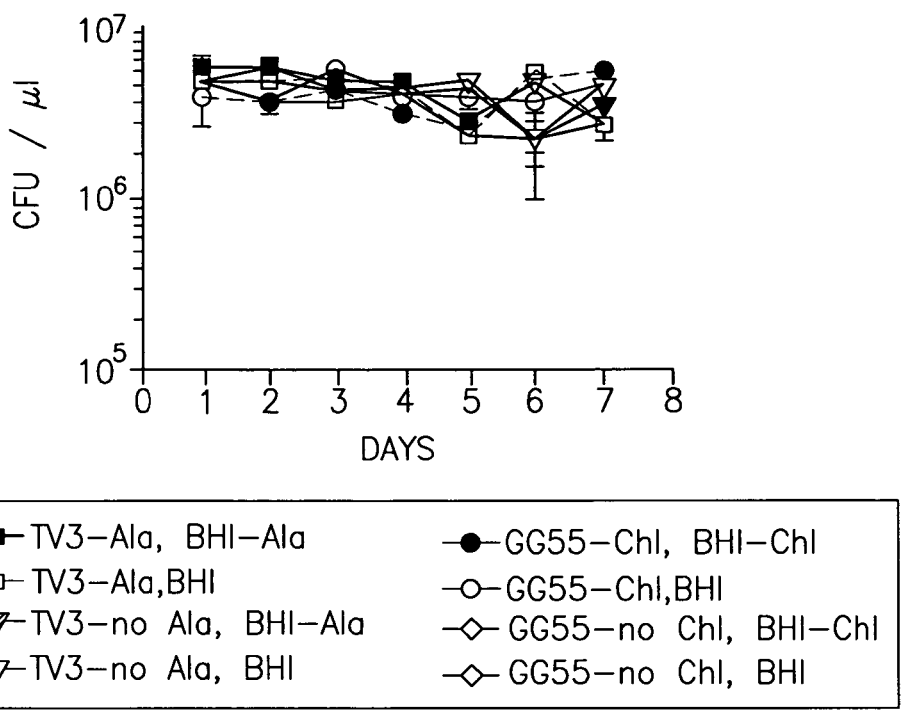
FIG. 3. Plasmid maintenance in vitro (A) and in vivo (B). To determine in vitro stability, strains were cultured with (GG55-Chl) and without (GG55-no Chl) chloramphenicol (LM-LLO-E7) or with and without D-alanine [Lmdd (pTV3)]. The cultures were diluted 1:1000 daily into fresh LB. The CFU of the cultures were determined daily on BHI (BHI) and on BHI with chloramphenicol (BHI-Chl) for LM-LLO-E7 or on BHI with D-alanine (BHI-Ala) for Lmdd (pTV3). All liquid medium and plates contained an additional 50 µg of streptomycin per ml, to which *Listeria monocytogenes* (LM) strain 10403S is naturally resistant. To determine in vivo plasmid maintenance, LM was injected intraperitoneally at a dose of 1/10 the LD50 in50 C57BL/6 mice. Spleens were harvested at different time points post-injection and homogenized in phosphate-buffered saline (PBS). CFU counts were prepared on BHI plates with and without D-alanine for Lmdd (pTV3), on BHI plates with and without chloramphenicol for LM-LLO-E7, and on BHI plates only for wild-type 10403S.

To determine plasmid stability in vitro, LM-LLO-E7 and Lmdd(pTV3) were cultured for 70 generations in the presence and absence of selective pressure. CFU were determined daily on selective and nonselective plates for each culture. In this system, plasmid loss results in a greater number of colonies growing on nonselective plates (BHI plus D-alanine for Lmdd(pTV3), BHI only for LM-LL0-E7) versus selective plates (BHI only for Lmdd(pTV3), BHI plus chloramphenicol for LM-LLO-E7). No difference in CFU was detected between nonselective and selective plates (FIG. 3A), indicating stable maintenance of the plasmid throughout the culture for at least 70 generations, when the experiment was terminated.

Figure 3B:
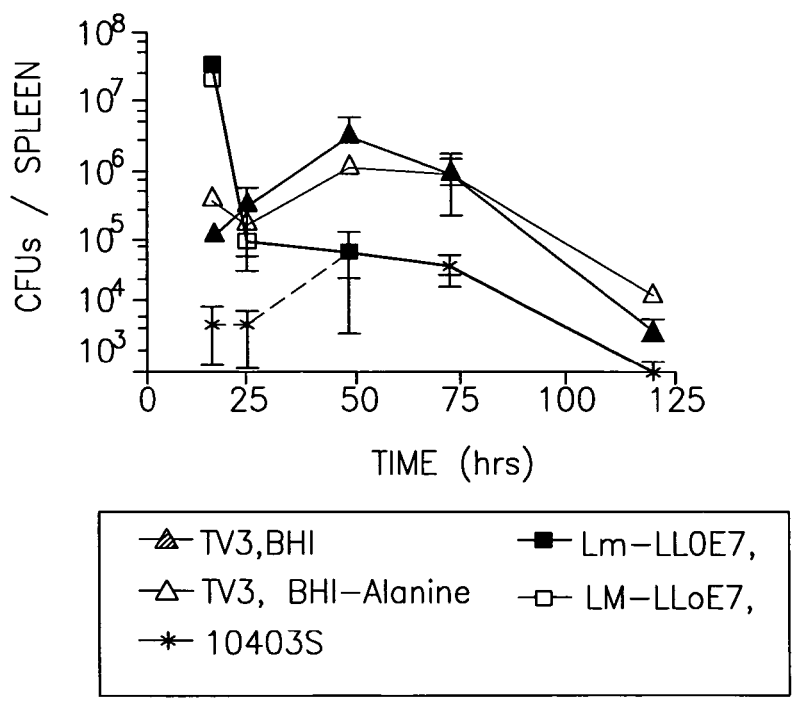
Figure 4:
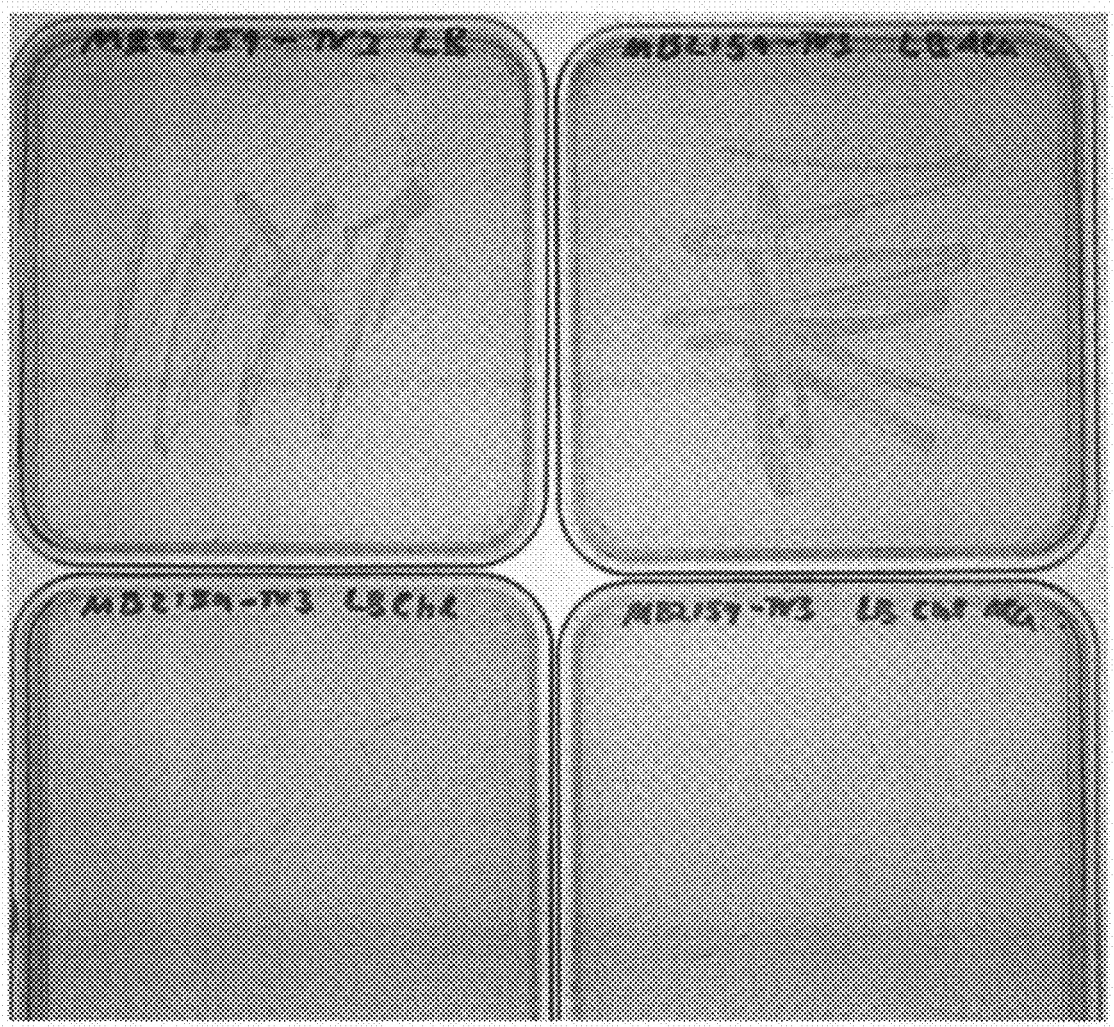
FIG. 4 depicts growth on Luria-Bertoni (LB) agar plates of *E. coli* strain MB2159 (alanine racemace negative) transformed with the pTV3 vector. Bacteria were plated on different media: Upper left: agar alone. MB2159-TV3 is able to grow. Upper right: agar with alanine. MB2159-TV3 is able to grow. Lower left: agar with chloramphenicol. MB2159-TV3 does not grow because the CAT gene is missing. Lower right: agar with chloramphenicol and alanine. MB2159-TV3 does not grow because the CAT gene is missing.
Figure 5:
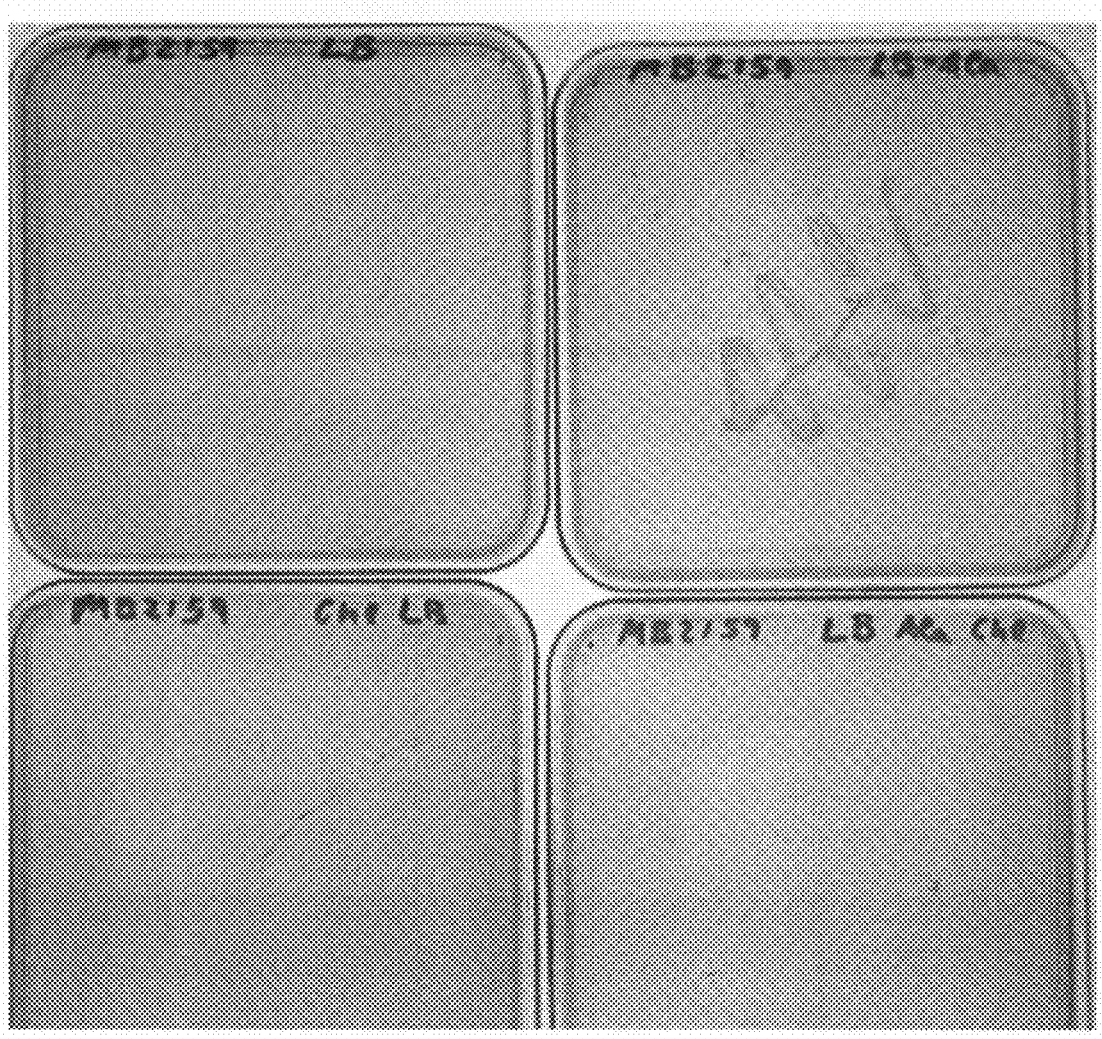
FIG. 5 depicts growth on LB-agar plates of *E. coli* strain MB2159 without the pTV3 vector. Agar plates are arranged as in FIG. 4. Upper left: MB2159 does not grow. Upper right: agar with alanine. MB2159 is able to grow. Lower left: agar with chloramphenicol. MB2159 does not grow. Lower right. MB2159 does not grow.
Figure 6:
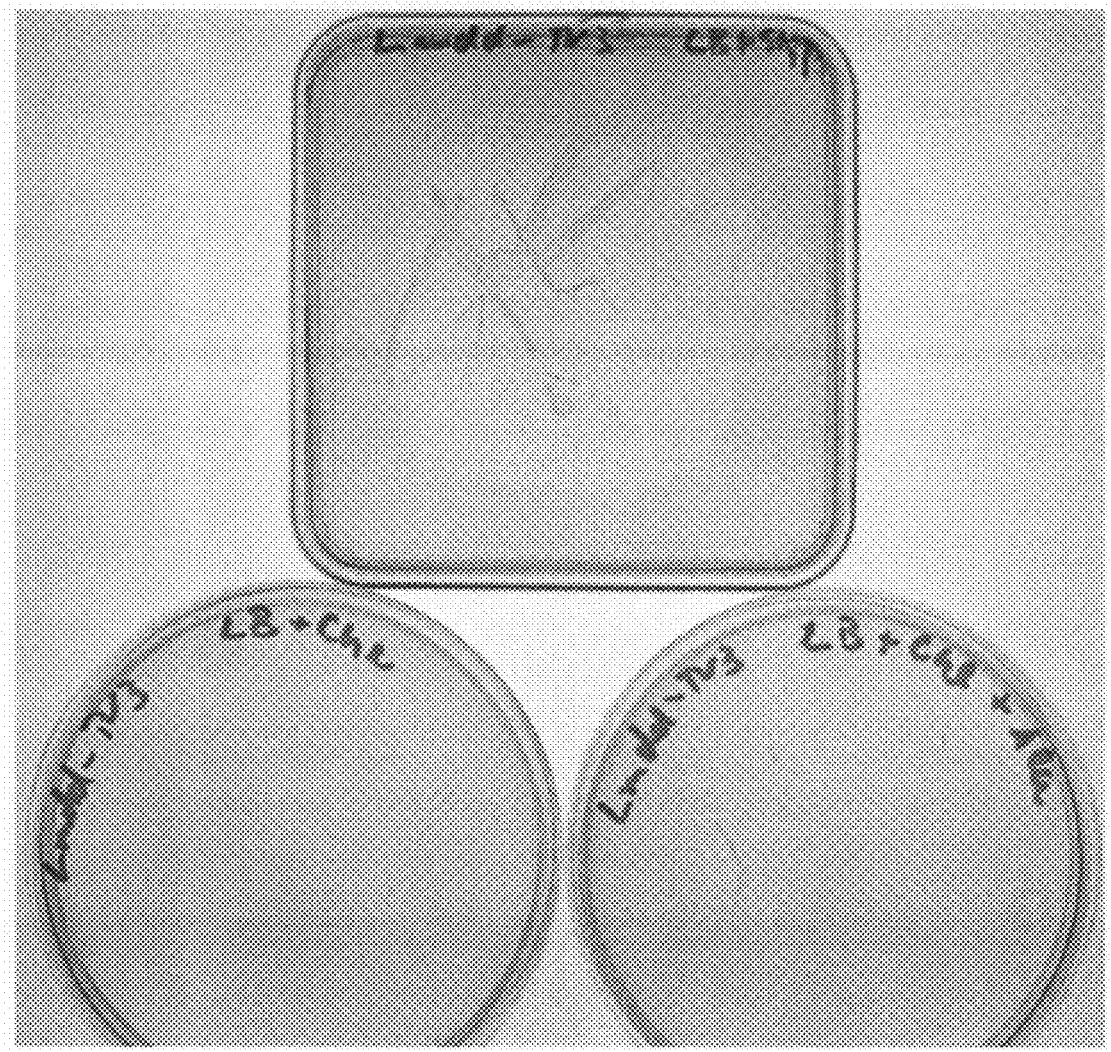
FIG. 6 depicts growth on LB-agar plates of LM strain Lmdd(−) transformed with the pTV3 vector. Bacteria were plated on different media: Top: agar with streptomycin, no added alanine. Lmdd-pTV3 is able to grow (the host strain 10403s is streptomycin resistant). Lower left (agar with chloramphenicol) and lower right (agar with chloramphenicol and alanine): Lmdd-pTV3 does not grow because the CAT gene is not present in pTV3.
Figure 7:
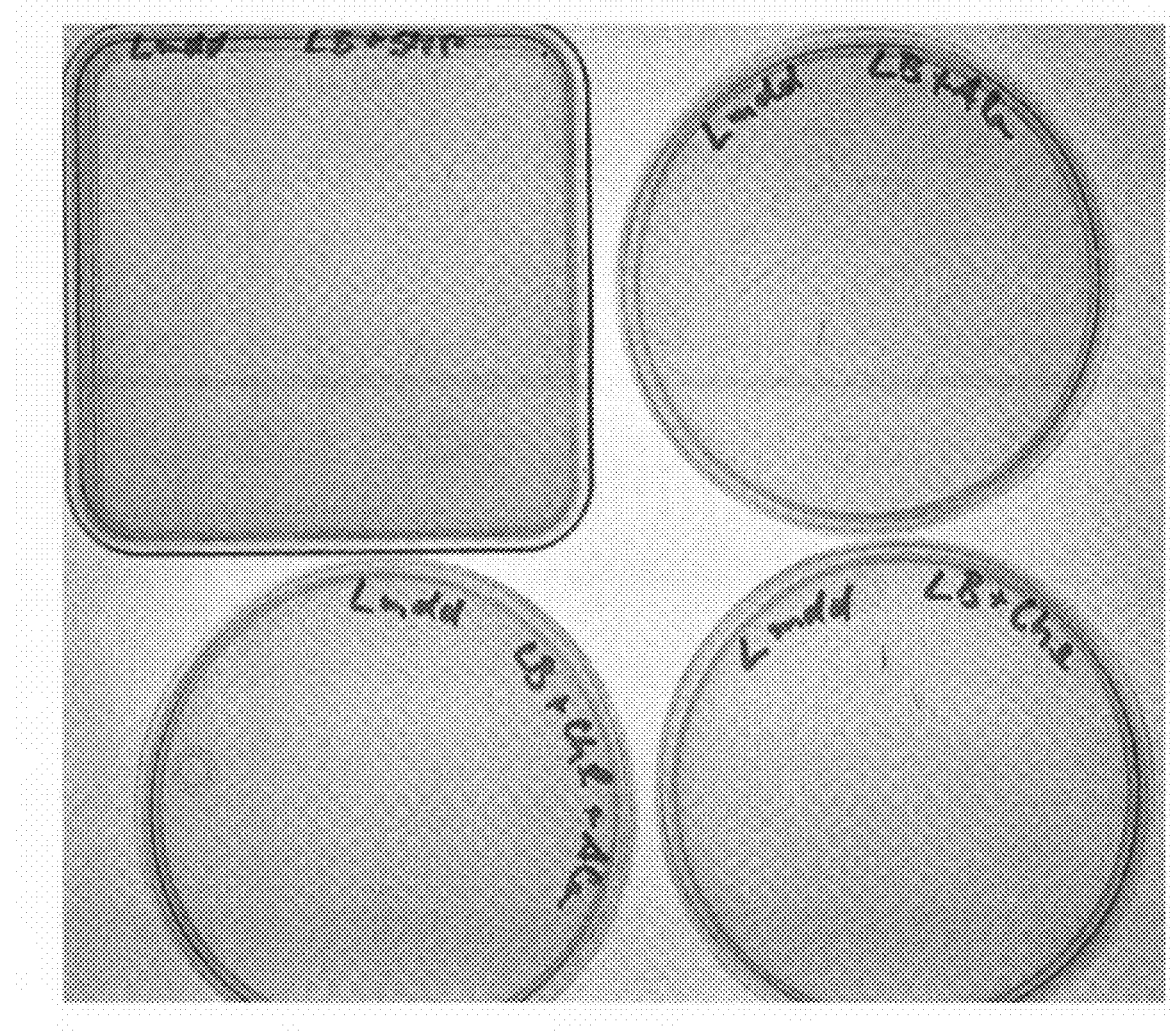
FIG. 7 depicts growth on LB-agar plates of LM strain Lmdd(−) without the pTV3 vector. Upper left: agar with streptomycin. Lmdd (−) cannot grow in the absence of d-alanine. Upper right: agar with alanine. Lmdd (−) grows. Lower left (agar with chloramphenicol and alanine) and lower right (agar with chloramphenicol): Lmdd(−) is sensitve to chloramphenicol and does not grow.

In addition, plasmid stability in vivo was tested in C57BL/6 mice by isolating viable bacteria at different time points after injection. Again, CFU counts on selective and nonselective plates were used to determine plasmid maintenance among the isolated bacteria (FIG. 3B). No differences in CFU were detected on selective and nonselective plates for each construct, indicating the stable presence of the recombinant plasmid in all bacteria isolated. Since viable Lmdd(pTV3) bacteria were isolated at least until day 5, plasmid loss in vivo followed by early clearance of injected bacteria could be excluded as explaining the level of virulence observed for Lmdd(pTV3) bacteria (Example 2).

In summary, pTV3 was stably maintained in *E. coli* as well as in *Listeria*, both in vitro and in vivo. Bacterial growth on LB media that was not supplemented with additional D-alanine indicated that the dal expression cassette was active also in gram-negative *E. coli*. Both *E. coli*-pTV3 and Lmdd-pTV3 remained sensitive to chloramphenicol, indicating the successful removal of both CAT genes from the plasmid. Representative plates are depicted in FIGS. 4-7.

The pTV3 copy number per cell was compared between Lm-LLOE7 in the presence of chloramphenicol and Lmdd-TV3 in the absence of chloramphenicol by real-time PCR of the E7 sequences, in both *Listeria* and *E. coli*. Lm-LLOE7 expresses LLO/E7 fusion protein from pGG55. Plasmid copy numbers of Lmdd-TV3 and Lm-LLOE7 did not significantly differ from one another, showing stable retention of plasmid pTV3 in both *Listeria* and *E. coli*.

Figure 8:
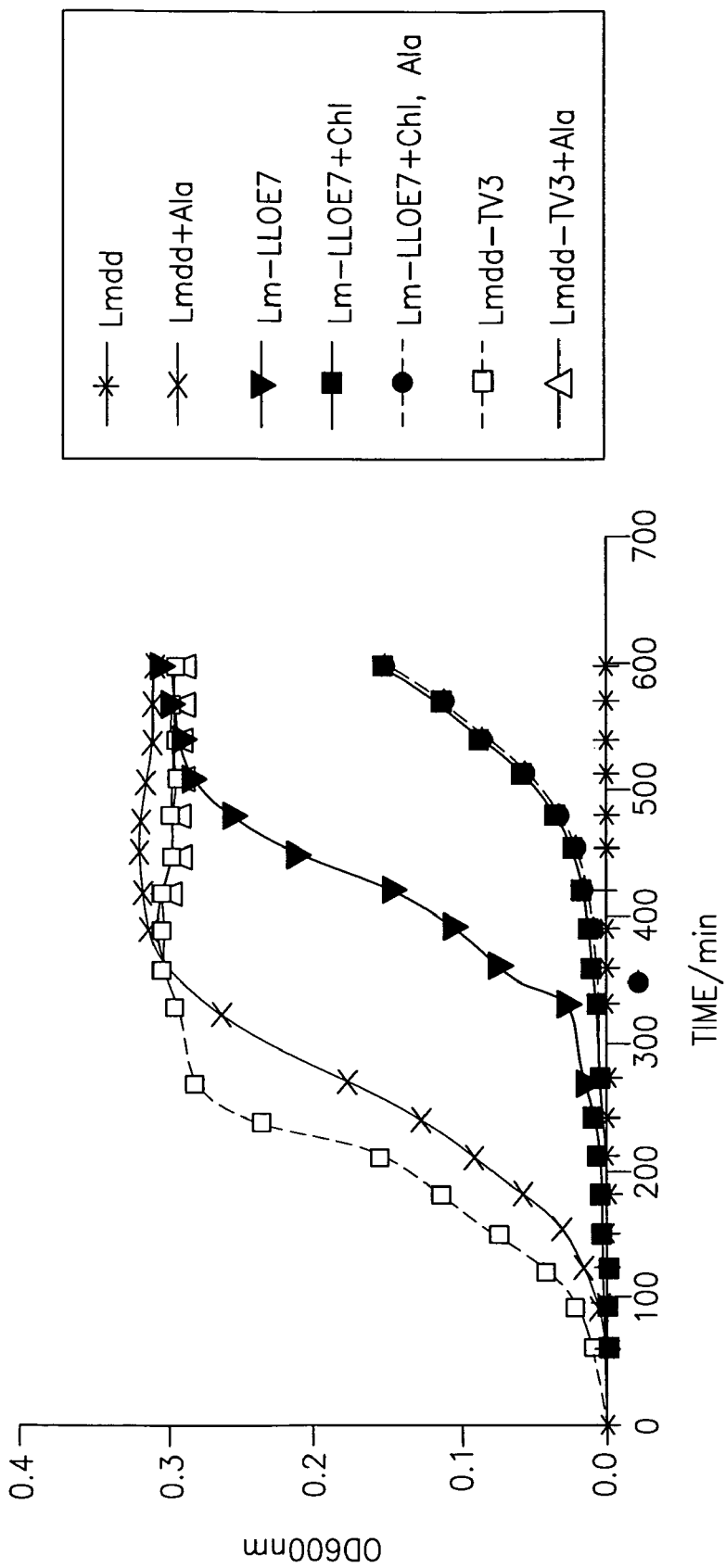
FIG. 8 depicts bacterial growth as measured by optical density (600 nanometers [nm]) plotted vs. time. +Ala: media contains D-alanine; +Chl: media contains chloramphenicol.

In order to verify the complementation of bacterial functions, in vitro growth kinetics were compared among Lmdd, Lmdd-TV3 and Lm-LLOE7. Lmdd-TV3, but not non-complemented Lmdd was able to grow in alanine-free media (FIG. 8). In fact, Lmdd-TV3 reached logarithmic growth phase sooner than both Lm-LLOE7 and Lmdd complemented with exogenous D-alanine. This growth attenuation of Lm-LLOE7 was partially due to the metabolic burden of CAT expression. However, even in the absence of chloramphenicol, Lm-LLOE7 still grew more slowly in vitro than Lmdd-TV3.

EXAMPLE 2

Plasmids Containing a Metabolic Enzyme do not Increase The Virulence of Bacteria Materials and Experimental Methods Hemolytic Lysis Assay $4×10^9$ CFU of *Listeria* were thawed, pelleted by centrifugation (1 minute, 14000 rpm) and resuspended in 100 μl PBS, pH 5.5 with 1 M cysteine. Bacteria were serially diluted 1:2 and incubated for 45 minutes at 37° C. in order to activate secreted LLO. Defibrinated total sheep blood (Cedarlane, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 μl of 10% washed blood cells were mixed with 100 μl of *Listeria* suspension and incubated for additional 45 minutes at 37° C. Un-lysed blood cells were then pelleted by centrifugation (10 minutes, 1000×g). 100 μl of supernatant was transferred into a new plate and the $OD_{530\ nm}$ was determined and plotted against the sample dilution.

Results

As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining $LD_{50}$ values, a more direct, and therefore accurate, means of measuring virulence. The $LD_{50}$ of Lmdd-TV3 ($0.75×10^9$) was very close to that of Lm-LLOE7 ($1×10^9$), showing that plasmids containing a metabolic enzyme do not increase the virulence of bacteria.

EXAMPLE 3

Vaccine Strains Carrying Plasmids Containing a Metabolic Enzyme Mediate Antigen Expression Antigen expression from the metabolic enzyme-containing plasmid was tested in vitro by Western blot. When analyzing equal amounts of total protein from bacterial culture supernatants, Lmdd-TV3 cultures contained approximately double the amount of total antigen than Lm-LLOE7 cultures. This difference may be a result of a higher overall metabolic load in Lm-LLOE7, due to the larger size of the plasmid (12.8 kB) compared to Lmdd-TV3 (7.6 kB).

Thus, metabolic enzymes can be used instead of antibiotic resistance genes to mediate plasmid retention in auxtrophic bacteria. Further, such plasmids have utility in expression of heterologous proteins in bacteria.

EXAMPLE 4

Induction of Anti-Tumor Immunity by Plasmids Containing a Metabolic Enzyme

Materials and Experimental Methods

Experimental Design $10^5$ TC-1 (ATCC, Manassas, Va.) were implanted subcutaneously in C57BL/6 mice (n=8) and allowed to grow for about 7 days, after which tumors were palpable. TC-1 is a C57BL/6 epithelial cell line that was immortalized with HPV E6 and E7 and transformed with activated ras, which forms tumors upon subcutaneous implantation. Mice were immunized with 0.1 $LD_{50}$ of the appropriate Listeria strain on days 7 and 14 following implantation of tumor cells. A non-immunized control group (naïve) was also included. Tumor growth was measured with electronic calipers.

Results

Figure 9:
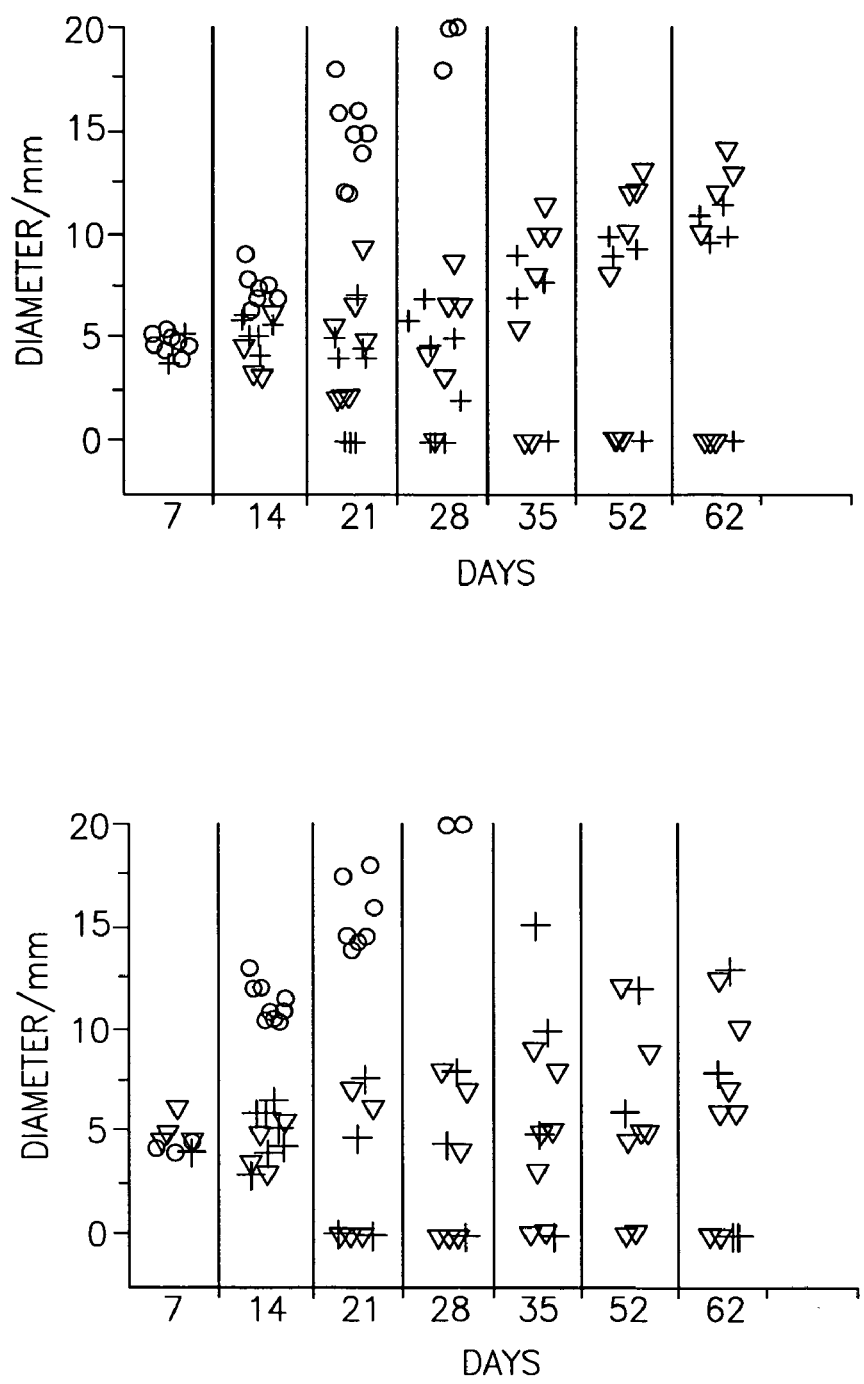
FIG. 9 depicts tumor regression in response to administration of LM vaccine strains (A). Circles represent naive mice, inverted triangles represent mice administered Lmdd-TV3, and crosses represent mice administered Lm-LLOE7.

Efficacy of the metabolic enzyme-containing plasmid as a cancer vaccine was determined in a tumor regression model. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 9) with no statistically significant difference ($p<0.05$) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

EXAMPLE 5

Plasmids Containing a Metabolic Enzyme Induce Antigen-Specific, Tumor Infiltrating T-Cells Materials and Experimental Methods T-Cell Analysis T-cells from spleen and tumor infiltrating T-cells were analyzed for CD8 and CD4 surface markers and E7 specificity according to standard protocols (Gunn et al. (2001, J. Immunol, 167: 6471-6479). C57BL/6 mice were immunized ip. 7 and 14 days after tumor implantation with Lmdd-TV3 or Lm-LLOE7. Splenocytes and tumors were harvested 5 days after the second injection, and were stained at room temperature with $H-2D^b$ tetramers loaded with the E7 peptide (RAHYNIVTF, SEQ ID NO: 18) or a control (HIV-Gag) peptide at a 1:200 dilution. Tetramers were provided by the National Institute of Allergy and Infectious Diseases Tetramer Core Facility and the National Institutes of Health AIDS Research and Reference Reagent Program.

Three-color flow cytometry for CD8 (53-6.7, PE conjugated), and E7H-2 $D^b$ tetramer was performed using a FAC-SCalibur® flow cytometer with CellQuest® software (Becton Dickinson, Mountain View, Calif.). Intracellular gamma interferon (IFN-) staining was performed on a second subset of cells. Before staining for the cell surface antigens and IFN-production, lymphocytes were stimulated in vitro by culturing in the presence of monensin (BD Biosciences) to accumulate intracellular IFN-γ in the Golgi apparatus. After culture for 5 hr in RP-10 supplemented with interleukin-2 (50 U/ml) and 1 µl of brefeldin A (monensin) per ml, the cells were surface stained for effector markers at 4° C. for 20 min with phycoerythrin-conjugated anti-CD8 (PharMingen) and antigen-presenting cell-conjugated MEL-14 (anti-CD62 ligand). Cells were gated on (selected for) CD62 ligand low to select activated cells before being analyzed for $CD8^+$ IFN-gamma$^+$ populations.

Results

Anti-tumor efficacy of a vaccine is often linked to its ability to induce antigen-specific, tumor-infiltrating lymphocytes. To further characterize Lmdd-TV3 efficacy, the tumor-infiltrating cytotoxic T-cells (CTL) for E7 antigen specificity were therefore analyzed. Both Lmdd-TV3 and Lm-LLOE7 induce a significant percentage of E7 tetramer specific T-cells infiltrating the tumor (Table 1). No significant differences were observed in the percentages of IFN-γ-producing $CD8^+$ T cells in L. monocytogenes LLO-E7-immunized mice versus Lmdd(pTV3)-treated mice. Thus, both Lmdd-TV3 and Lm-LLOE7 induced tumor infiltrating, antigen-specific CTL that controlled tumor growth.

TABLE 1

Cells were stained with anti-CD8- antibody and E7-tetramer and subjected to FACS analysis. After gating on (selecting) $CD8^+$/E7-tetramer$^+$/$CD62^-$, the percentage of $CD8^+$/E7-tetramer$^+$/$CD62^-$ cells from total live cells was calculated.

| | | Experiment A | | $CD8^+$, E7-tetramer$^+$, $CD62^-$ Experiment B | |
|---|---|---|---|---|---|
| Group | Dose | $CD8^+$, E7-tetramer$^+$ | $CD8^+$, IFN-gamma$^+$ | $CD8^+$, E7-tetramer$^+$ | $CD8^+$, IFN-gamma$^+$ |
| Naïve | 0 | 8.81 | 1.33 | 4.86 | 0.01 |
| Lmdd-TV3 | 0.75 × $10^8$ | 20.72 | 7.06 | 14.86 | 5.5 |
| Lm-LLOE7 | 1 × $10^8$ | 27.43 | 5.55 | 20.82 | 7.93 |

EXAMPLE 6

Generation of a Listeria Vaccine Vector Containing an Integrated Heterologous Gene, without the Use of an Antibiotic Resistance Gene Materials and Experimental Methods Generation of GG-L74

GG-L74 was created from Listeria strain 10403S by double allelic exchange at the orfZ domain, using a temperature-sensitive shuttle plasmid, as described in Gunn et al. (2001, J. Immunology 167: 6471-6479). GG-L74 was generated by introducing an expression cassette containing the hly-E7 fusion gene into the orfZ domain of the L. monocytogenes genome. The hly promoter drives the expression of the first 441 AA of the hly gene product, which is joined by the Xho1 site to the E7 gene. The result is a hly-E7 fusion gene that was transcribed and secreted as LLO-E7. The hly-E7 gene was ligated into the pKSV7 shuttle vector in the reverse orientation to avoid integration into the hly gene. The resulting plasmid, GG-L74, is an expression system that includes the previously described expression cassette inserted in the middle of a 1.6 Kb sequence that corresponds to the orfX, Y, Z domain of the *L. monocytogenes* genome. *L. monocytogenes* strain 10403S was transformed with pGG-74. The homology domains allow for insertion of the LL0-E7 gene cassette into the or orfZ domain by homologous recombination as described in Gunn et al. (2001, J. Immunology 167: 6471-6479). Clones were screened for integration of the LL0-E7 gene cassette into the orfZ domain.

Results

A *Listeria* vaccine vector, GG-L74, expressing a fusion of a non-hemolytic LLO fragment to the E7 antigen of human papilloma virus from the *Listeria* chromosome was produced by transfecting Lmdd with an hly-E7 fusion expression cassette, using p60-dal as the selectable marker. GGL74 has an $LD_{50}$ in mice of $10^6$ CFU.

EXAMPLE 7

Chromosomal Integration of Recombinant Genes Based on Phage Integration System

Materials and Experimental Methods

Construction of pTV6-11
  pTV6-1 are constructed from pPL1 or pPL2 as follows: First, pPL1 and pPL2 will be described:
pPL1
  pPL1 has the sequence:

(SEQ ID No: 19; GenBank Accession No. AJ417488)

```
gacgtcattaaccctcactaaagggaacaaaagctgggtaccgggccccccctcgaggtcgacggtatcgataagcttgatatcgaattcctgcagcccggg ggatccactagttctagagcggccgccaccgcggtggagctccaattcgccctatagtgagtcgtattgacgtcgctatttaacgaccctgccctgaaccga cgaccgggtcgaatttgctttcgaatttctgccattcatccgcttattatcacttattcaggcgtagcaccaggcgtttaagggcaccaataactgccttaa aaaaattacgccccgccctgccactcatcgcagtactgttgtaattcattaagcattctgccgacatggaagccatcacagacggcatgatgaacctgaatc gccagcggcatcagcaccttgtcgccttgcgtataatatttgcccatggtgaaaacggggcgaagaagttgtccatattggccacgtttaaatcaaaactg gtgaaactcacccagggattggctgagacgaaaaacatattctcaataaacccttagggaaataggccaggttttcaccgtaacacgccacatcttgcgaa tatatgtgtagaaactgccggaaatcgtcgtggtattcactccagagcgatgaaaacgtttcagtttgctcatgaaaacggtgtaacaagggtgaacacta tcccatatcaccagctcaccgtctttcattgccatacggaattccggatgagcattcatcaggcgggcaagaatgtgaataaaggccggataaaacttgtgc ttattttctttacggtctttaaaaaggccgtaatatccagctgaacggtctggtatataggtacattgagcaactgactgaaatgcctcaaaatgttcttta cgatgccattgggatatatcaacggtggtatatccagtgatttttttctccatttttagcttccttagctcctgaaaatctcgataactcaaaaaatacgccc ggtagtgatcttatttcattatggtgaaagttggaacctcttacgtgccgatcaacgtctcattttcgccaaaagttggcccagggcttcccggtatcaaca gggacaccaggatttatttattctgcgaagtgatcttccgtcacaggtatttattcggcgcaaagtgcgtcgggtgatgctgccaacttactgatttagtgt atgatggtgttttttgaggtgctccagtggcttctgtttctatcagctgtccctcctgttcagctactgacggggtggtgcgtaacggcaaaagcaccgccgg acatcagcgctagcggagtgtatactggcttactatgttggcactgatgagggtgtcagtgaagtgcttcatgtggcaggagaaaaaggctgcaccggtgc gtcagcagaatatgtgatacaggatatattccgcttcctcgctcactgactcgctacgctcggtcgttcgactgcggcgagcggaaatggcttacgaacggg gcggagatttcctggaagatgccaggaagatacttaacagggaagtgagagggccgcggcaaagccgttttccataggctccgcccccctgacaagcatca cgaaatctgacgctcaaatcagtggtggcgaaacccgacaggactataaagataccaggcgtttccccctggcggctccctcgtgcgctctcctgttcctgc ctttcggtttaccggtgtcattccgctgttatggccgcgtttgtctcattccacgcctgacactcagttccgggtaggcagttcgctccaagctggactgta tgcacgaaccccccgttcagtccgaccgctgcgccttatccggtaactatcgtcttgagtccaacccggaaagacatgcaaaagcaccactggcagcagcca ctggtaattgatttagaggagttagtcttgaagtcatgcgccggttaaggctaaactgaaaggacaagttttggtgactgcgctcctccaagccagttacct cggttcaaagagttggtagctcagagaaccttcgaaaaaccgccctgcaaggcggttttttcgttttcagagcaagagattacgcgcagaccaaaacgatct caagaagatcatcttattaatcagataaaatatttctagatttcagtgcaatttatctcttcaaatgtagcacctgaagtcagccccatacgatataagttg taattctccgccgcttgccctcatctgttacgccggcggtagccggccagcctcgcagagcaggattcccgttgagcaccgccaggtgcgaataagggacag tgaagaaggaacaccgctcgcgggtgggcctacttcacctatcctgcccggctgacgccgttggatacaccaaggaaagtctacacgaacccttggcaaa atcctgtatatcgtgcgaaaaggatggatattccgaaaaaatcgctataatgaccccgaagcagggttatgcagcggaaagcgctgcttccctgctgttt tgtggaatatctaccgactggaaacaggcaaatgcaggaaattactgaactgaggggacaggcgagaggcatgcgataaaaagcaatctatagaaaaacagg ttacttttttatttataattttagtttctcgattcgtttccgtccaacgagagaaaacgaggaactaaacaatctaaataaacaagctactagagccattcaa tagtaacttgttcaccgtcaatataaattttattaattagtgattttaaataaagttgcttttctcggaactctaaagagtcaaaatcaactgttgctaaat
```

-continued

```
cagctaaattttcttgtatcttttttattttttcttcaattcttcgttagcttctatttgtgcttcataataattaatttgagcatcgatatcagccatcatag catcaagttctgaaacttcgtaagaaccgctgatatataaatcaaatagccgtttctttttttacgtgttctgttttaagttttcatttaagctatctaatt cgtcttctttatctacattcctagaagcgaaactatagttattcacgcgatcaataattaattcctcgagtttgtcagctctccaaattttatttccacatt tttctagttcatgagtatgtttgtaagtcttgcaactataatatctataatgatattttttccgcgggaaacagtatcttttctccgatgaacaaaaccca acccacattttccacacactaccaaattatttagcaacgatgctgaatctctattcatatttggattttttacccatgcgagaaaaaatttcttgaactcgat aaaattgttcctctgaaataataggctcatgaacacctttgtatgcactttatccgcataagatacataaccacagtataaatcattagttagccaattgt tgtaactgctatatgatttcactttgaatcctaattttttagtctcttctgtaaagtggtaatgcttttttcttcctcaaaaatatcataaatcatttgta attgttttgcttcttcttcattaatatataatttagtatctataacatcatagccgaatgttctacctttgcagtcgttaaaggaagacctgcttcaatac gcttaattttccccatcaccatacgatcacgtatagtttcgcgctctaattgagcaaatacggataatataccaatcatcgcgcgcccaaatgggctagagg tgtcaagagtttcagacaaactaacaaattctacattgtttttaagaagtattcttcaataagcgttatcgtatctctttgtgagcgggaaagtctatcta agcgatatacaacaacagcatcaatttcatgtaatttacttagcatttcatttagtgcggggcgattcatgtttgaaccgctgtatccgccgtctatgaaaa tatcgtatacgtcccaatccttcgagcggcacaaggctgttagcttttcagtttgagcttgtatagagtaattctctatttgttcttgagtagatacgcgta tataaatagctgccttcatttccgttctcctctcgcatggaaagttaagatcttttttcagaaaatcccagtacgtaattaagtatttgagaattaatttt atattgattaatactaagtttacccagttttcacctaaaaaacaaatgatgagataatagctccaaaggctaaagaggactataccaactatttgtaataat tctgtaacagttgaaaagcgaacgtgtattcttagggcttgagatgtattgctgggtaaaccttatagtgtaagtgggatgtgaacgttaatcaacaactt tcgctatgggaaacctattgttttttgttaatagaaaaacttaatacatttgtaatataaaaaccggcagttttccgttcttcgtgactcgaaatgaattg ccagatgagtttatggtattctataatagaaggtatggaggatgttatataatgagacagaattatgatgatcgaaagctagcttggcactggccgtcgttt tacaacgtcgtgactgggaaaaccctggcgttacccaacttaatcgccttgcagcacatccccctttcgccagctggcgtaatagcgaagaggcccgcaccg atcgcccttcccaacagttgcgcagcctgaatggcgaatggcgcctgatgcggtattttctccttacgcatctgtgcggtatttcacaccgcatatgatccc ggatctggagctgtaatataaaaaccttcttcaactaacggggcaggttagtgacattagaaaaccgactgtaaaaagtacagtcggcattatctcatatta taaaagccagtcattaggcctatctgacaattcctgaatagagttcataaacaatcctgcatgataaccatcacaaacagaatgatgtacctgtaaagatag cggtaaatatattgaattacctttattaatgaattttcctgctgtaataatgggtagaaggtaattactattattattgatattttaagttaaacccataaa tgaagtccatggaataatagaaagagaaaaagcattttcaggtataggtgttttgggaaacaatttccccgaaccattatatttctctacatcagaaaggta taaatcataaaactctttgaagtcattctttacaggagtccaaataccagagaatgttttagatacaccatcaaaaattgtataaagtggctctaacttatc ccaataacctaactctccgtcgctattgtaaccagttctaaaagctgtatttgagtttatcacccttgtcactaagaaaataaatgcagggtaaaatttata tccttcttgttttatgtttcggtataaaacactaatatcaatttctgtggttatactaaaagtcgtttgttggttcaaataatgattaaatatctcttttct cttccaattgtctaaatcaatttttattaaagttcatttgatatgcctcctaaattttatctaaagtgaatttaggaggcttacttgtctgctttcttcatt agaatcaatcctttttaaaagtcaatattactgtaacataaatatattttaaaaatatcccactttatccaattttcgtttgttgaactaatgggtgct ttagttgaagaataaaagaccacattaaaaaatgtggtcttttgtgtttttttaaaggatttgagcgtagcgaaaaatccttttctttcttatcttgataat aagggtaactattgcccagatccgggatcatatggtgcactctcagtacaatctgctctgatgccgcatagttaagccagccccgacaccccgccaacacccg ctgacgcgccctgacgggcttgtctgctcccggcatccgcttacagacaagctgtgaccgtctccgggagctgcatgtgtcagaggttttcaccgtcatcac cgaaacgcgcgagacgaaagggcctcgtgatacgcctatttttataggttaatgtcatgataataatggtttctta.
``` bp 1 to 171 of pPL1 contain the multiple cloning site from pBluescript KS (Alting-Mees, M A, and Short J M. 1989. pBluescript II: gene mapping vectors. Nucleic Acids Res. 17: 9494), and were subcloned using the primers 5'-GGACGT-CATTAACCCTCACTAAAGG-3' (SEQ ID No: 20) and 5'-GGACGTCAATACGACTCACTATAGG-3' (SEQ ID No: 21).

bp 172 to 2253 contain the low-copy-number gram-negative origin of replication and chloramphenicol acetyltransferase (CAT) gene from pACYC 184 (Chang, A C et al, 1978. Construction and characterization of amplifiable multicopy DNA cloning vehicles derived from the P15A cryptic miniplasmid. J. Bacteriol. 134:1141-1156), and were cloned after PCR with primers 5'-GGACGTCGCTATTTAACGAC-CCTGC-3' (SEQ ID No: 22) and 5'-GAGCTGCAG-GAGAATTACAACTTATATCGTATGGGG-3' (SEQ ID No: 23).

bp 2254 to 2624 contain the RP4 origin of transfer (oriT) (Pansegrau, W E et al, 1994. Complete nucleotide sequence of Birmingham IncP alpha plasmids. Compilation and comparative analysis. J. Mol. Biol. 239:623-663) (for use in direct conjugation from *E. coli* to *L. monocytogenes*), and was cloned from plasmid pCTC3 (Williams, D R et al, 1990. Conjugative plasmid transfer from *Escherichia coli* to *Clostridium acetobutylicum*. J. Gen. Microbiol. 136:819-826) after PCR with primers 5'-GCACTGCAGC- CGCTTGCCCTCATCTGTTACGCC-3' (SEQ ID No: 24) and 5'-CATGCATGCCTCTCGCCTGTCCCCT-CAGTTCAG-3' (SEQ ID No: 25).

bp 2629 to 4127 contain the listeriophage U153 integrase gene and attachment site (attPP') (Gen Bank Accession Number AJ417489) that direct the site-specific integration of the plasmid, and were cloned after PCR with primers 5'-GTA-GATCTTAACTTTCCATGCGAGAGGAG-3' (SEQ ID No: 28) and 5'-GGGCATGCGATAAAAAGCAATCTATA-GAAAAACAGG-3' (SEQ ID No: 29).

bp 4134 to 4563 contain the LM p60 promoter, used to drive expression of the U153 integrase gene, (Kohler, S M et al, 1990. The gene coding for protein p60 of *Listeria monocytogenes* and its use as a specific probe for *Listeria monocytogenes*. Infect. Immun. 58:1943-1950), and were PCR amplified with primers 5'-CCTAAGCTTTCGATCATCAT-AATTCTGTC-3' (SEQ ID No: 30) and 5'-GGGCATGCA-GATCTTTTTTTCAGAAAATCCCAGTACG-3' (SEQ ID No: 31) and cloned upstream of the integrase gene.

bp 4570 to 6101 contain a HindIII-AatII restriction fragment subcloned from pUC18-Cat (obtained from Nancy Freitag, University of Washington), which in turn contains (bp 4788 to 5850) the inducible gram-positive CAT gene from pC194 (Horinouchi, S, and Weisbium, B, 1982. Nucleotide sequence and functional map of pC194, a plasmid that specifies inducible chloramphenicol resistance. J. Bacteriol. 150: 815-825).

Cloning of the hly and actA Genes into pPL1

Figure 10A:
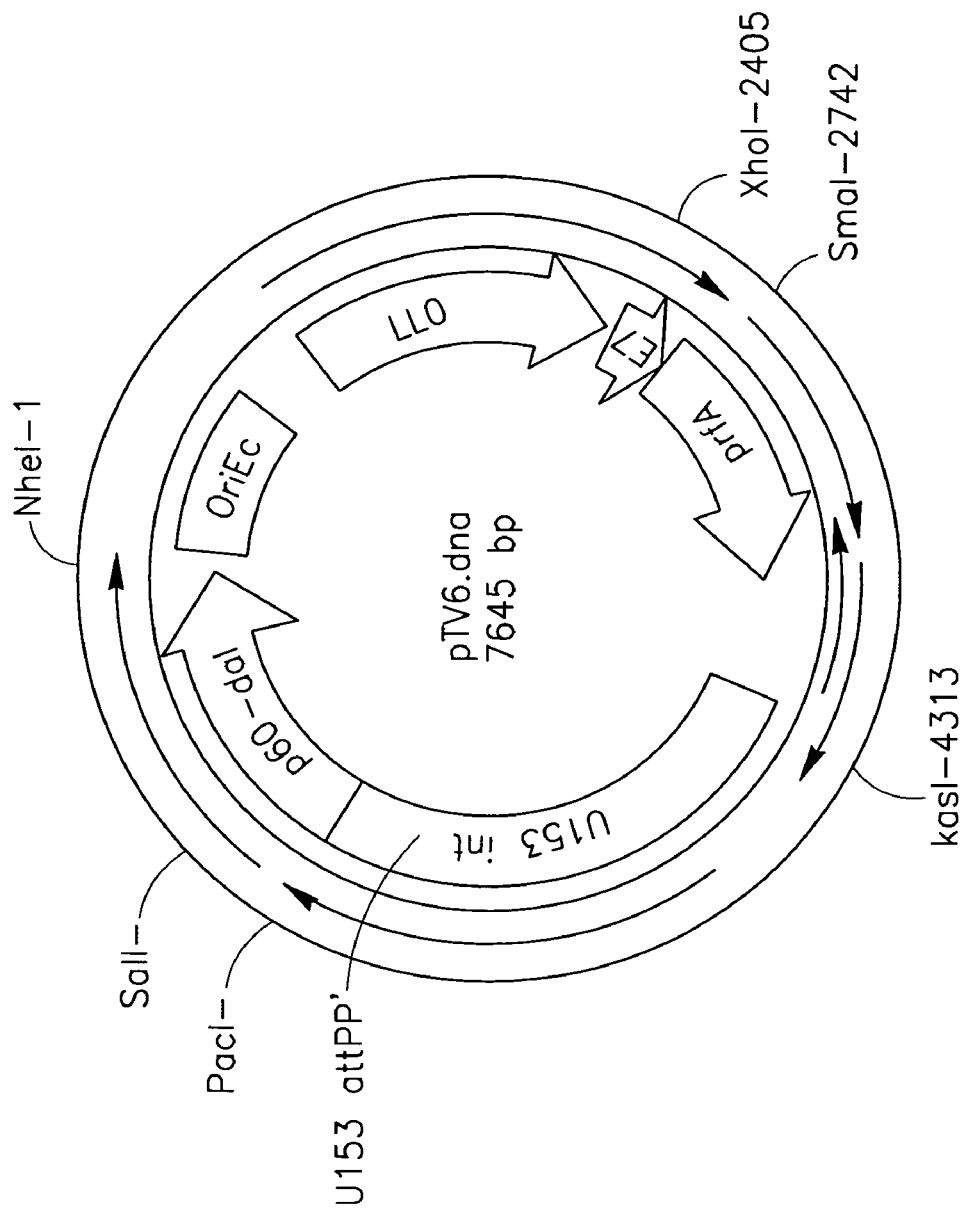
FIG. 10 A. Map of pTV6. B. Map of pTV7.
Figure 10B:
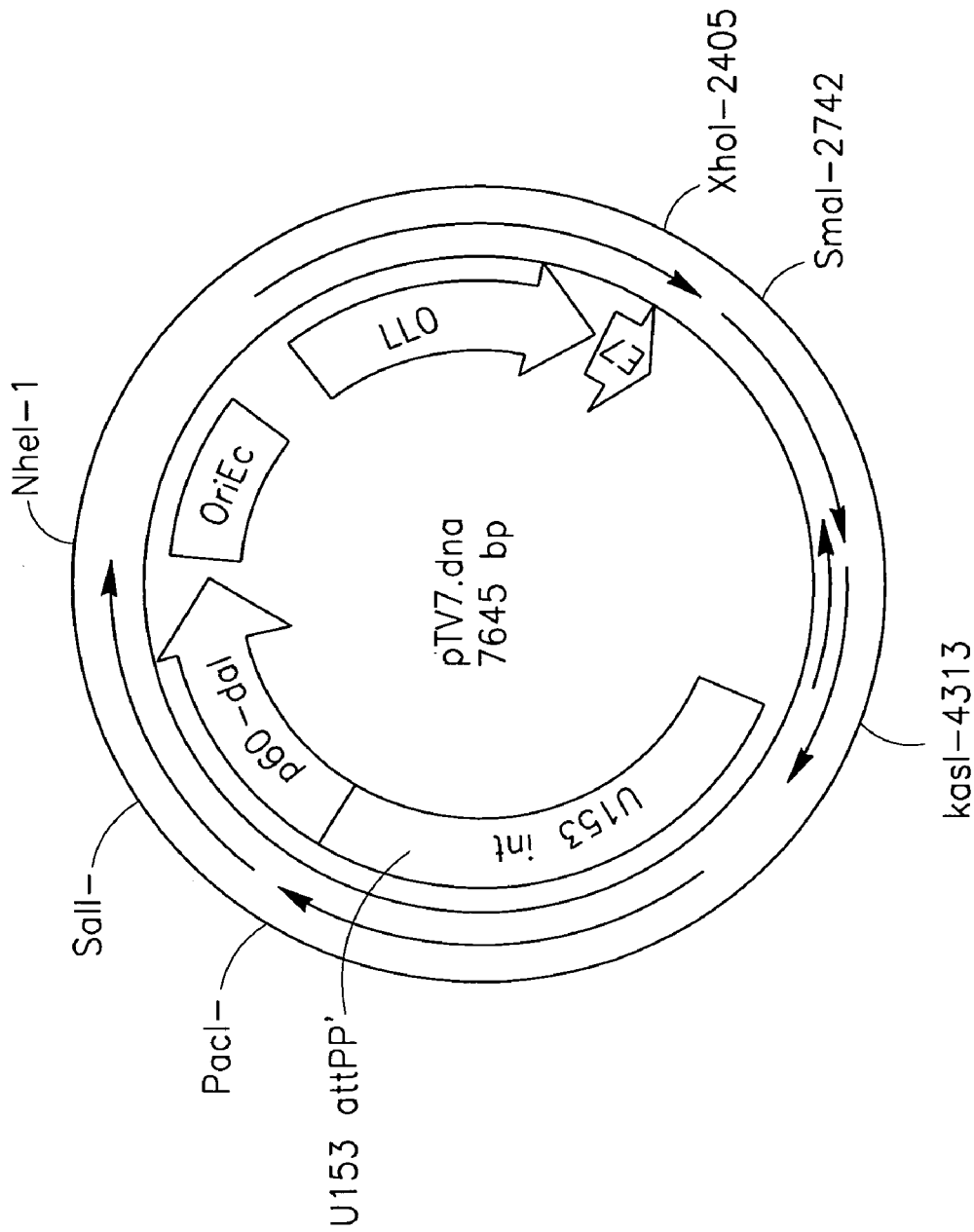

The hly gene was subcloned from plasmid pDP-906 (Jones, S et al. 1994. Characterization of *Listeria monocytogenes* pathogenesis in a strain expressing perfringolysin O in place of listeriolysin O. Infect. lmmun. 62: 5608-5613) by restriction digestion with BamHI and XbaI, gel purifying a 2.9-kb fragment, and ligating it into pPL1 cut with BamHI and SpeI (pPL24). The actA gene was PCR amplified from 10403S genomic DNA with primers 5'-GGTCTAGAT-CAAGCACATACCTAG-3' (SEQ ID No: 54) and 5'-CGG-GATCCTGAAGCTTGGGAAGCAG-3' (SEQ ID No: 55). The 2220 by PCR product was gel purified, cut with BamHI and XbaI, and clonedinto pPL1 cut with BamHI and SpeI (pPL25).

pPL2 pPL2 (FIG. 10B) has the sequence:

(SEQ ID No: 32)
```
gacgtcattaaccctcactaaagggaacaaaagctggtaccgggccccccctcgaggtcgacggtatcgataagcttgatatcgaattcctgcagcccgggg
gatccactagttctagagcggccgccaccgcggtggagctccaattcgccctatagtgagtcgtattgacgtcgctatttaacgaccctgccctgaaccgac
gaccgggtcgaatttgctttcgaatttctgccattcatccgcttattatcacttattcaggcgtagcaaccaggcgtttaagggcaccaataactgccttaa
aaaaattacgccccgccctgccactcatcgcagtactgttgtaattcattaagcattctgccgacatggaagccatcacaaacggcatgatgaacctgaatc
gccagcggcatcagcaccttgtcgccttgcgtataatatttgcccatggtgaaaacggggcgaagaagttgtccatattggccacgtttaaatcaaaactg
gtgaaactcacccagggattggctgagacgaaaaacatattctcaataaacccttagggaaataggccaggttttcaccgtaacacgccacatcttgcgaa
tatatgtgtagaaactgccggaaatcgtcgtggtattcactccagagcgatgaaaacgtttcagtttgctcatggaaaacggtgtaacaagggtgaacacta
tcccatatcaccagctcaccgtctttcattgccatacggaattccggatgagcattcatcaggcgggcaagaatgtgaataaaggccggataaaacttgtgc
ttattttttctttacggtctttaaaaaggccgtaatatccagctgaacggtctggttataggtacattgagcaactgactgaaatgcctcaaaatgttcttta
cgatgccattgggatatatcaacggtggtatatccagtgattttttttctccattttagcttccttagctcctgaaaatctcgataactcaaaaaatacgccc
ggtagtgatcttatttcattatggtgaaagttggaacctcttacgtgccgatcaacgtctcattttcgccaaaagttggcccagggcttcccggtatcaaca
gggacaccaggatttatttattctgcgaagtgatcttccgtcacaggtatttattcggcgcaaagtgcgtcgggtgatgctgccaacttactgatttagtgt
atgatggtgttttgaggtgctccagtggcttctgtttctatcagctgtccctcctgttcagctactgacggggtggtgcgtaacggcaaaagcaccgccgg
acatcagcgctagcggagtgtatactggcttactatgttggcactgatgagggtgtcagtgaagtgcttcatgtggcaggagaaaaaaggctgcaccggtgc
gtcagcagaatatgtgatacaggatatattccgcttcctcgctcactgactcgctacgctcggtcgttcgactgcggcgagcggaaatggcttacgaacggg
gcggagatttcctggaagatgccaggaagatacttaacagggaagtgagagggccgcggcaaagccgttttttccataggctccgcccccctgacaagcatca
cgaaatctgacgctcaaatcagtggtggcgaaacccgacaggactataaagataccaggcgtttccccctggcggctccctcgtgcgctctcctgttcctgc
ctttcggtttaccggtgtcattccgctgttatggccgcgtttgtctcattccacgcctgacactcagttccgggtaggcagttcgctccaagctggactgta
tgcacgaaccccccgttcagtccgaccgctgcgccttatccggtaactatcgtcttgagtccaacccggaaagacatgcaaaagcaccactggcagcagcca
ctggtaattgatttagaggagttagtcttgaagtcatgcgccggttaaggctaaactgaaaggacaagttttggtgactgcgctcctccaagccagttacct
cggttcaaagagttggtagctcagagaaccttcgaaaaaccgccctgcaaggcggttttttcgttttcagagcaagagattacgcgcagaccaaaacgatct
caagaagatcatcttattaatcagataaaatatttctagatttcagtgcaatttatctcttcaaatgtagcacctgaagtcagcccccatacgatataagttg
taattctccgccgcttgccctcatctgttacgccggcggtagccggccagcctcgcagagcaggattcccgttgagcaccgccaggtgcgaataagggacag
tgaagaaggaacacccgctcgcgggtgggcctacttcacctatcctgcccggctgacgccgttggatacaccaaggaaagtctacacgaacccttttggcaaa
atcctgtatatcgtgcgaaaaggatggatataccgaaaaaatcgctataatgacccccgaagcagggttatgcagcggaaaagcgctgcttccctgctgttt
```

-continued
```
tgtggaatatctaccgactggaaacaggcaaatgcaggaaattactgaactgaggggacaggcgagaggcatgcgtggagggaaagaagaacgctgttgaaa
aaatcttctctggactacttgaaacaaaagaattaaagtcattttataaaaaccttgagaaaaaacatcttgatataaaaactatttataacgaatatttat
ttcaatgtaataataaataatatttattattacataaaatgtttgtggtattatttgtggtatatatatcctaaatggctttatatcagtgtgtgttaatcc
ctctcaggacgttaaatagtaatgtaaagaaatctctaaaacgttgaaaagccttgatattaaagggcggatgaatgttttggagttttttttatatcgtat
aatacccgttttattccgttgttttttgtggcatttgtggtaaaatttgtggtattttcatctgttttagtgtgaaaaaagcatctactttggactgattat
gttgtcttaaattagagcttagatgactatagtgatttttaatgttgtattaatgtcatcatgaccaagcctatcagctacataaataatatccatacccgctt
ctacacataagcctgtatgcgtatgtcgtagcttgtgtaatgtcactggttcagaattgattgtactacatatcttcttcaaagctttattacaagacgcgt
tgtctactggcttattgtggtaagtgatgaataataacatcaatggattcttaatagcatgttccttcatatattcagtatgccaatttaaatacgaatgta
aatattgagcggtagagttatcaatatagatcactcgtgatttttttgttttggtatcaatgaatgtattagtgtacttgtaatcccaagctttattcacag
ttattgaacgtttagtgaaattaatatccttctttgttagtgcaataatttcttcgaacctcatgcctgtctggacagctagaaagataactgctcgtgata
tagaatgaaattttgcaagttcttctaatagtaaatgaactttgtctgtttccataaattgtgctttattttttcgctacgtcctgtccgcttatatgagccc
ctatagtggggttttttcttcatgtaacctaaatgaacagccttgttaaaaatcgctctaattttgcggtgtctggtgtctacagtggatattgcatagtcta
cagataaatgattaataaattgttgatattgaaccgcatcaatcgaattaaattttaatttttttcatcgaaataatcaacgaattgattataagcaagatcgt
ataaattaatagtgattgactacttttccatcttaaatgttttcatgaatagcgtataaaattctttgaagttccattcttcagagaactactatcat
gctgaacttgttttaataatttagatgcttatacattaagtttgtttcacttgtatctgtcaaacgcttttctttccattcaccatcgacttttatacgta
ggcgaacacaatatttaccgtttgctaattttttttatcttcattaataccaccacctgtttattttttggagatctttttttcagaaaatcccagtacgtaat
taagtatttgagaattaattttatattgattaatactaagtttacccagttttcacctaaaaaacaaatgatgatataatagctccaaaggctaaagaggac
tataccaactatttgtaataattctgtaacagttgaaaagcgaacgtgtattcttagggcttgagatgtattgctgggtaaacctttatagtgtaagtggga
tgtgaacgttaatcaacaactttcgctatgggaaacctattgtttttttgttaatagaaaaacttaatacatttgtaatataaaaaccggcagttttccgtt
cttcgtgactcgaaatgaattgccagatgagtttatggtattctataatagaaggtatggaggatgttatataatgagacagaattatgatgatcgaaagct
agcttggcactggccgtcgttttacaacgtcgtgactgggaaaaccctggcgttacccaacttaatcgccttgcagcacatcccccttcgccagctggcgt
aatagcgaagaggcccgcaccgatcgcccttcccaacagttgcgcagcctgaatggcgaatggcgcctgatgcggtattttctccttacgcatctgtgcggt
atttcacaccgcatatgatcccggatctggagctgtaatataaaaaccttcttcaactaacggggcaggttagtgacattagaaaaccgactgtaaaagta
cagtcggcattatctcatattataaaagccagtcattaggcctatctgacaattcctgaatagagttcataaacaatcctgcatgataaccatcacaaacag
aatgatgtacctgtaaagatagcggtaaatatattgaattaccctttattaatgaattttcctgctgtaataatgggtagaaggtaattactattattattga
tatttaagttaaacccagtaaatgaagtccatggaataatagaaagagaaaaagcattttcaggtataggtgttttgggaaacaatttccccgaaccattat
atttctctacatcagaaaggtataaatcataaaactctttgaagtcattcttacaggagtccaaataccagagaatgttttagatacaccatcaaaaattg
tataaagtggctctaacttatcccaataacctaactctccgtcgctattgtaaccagttctaaaagctgtatttgagtttatcaccttgtcactaagaaaa
taaatgcagggtaaaatttatatccttcttgttttatgtttcggtataaaacactaatatcaatttctgtggttatactaaaagtcgtttgttggttcaaat
aatgattaaatatctcttttctcttccaattgtctaaatcaattttattaaagttcatttgatatgcctcctaaattttatctaaagtgaatttaggaggc
ttacttgtctgctttcttcattagaatcaatcctttttaaagtcaatattactgtaacataaatatatttttaaaaatatcccactttatccaattttc
gtttgttgaactaatgggtgctttagttgaagaataaaagaccacattaaaaaatgtggtcttttgtgtttttttaaaggatttgagcgtagcgaaaaatcc
ttttctttcttatcttgataataagggtaactattgcccagatccgggatcatatggtgcactctcagtacaatctgctctgatgccgcatagttaagccag
ccccgacacccgccaacacccgctgacgcgccctgacgggcttgtctgctcccggcatccgcttacagacaagctgtgaccgtctccgggagctgcatgtgt
cagaggttttcaccgtcatcaccgaaacgcgcgagacgaaagggcctcgtgatacgcctatttttataggttaatgtcatgataataatggtttctta.
```

To construct pPL2, the PSA attachment site (tRNA$^{arg}$-attBB') DNA sequence was obtained through a combination of inverse PCR and genome walking. Inverse PCR was performed on Sau3AI-digested DP-L4061 DNA (WSLC 1042, lysogenic for PSA; GenBank Accession No: AJ314913) with the divergent primers PL95 (5'-ACATAATCAGTCCAAAG-TAGATGC; SEQ ID No: 33) and PL97 (5'-ACGAATG-TAAATATTGAGCGG; SEQ ID No: 34), which anneal within the PSA int gene. The (5'-GAAGATCTCCAAAAATAAACAGGTGGTGG; SEQ ID No: 71) and PL101 (5'-CATGCATGCGTGGAGG-GAAAGAAGAACGC; SEQ ID No: 35) with Vent DNA polymerase, digested with BglII and SphI, and ligated to pPL1 that had been digested with the same enzymes, generating pPL2.

The DNA sequence of the PSA tRNA$^{Arg}$-attBB' from serotype 1/2 *L. monocytogenes* strains was obtained by a plasmid trap strategy. DP-L4211 (pPL2 integrated in 10403S) genomic DNA was digested with Nsi I and NheI, which do not cleave in the vector, and ligated under dilute conditions to promote self-ligation. The ligations were transformed into *E. coli* XL1-Blue, and chloramphenicol-resistant colonies were selected. The plasmids obtained were sequenced with the convergent primers PL94 (5'-GGAGGGAAAGAA-GAACGC; SEQ ID No: 36) and PL95 (SEQ ID No: 33) for attPB' and attBP', respectively, which flank attPP' in the PSA genomic DNA sequence. A serotype ½-specific PCR assay across tRNA$^{Arg}$-attBB' was developed from the 10403S DNA sequence and used to determine the prophage status of various LM strains. Primers PL102 (5'-TATCAGACCTAAC-CCAAACCTTCC; SEQ ID No: 37) and PL103 (5'-AATCG-CAAAATAAAAATCTTCTCG; SEQ ID No: 38) specifically amplify a 533-bp PCR product in nonlysogenic serotype ½ strains. The primer pair NC16 (5'-GTCAAAACAT-ACGCTCTTATC; SEQ ID No: 39) and PL95 specifically amplify a 499-bp PCR product in strains that either are lysogenic or contain an integration vector at tRNA$^{Arg}$-attBB'.

Construction of pTV6-7

Figure 11:
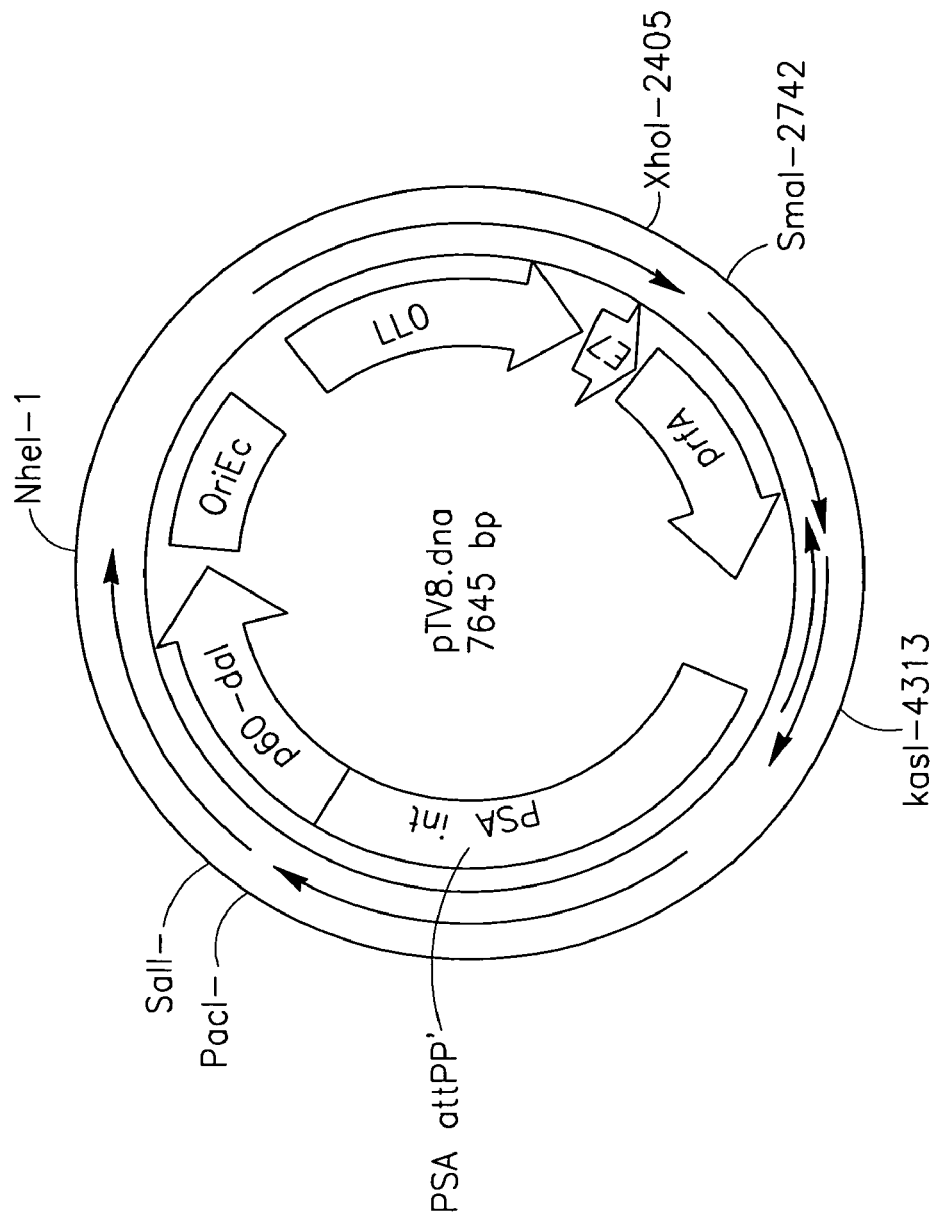
FIG. 11 Map of pTV8.

The U153 integrase gene and the U153 attPP' integration site from pPL1 are modified by PCR to contain restriction sites at the 5'-end and the 3'-end that are compatible with cloning these nucleic acids into shuttle plasmid pTV3. The *Listeria* replication region from pTV3 is removed, resulting in plasmid pTV6 (FIG. 11A). This plasmid contains replication functions for its amplification in *E. coli*, a dal gene for complementation of dal auxotroph *E. coli* and *Listeria*, and integration functions (U153 integrase, attPP' site) for integration of the plasmid into the *Listeria* genome. pTV6 also contains a prfA (pathogenicity regulating factor A) gene. This gene is not necessary for the function of pTV6, but can be used in situations wherein an additional selected marker in the plasmid or the integration vector is required or desired. In other experiments, a similar plasmid lacking the prfA gene is utilized (pTV7; FIG. 11B).

Construction of pTV8-9

Figure 12:
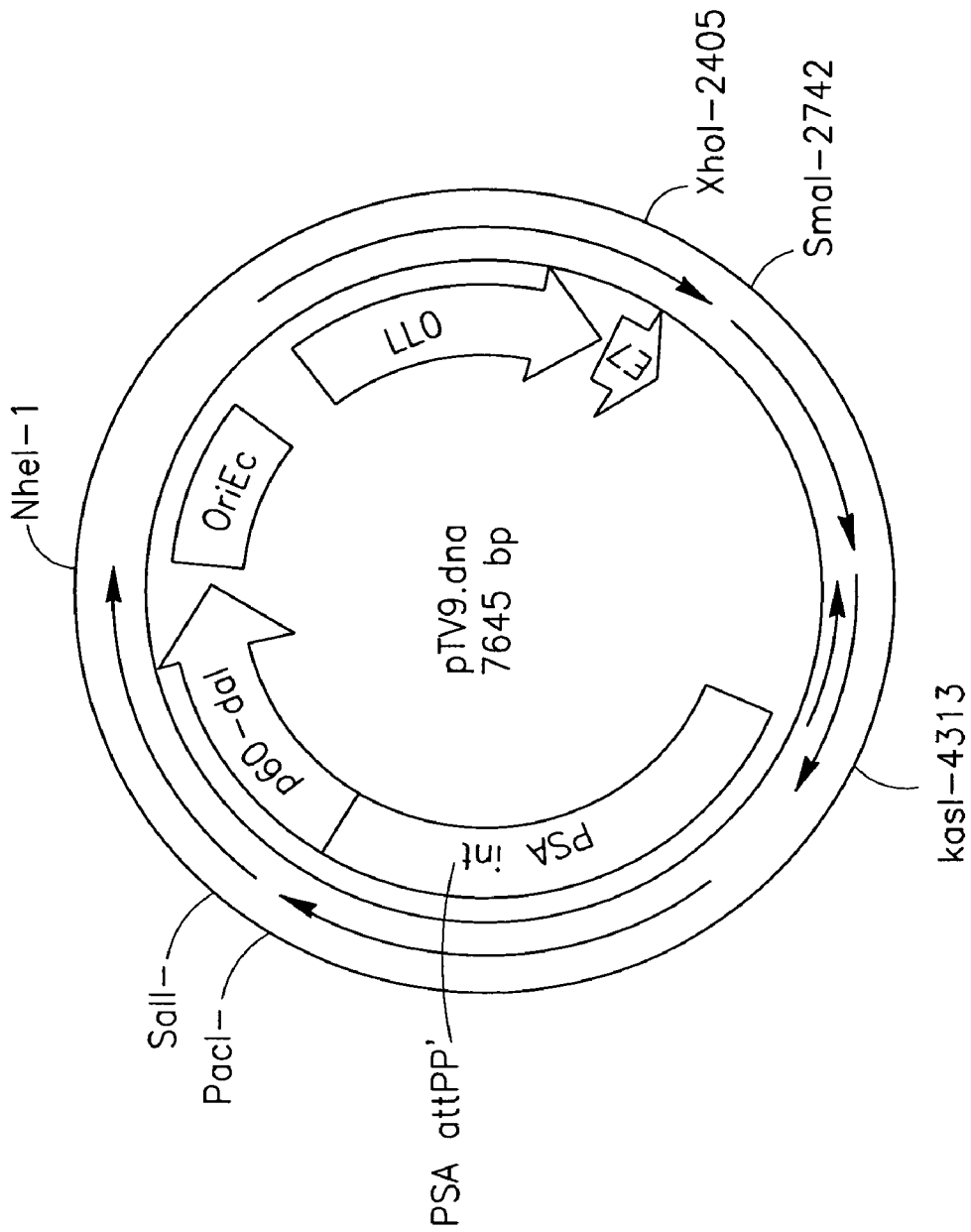
FIG. 12 Map of pTV9.

The PSA integrase gene and attPP' integration site from pPL2 are modified by PCR to contain restriction sites at the 5'-end and the 3'-end that are compatible with cloning these nucleic acids into shuttle plasmid pTV3 and the *Listeria* replication region from pTV3 is removed, resulting in plasmid pTV8 (FIG. 11). pTV8 is similar to pTV6, except that it contains the PSA sequences instead of the U153 sequences. pTV8 also contains a prfA gene, which is not necessary for function, as described above for pTV6, and can be removed (pTV9; FIG. 12).

Construction of pTV10-11

Figure 13:
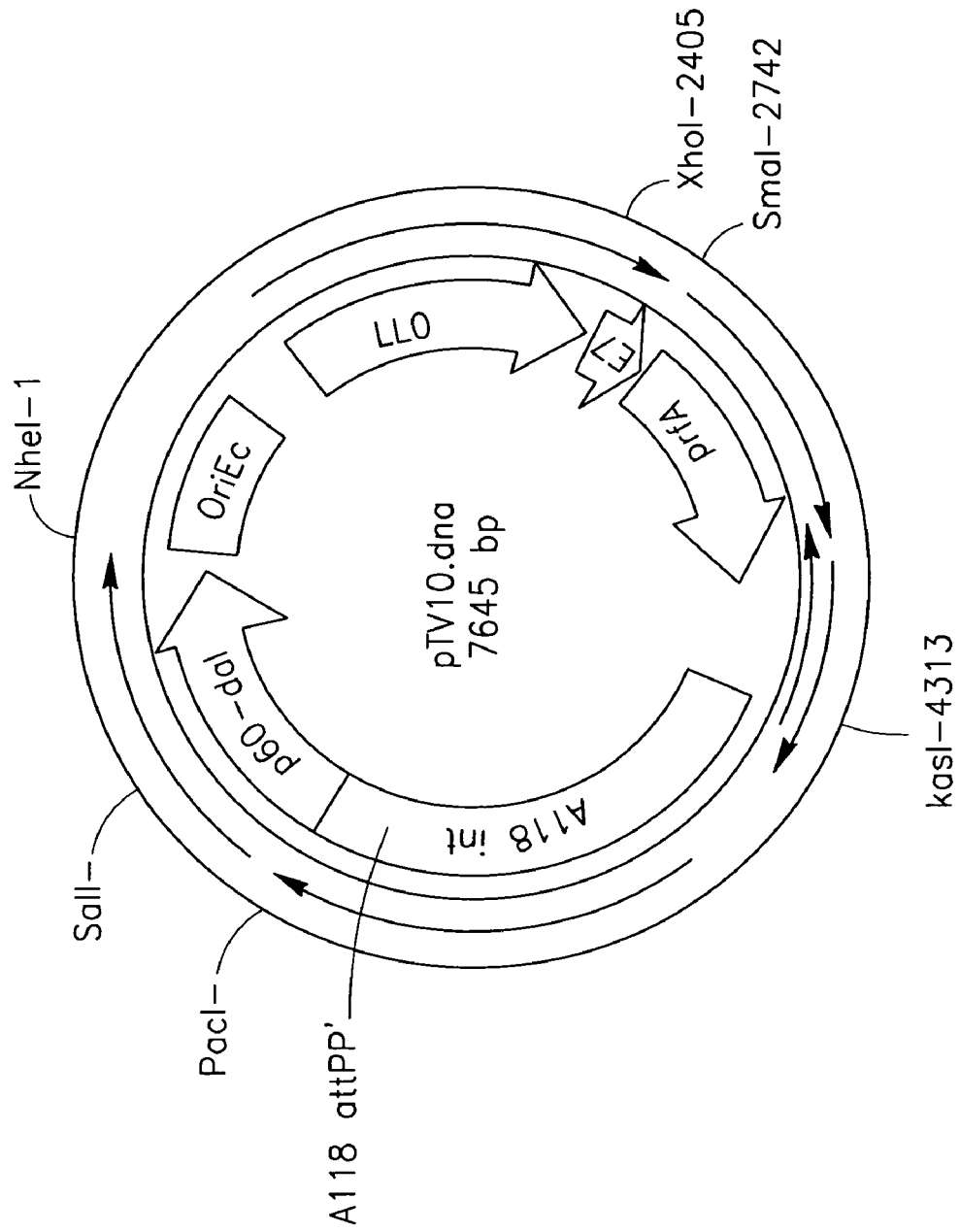
FIG. 13 Map of pTV10.
Figure 14:
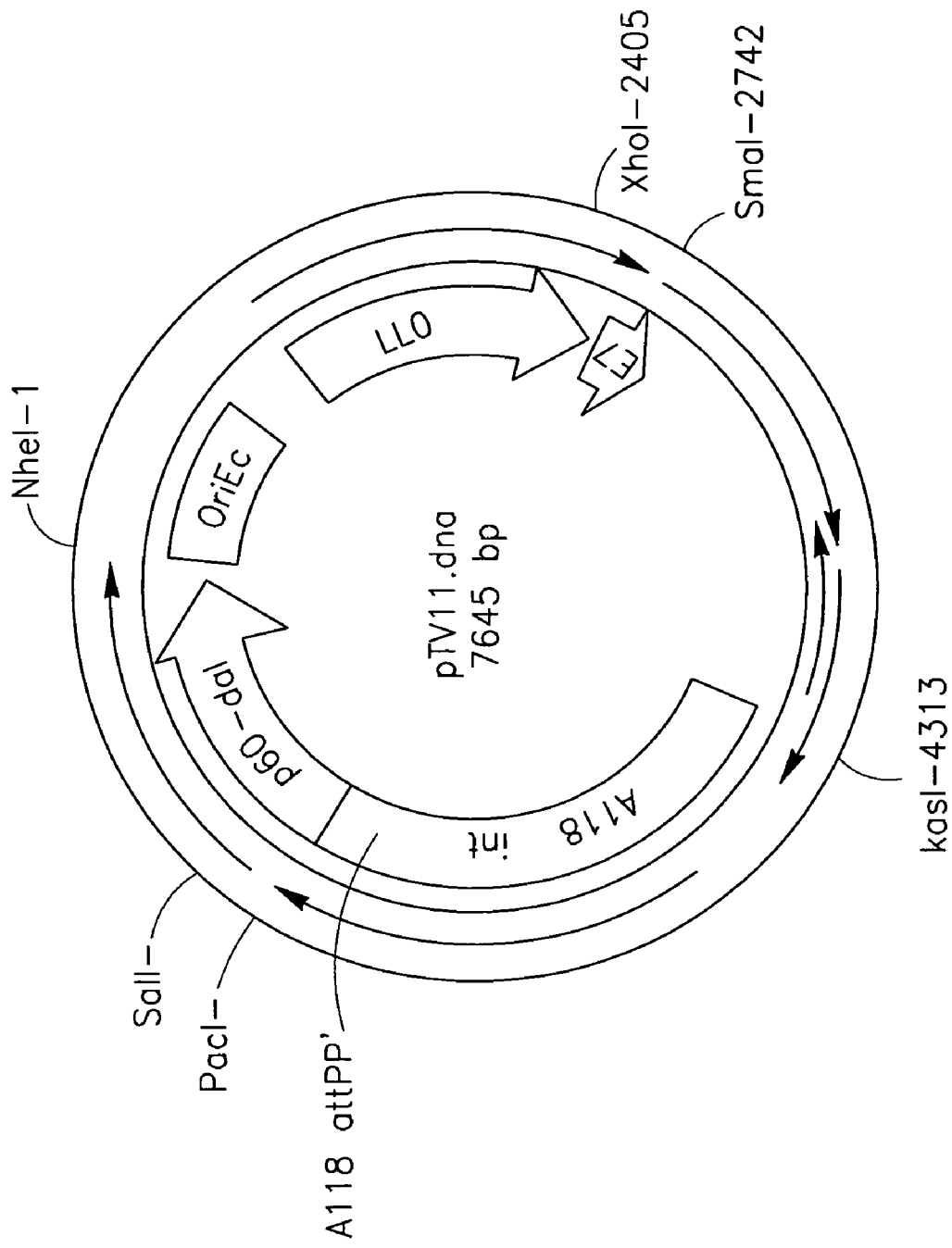
FIG. 14 Map of pTV11.

The A118 integrase gene and attPP' integration site from A118 DNA (GenBank Accession No. NC_003216) are modified by PCR to contain restriction sites at the 5'-end and the 3'-end that are compatible with cloning these nucleic acids into shuttle plasmid pTV3 and the *Listeria* replication region from pTV3 is removed, resulting in plasmid pTV10 (FIG. 13). pTV10 is similar to pTV6, except that it contains the A118 sequences instead of the U153 sequences. pTV10 also contains a prfA gene, which is not necessary for function, as described above for pTV6, and can be removed (pTV11; FIG. 14).

Phage Curing, Conjugation, and Molecular Confirmation of Plasmid Integration.

For phage curing, *L. monocytogenes* (LM) 10403S derivatives carrying a prophage at comK-attBB' (integrated in the comk open reading frame) are grown in BHI at 37° C. to $10^8$ CFU/ml and infected with listeriophage U153 at a multiplicity of infection of 20:1 in the presence of 5 mM $CaCl_2$. Cultures are incubated with shaking at 37° C. for 75 min, and inhibition of growth is monitored by comparison of the optical density at 600 nm ($OD_{600}$) of the infected culture with an uninfected control culture. The infected culture is diluted $10^{-2}$ and $10^{-4}$ in BHI, and both dilutions are grown at 37° C. until the $10^{-2}$ dilution culture increases 100-fold in optical density. The $10^4$-fold dilution culture is then diluted $10^{-2}$, and 3 microliter (mcl) is plated on BHI.

Fifty colonies are tested for phage release initially by transferring colonies into 0.25 ml of LB broth and replica plating at 30° C. on a lawn of Mack-4R (DP-L862), a non-lysogenic rough strain of *L. monocytogenes* particularly susceptible to forming plaques. Candidates are then tested for ability to form plaques by spotting 10 mcl of culture on a lawn of Mack-4R. Colonies that do not form plaques are tested for ability to support plaque formation by the phage from the parent 10403S strain (Φ10403 [Hodgson, D A. 2000. Generalized transduction of serotype ½ and serotype 4b strains of *Listeria monocytogenes*. Mol. Microbiol. 35:312-323]). Curing is confirmed molecularly by PCR with the comK-attBB-specific primer pair PL60 and PL61 (sequences follow) for the absence of a phage at comK-attBB. Approximately 10% of colonies are cured by using this procedure.

Recipient LM strains are made streptomycin resistant for counterselection in conjugation experiments by plate selection on BHI supplemented with 200 microgram (mcg) of antibiotic per ml.

pPL1 plasmid constructs were electroporated into *E. coli* strain MB2159, and bacterial strains are grown to mid-log phase ($OD_{600}$ of 0.55) with shaking at 30° C. *E. coli* donor strains are grown in LB containing 25 mcg of chloramphenicol/ml, and LM recipient strains are grown in BHI. Donor culture (2.5 ml) is mixed with 1.5 ml of recipient culture and filtered onto washed 0.45-micron-pore-size HA-type filters (47 mm; Millipore). The filter is washed once with 10 ml of BHI, transferred to a BHI plate with no antibiotics, and incubated for 2 h at 30° C. Bacterial cells are gently resuspended in 2.5 ml of BHI, and 25- and 50-mcl aliquots are plated in 3 ml of LB top agar on BHI plates supplemented with 7.5 mcg chloramphenicol and 200 mcg streptomycin per ml. Plates are incubated at 30° C. overnight and shifted to 37° C. for 2 to 3 days.

Individual colonies are picked and screened by PCR for integration at the phage attachment, using 2 pairs of primers: The first primer pair specifically amplifies attBP', thereby detecting integrated strains (but not those containing the vector as an episomal plasmid). The second primer pair specifically amplifies comK-attBB', thereby detecting nonlysogenic strains. PCR assays are performed in a Hybaid Omn-E™ thermocycler with an annealing temperature of 55° C. for 30 cycles; integrants arise at a frequency of approximately $10^4$ per donor cell.

Results

In a first experiment, a shuttle plasmid is constructed containing (1) a replication gene for *E. coli*, (2) a U153 attPP' integration site, (3) a *Listeria* dal gene under the control of its natural promoter, and (4) a U153 integrase gene under the control of the *Listeria* p60 promoter. The U153 integrase gene and attPP' integration site are subcloned into shuttle plasmid pTV3, and the *Listeria* replication region from pTV3 is removed, generating plasmid pTV6. The plasmid is amplified in dal auxotroph *E. coli* strain MB2159 (Example 1), isolated, and subsequently conjugated into *Listeria*. Because the plasmid does not contain a *Listeria* replication region, only *Listeria* that contain a copy that is integrated into the genome are selected upon growth in LB media. In other experiments, as a further selective measure, alanine-free media is utilized.

In other experiments, to facilitate prophage integration, phage curing is performed prior to conjugation. In other experiments, an integration vector not requiring phage curing (e.g. a PSA vector) is utilized.

In another experiment, a similar shuttle plasmid, pTV8, is constructed, but using instead a PSA attPP' integration site and integrase gene. The plasmid is amplified and conjugated into *Listeria*, as described for pTV6.

In another experiment, a similar shuttle plasmid, pTV10, is constructed, but using instead a A118 attPP' integration site and integrase gene. The plasmid is amplified and conjugated into *Listeria*, as described for pTV6.

EXAMPLE 8

Creation of General Shuttle Integration Vectors Based on pTV6, 8, and 11 pTV6, 8, and 11 are digested with KasI or EheI and AatII, and/or other appropriate restriction enzymes, removing the prfA gene, the LL0-E7 fusion gene, and most of the LLO promoter. A multiple cloning site consisting of BamHI, XhoI, XbaI, NotI, SpeI, SmaI, and SacI is introduced by ligating the following paired oligonucleotides to the vector backbone:

5'-CGG ATC CCT CGA GCT CAG AGC GGC CGC ACT AGT CCC GGG GAG CTC G (SEQ ID No: 40).

5'-TCG ACG AGC TCC CCG GGA CTA GTG CGG CCG CTC TGA GCT CGA GGG ATC CGA CGT (SEQ ID No: 41; overhanging ends that are compatible with the vector sites restricted with AatI and SalI are in italics).

An antigen cassette of interest is then ligated into the multiple cloning site. The plasmid is then used to create a vaccine strain expressing the antigen encoded therein.

What is claimed is:

1. A recombinant *Listeria* strain comprising an integrated nucleic acid molecule, wherein said integrated nucleic acid molecule comprises a) a first open reading frame encoding a polypeptide comprising a protein antigen, and b) a second open reading frame encoding a metabolic enzyme, wherein said nucleic acid molecule does not comprise an antibiotic resistance gene, and further wherein said nucleic acid is stably retained in said recombinant *Listeria* under in vitro and in vivo conditions.

2. The recombinant *Listeria* strain of claim 1, wherein said nucleic acid molecule further comprises a gene encoding a transcription factor.

3. The recombinant *Listeria* strain of claim 2, wherein the chromosome of said recombinant *Listeria* a strain lacks said gene encoding a transcription factor.

4. The recombinant *Listeria* strain of claim 1, wherein said polypeptide is a fusion protein comprising said protein antigen and an additional polypeptide, wherein said additional peptide enhances the immunogenicity of said protein antigen.

5. The recombinant *Listeria* strain of claim 2, wherein said additional polypeptide is a non-hemolytic LLO protein or fragment thereof, a PEST- amino acid sequence, or an ActA fragment.

6. The recombinant *Listeria* strain of claim 1, wherein said nucleic acid molecule is a phage integration vector.

7. The recombinant *Listeria* strain of claim 1, wherein said metabolic enzyme is an amino acid metabolism enzyme.

8. The recombinant *Listeria* strain of claim 1, wherein said metabolic enzyme catalyzes a formation of an amino acid used for a cell wall synthesis in said recombinant *Listeria* strain.

9. The recombinant *Listeria* strain of claim 1, wherein said metabolic enzyme is an alanine racemase enzyme.

10. The recombinant *Listeria* strain of claim 1, wherein said metabolic enzyme is a D-amino acid transferase enzyme.

11. The recombinant *Listeria* strain of claim 1, wherein said recombinant *Listeria* strain has been passaged through an animal host.

12. The recombinant *Listeria* of claim 1, wherein said nucleic acid comprises a third open reading frame encoding an additional metabolic enzyme.

13. The recombinant *Listeria* strain of claim 12, wherein said metabolic enzyme catalyzes a formation of an amino acid used for a cell wall synthesis in said recombinant *Listeria* strain.

14. The recombinant *Listeria* strain of claim 12, wherein said metabolic enzyme is an alanine racemase enzyme.

15. The recombinant *Listeria* strain of claim 12, wherein said metabolic enzyme is a D-amino acid transferase enzyme.

* * * * *

SEQUENCE LISTING

```
<160> NUMBER OF SEQ ID NOS: 71

<210> SEQ ID NO 1
<211> LENGTH: 21
<212> TYPE: DNA
<213> ORGANISM: Artificial
<220> FEATURE:
<223> OTHER INFORMATION: LM alanine racemase (dal) gene forward primer

<400> SEQUENCE: 1
ccatggtgac aggctggcat c                                          21

<210> SEQ ID NO 2
<211> LENGTH: 27
<212> TYPE: DNA
<213> ORGANISM: Artificial
<220> FEATURE:
<223> OTHER INFORMATION: LM alanine racemase (dal) gene reverse primer

<400> SEQUENCE: 2
gctagcctaa tggatgtatt ttctagg                                    27

<210> SEQ ID NO 3
<211> LENGTH: 27
<212> TYPE: DNA
<213> ORGANISM: Artificial
<220> FEATURE:
<223> OTHER INFORMATION: minimal p60 promoter sequence forward primer

<400> SEQUENCE: 3
ttaattaaca aatagttggt atagtcc                                    27

<210> SEQ ID NO 4
<211> LENGTH: 36
<212> TYPE: DNA
<213> ORGANISM: Artificial
<220> FEATURE:
<223> OTHER INFORMATION: minimal p60 promoter sequence reverse primer

<400> SEQUENCE: 4
```

```
gacgatgcca gcctgtcacc atggaaaact cctctc                                36
```

<210> SEQ ID NO 5
<211> LENGTH: 156
<212> TYPE: DNA
<213> ORGANISM: Listeria monocytogenes

<400> SEQUENCE: 5

```
caaatagttg gtatagtcct ctttagcctt tggagtatta tctcatcatt tgttttttag     60
gtgaaaactg ggtaaactta gtattatcaa tataaaatta attctcaaat acttaattac    120
gtactgggat tttctgaaaa aagagaggag ttttcc                              156
```

<210> SEQ ID NO 6
<211> LENGTH: 25
<212> TYPE: DNA
<213> ORGANISM: Artificial
<220> FEATURE:
<223> OTHER INFORMATION: 5'-primer that added a NarI/EheI site upstream
      of the sequence

<400> SEQUENCE: 6

```
ggcgccacta actcaacgct agtag                                           25
```

<210> SEQ ID NO 7
<211> LENGTH: 27
<212> TYPE: DNA
<213> ORGANISM: Artificial
<220> FEATURE:
<223> OTHER INFORMATION: 3'-primer that added a NheI site downstream of
      the sequence

<400> SEQUENCE: 7

```
gctagccagc aaagaaaaac aaacacg                                         27
```

<210> SEQ ID NO 8
<211> LENGTH: 38
<212> TYPE: DNA
<213> ORGANISM: Artificial
<220> FEATURE:
<223> OTHER INFORMATION: Primer 1

<400> SEQUENCE: 8

```
gtcgacggtc accggcgcca ctaactcaac gctagtag                             38
```

<210> SEQ ID NO 9
<211> LENGTH: 35
<212> TYPE: DNA
<213> ORGANISM: Artificial
<220> FEATURE:
<223> OTHER INFORMATION: Primer 2

<400> SEQUENCE: 9

```
ttaattaagc tagccagcaa agaaaaacaa acacg                                35
```

<210> SEQ ID NO 10
<211> LENGTH: 29
<212> TYPE: DNA
<213> ORGANISM: Artificial
<220> FEATURE:
<223> OTHER INFORMATION: LLO-E7 gene was PCR amplified from pGG55

<400> SEQUENCE: 10

```
atgaaaaaaa taatgctagt ttttattac                                       29
```

```
<210> SEQ ID NO 11
<211> LENGTH: 38
<212> TYPE: DNA
<213> ORGANISM: Artificial
<220> FEATURE:
<223> OTHER INFORMATION: LLO-E7 gene was PCR amplified from pGG55

<400> SEQUENCE: 11
gcggccgctt aatgatgatg atgatgatgt ggtttctg                              38

<210> SEQ ID NO 12
<211> LENGTH: 22
<212> TYPE: DNA
<213> ORGANISM: Artificial
<220> FEATURE:
<223> OTHER INFORMATION: Primer

<400> SEQUENCE: 12
gcaagtgtga ctctacgctt cg                                               22

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
tgcccattaa caggtcttcc a                                                21

<210> SEQ ID NO 14
<211> LENGTH: 32
<212> TYPE: DNA
<213> ORGANISM: Artificial
<220> FEATURE:
<223> OTHER INFORMATION: Primer

<400> SEQUENCE: 14
tgcgtacaaa gcacacacgt agacattcgt ac                                    32

<210> SEQ ID NO 15
<211> LENGTH: 24
<212> TYPE: DNA
<213> ORGANISM: Artificial
<220> FEATURE:
<223> OTHER INFORMATION: Primer

<400> SEQUENCE: 15
tgacatcgtt tgtgtttgag ctag                                             24

<210> SEQ ID NO 16
<211> LENGTH: 23
<212> TYPE: DNA
<213> ORGANISM: Artificial
<220> FEATURE:
<223> OTHER INFORMATION: Primer

<400> SEQUENCE: 16
gcagcgctct ctataccagg tac                                              23

<210> SEQ ID NO 17
<211> LENGTH: 38
<212> TYPE: DNA
<213> ORGANISM: Artificial
<220> FEATURE:
<223> OTHER INFORMATION: Primer
```

```
<400> SEQUENCE: 17
ttaatgtcca tgttatgtct ccgttatagc tcatcgta                                    38

<210> SEQ ID NO 18
<211> LENGTH: 9
<212> TYPE: PRT
<213> ORGANISM: Human papillomavirus type 16

<400> SEQUENCE: 18

Arg Ala His Tyr Asn Ile Val Thr Phe
1               5

<210> SEQ ID NO 19
<211> LENGTH: 6094
<212> TYPE: DNA
<213> ORGANISM: Artificial
<220> FEATURE:
<223> OTHER INFORMATION: Shuttle integration vector pPL1

<400> SEQUENCE: 19
gacgtcatta accctcacta aagggaacaa aagctgggta ccgggccccc cctcgaggtc            60
gacggtatcg ataagcttga tatcgaattc ctgcagcccg ggggatccac tagttctaga           120
gcggccgcca ccgcggtgga gctccaattc gccctatagt gagtcgtatt gacgtcgcta           180
tttaacgacc ctgccctgaa ccgacgaccg ggtcgaattt gctttcgaat ttctgccatt           240
catccgctta ttatcactta ttcaggcgta gcaccaggcg tttaagggca ccaataactg           300
ccttaaaaaa attacgcccc gccctgccac tcatcgcagt actgttgtaa ttcattaagc           360
attctgccga catggaagcc atcacagacg catgatgaa cctgaatcgc cagcggcatc            420
agcaccttgt cgccttgcgt ataatatttg cccatggtga aacgggggc gaagaagttg            480 tccatattgg ccacgtttaa atcaaaactg gtgaaactca cccagggatt ggctgagacg           540
aaaaacatat tctcaataaa ccctttaggg aataggcca ggttttcacc gtaacacgcc            600
acatcttgcg aatatatgtg tagaaactgc cggaaatcgt cgtggtattc actccagagc           660
gatgaaaacg tttcagtttg ctcatggaaa acggtgtaac aagggtgaac actatcccat           720
atcaccagct caccgtcttt cattgccata cggaattccg gatgagcatt catcaggcgg           780
gcaagaatgt gaataaaggc cggataaaac ttgtgcttat ttttctttac ggtctttaaa           840
aaggccgtaa tatccagctg aacggtctgg ttataggtac attgagcaac tgactgaaat           900
gcctcaaaat gttctttacg atgccattgg gatatatcaa cggtggtata ccagtgatt            960 ttttctcca ttttagcttc cttagctcct gaaaatctcg ataactcaaa aaatacgccc           1020
ggtagtgatc ttatttcatt atggtgaaag ttggaacctc ttacgtgccg atcaacgtct          1080
cattttcgcc aaaagttggc ccagggcttc ccggtatcaa cagggacacc aggatttatt         1140
tattctgcga agtgatcttc cgtcacaggt atttattcgg cgcaaagtgc gtcgggtgat         1200
gctgccaact tactgattta gtgtatgatg gtgtttttga ggtgctccag tggcttctgt         1260
ttctatcagc tgtccctcct gttcagctac tgacggggtg gtgcgtaacg gcaaaagcac         1320
cgccggacat cagcgctagc ggagtgtata ctggcttact atgttggcac tgatgagggt         1380
gtcagtgaag tgcttcatgt ggcaggagaa aaaaggctgc accggtgcgt cagcagaata         1440
tgtgatacag gatatattcc gcttcctcgc tcactgactc gctacgctcg tcgttcgac          1500 tgcggcgagc ggaaatggct tacgaacggg cgagagattt cctggaagat gccaggaaga         1560
tacttaacag ggaagtgaga gggccgcggc aaagccgttt tccataggc tccgcccccc          1620
```

```
tgacaagcat cacgaaatct gacgctcaaa tcagtggtgg cgaaacccga caggactata    1680
aagataccag gcgtttcccc ctggcggctc cctcgtgcgc tctcctgttc ctgcctttcg    1740
gtttaccggt gtcattccgc tgttatggcc gcgtttgtct cattccacgc ctgacactca    1800
gttccgggta ggcagttcgc tccaagctgg actgtatgca cgaaccccec gttcagtccg    1860 accgctgcgc cttatccggt aactatcgtc ttgagtccaa cccggaaaga catgcaaaag    1920
caccactggc agcagccact ggtaattgat ttagaggagt tagtcttgaa gtcatgcgcc    1980
ggttaaggct aaactgaaag acaagtttt ggtgactgcg ctcctccaag ccagttacct     2040
cggttcaaag agttggtagc tcagagaacc ttcgaaaaac cgccctgcaa ggcggttttt    2100
tcgttttcag agcaagagat tacgcgcaga ccaaaacgat ctcaagaaga tcatcttatt    2160
aatcagataa aatatttcta gatttcagtg caatttatct cttcaaatgt agcacctgaa    2220
gtcagcccca tacgatataa gttgtaattc tccgccgctt gccctcatct gttacgccgg    2280
cggtagccgg ccagcctcgc agagcaggat tcccgttgag caccgccagg tgcgaataag    2340
ggacagtgaa gaaggaacac ccgctcgcgg gtgggcctac ttcacctatc ctgcccggct    2400
gacgccgttg gatacaccaa ggaaagtcta cacgaaccct ttggcaaaat cctgtatatc    2460
gtgcgaaaaa ggatggatat tccgaaaaaa tcgctataat gaccccgaag cagggttatg    2520
cagcggaaaa gcgctgcttc cctgctgttt tgtggaatat ctaccgactg gaaacaggca    2580
aatgcaggaa attactgaac tgaggggaca ggcgagaggc atgcgataaa aagcaatcta    2640
tagaaaaaca ggttacttt tatttataat tttagtttct cgattcgttt ccgtccaacg     2700
agagaaaacg aggaactaaa caatctaaat aaacaagcta ctagagccat caatagtaa    2760 cttgttcacc gtcaatataa atttattaa ttagtgattt taaataaagt tgcttttctc     2820
ggaactctaa agagtcaaaa tcaactgttg ctaaatcagc taaattttct tgtatctttt    2880
tattttcctt caattcttcg ttagcttcta tttgtgcttc ataataatta atttgagcat    2940
cgatatcagc catcatagca tcaagttctg aaacttcgta agaaccgctg atatataaat    3000
caaatagccg tttcttttt acgtgttctg ttttaagttt ttcatttaag ctatctaatt     3060
cgtcttcttt atctacattc ctagaagcga aactatagtt attcacgcga tcaataatta    3120
attcctcgag tttgtcagct ctccaaattt tatttccaca ttttttctagt tcatgagtat    3180 gtttgtaagt cttgcaacta taatatctat aatgatattt ttttccgcgg gaaacagtat    3240
cttttctccg atgaacaaaa cccaacccac attttccaca cactaccaaa ttatttagca    3300
acgatgctga atctctattc atatttggat ttttacccat gcgagaaaaa atttcttgaa    3360
ctcgataaaa ttgttcctct gaaataatag gctcatgaac acctttgta tgcactttat    3420 ccgcataaga tacataacca cagtataaat cattagttag ccaattgttg taactgctat    3480
atgatttcac tttgaatcct aattttttta gtctcttctg taaagtggta atgcttttt    3540 cttcctcaaa aatatcataa atcatttgta attgttttgc ttcttcttca ttaatatata    3600
atttagtatc tataacatca tagccgaatg ttctacctt tgcagtcgtt aaaggaagac     3660
ctgcttcaat acgcttaatt ttccccatca ccatacgatc acgtatagtt tcgcgctcta    3720
attgagcaaa tacggataat ataccaatca tcgcgcgccc aaatgggcta gaggtgtcaa    3780
gagtttcaga caaactaaca aattctacat tgtttttaa gaagtattct tcaataagcg     3840
ttatcgtatc tctttgtgag cgggaaagtc tatctaagcg atatacaaca acagcatcaa    3900
tttcatgtaa tttacttagc atttcattta gtgcggggcg attcatgttt gaaccgctgt    3960
atccgccgtc tatgaaaata tcgtatacgt cccaatcctt cgagcggcac aaggctgtta    4020
```

-continued

```
gcttttcagt ttgagcttgt atagagtaat tctctatttg ttcttgagta gatacgcgta    4080
tataaatagc tgccttcatt tccgttctcc tctcgcatgg aaagttaaga tctttttttc    4140
agaaaatccc agtacgtaat taagtatttg agaattaatt ttatattgat taatactaag    4200
tttacccagt tttcacctaa aaacaaatg atgagataat agctccaaag gctaaagagg     4260
actataccaa ctatttgtaa taattctgta acagttgaaa agcgaacgtg tattcttagg    4320
gcttgagatg tattgctggg taaaccttta tagtgtaagt gggatgtgaa cgttaatcaa    4380
caactttcgc tatgggaaac ctattgtttt ttgttaatag aaaaacttaa tacatttgta    4440
atataaaaac cggcagtttt tccgttcttc gtgactcgaa atgaattgcc agatgagttt    4500
atggtattct ataatagaag gtatggagga tgttatataa tgagacagaa ttatgatgat    4560
cgaaagctag cttggcactg gccgtcgttt tacaacgtcg tgactgggaa accctggcg    4620 ttacccaact taatcgcctt gcagcacatc cccctttcgc cagctggcgt aatagcgaag    4680
aggcccgcac cgatcgccct tcccaacagt tgcgcagcct gaatggcgaa tggcgcctga    4740
tgcggtattt tctccttacg catctgtgcg gtatttcaca ccgcatatga tcccggatct    4800
ggagctgtaa tataaaaacc ttcttcaact aacggggcag gttagtgaca ttagaaaacc    4860
gactgtaaaa agtacagtcg gcattatctc atattataaa agccagtcat taggcctatc    4920
tgacaattcc tgaatagagt tcataaacaa tcctgcatga taaccatcac aaacagaatg    4980
atgtacctgt aaagatagcg gtaaatatat tgaattacct ttattaatga attttcctgc    5040
tgtaataatg ggtagaaggt aattactatt attattgata tttaagttaa acccagtaaa    5100
tgaagtccat ggaataatag aaagagaaaa agcatttca ggtataggtg ttttgggaaa     5160
caatttcccc gaaccattat atttctctac atcagaaagg tataaatcat aaaactcttt    5220
gaagtcattc tttacaggag tccaaatacc agagaatgtt ttagatacac catcaaaaat    5280
tgtataaagt ggctctaact tatcccaata acctaactct ccgtcgctat tgtaaccagt    5340
tctaaaagct gtatttgagt ttatcaccct tgtcactaag aaaataaatg cagggtaaaa    5400
tttatatcct tcttgtttta tgtttcggta taaaacacta atatcaattt ctgtggttat    5460
actaaaagtc gtttgttggt tcaaataatg attaaatatc tcttttctct tccaattgtc    5520
taaatcaatt ttattaaagt tcatttgata tgcctcctaa attttttatct aaagtgaatt   5580 taggaggctt acttgtctgc tttcttcatt agaatcaatc cttttttaaa agtcaatatt    5640
actgtaacat aaatatatat tttaaaaata tcccacttta tccaattttc gtttgttgaa    5700
ctaatgggtg ctttagttga agaataaaag accacattaa aaaatgtggt cttttgtgtt    5760
tttttaaagg atttgagcgt agcgaaaaat ccttttcttt cttatcttga taataagggt    5820
aactattgcc cagatccggg atcatatggt gcactctcag tacaatctgc tctgatgccg    5880
catagttaag ccagccccga cacccgccaa cacccgctga cgcgccctga cgggcttgtc    5940
tgctcccggc atccgcttac agacaagctg tgaccgtctc cgggagctgc atgtgtcaga    6000
ggttttcacc gtcatcaccg aaacgcgcga gacgaaaggg cctcgtgata cgcctatttt    6060
tataggttaa tgtcatgata taatggtttc ctta                                 6094
```

<210> SEQ ID NO 20
<211> LENGTH: 25
<212> TYPE: DNA
<213> ORGANISM: Artificial
<220> FEATURE:
<223> OTHER INFORMATION: Primer

```
<400> SEQUENCE: 20
ggacgtcatt aaccctcact aaagg                                          25

<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
ggacgtcaat acgactcact atagg                                          25

<210> SEQ ID NO 22
<211> LENGTH: 25
<212> TYPE: DNA
<213> ORGANISM: Artificial
<220> FEATURE:
<223> OTHER INFORMATION: Primer

<400> SEQUENCE: 22
ggacgtcgct atttaacgac cctgc                                          25

<210> SEQ ID NO 23
<211> LENGTH: 36
<212> TYPE: DNA
<213> ORGANISM: Artificial
<220> FEATURE:
<223> OTHER INFORMATION: Primer

<400> SEQUENCE: 23
gagctgcagg agaattacaa cttatatcgt atgggg                              36

<210> SEQ ID NO 24
<211> LENGTH: 33
<212> TYPE: DNA
<213> ORGANISM: Artificial
<220> FEATURE:
<223> OTHER INFORMATION: Primer

<400> SEQUENCE: 24
gcactgcagc cgcttgccct catctgttac gcc                                 33

<210> SEQ ID NO 25
<211> LENGTH: 33
<212> TYPE: DNA
<213> ORGANISM: Artificial
<220> FEATURE:
<223> OTHER INFORMATION: Primer

<400> SEQUENCE: 25
catgcatgcc tctcgcctgt cccctcagtt cag                                 33

<210> SEQ ID NO 26
<211> LENGTH: 3897
<212> TYPE: DNA
<213> ORGANISM: Bacteriophage U153
<220> FEATURE:
<221> NAME/KEY: misc_feature
<222> LOCATION: (695)..(695)
<223> OTHER INFORMATION: n is a, c, g, or t

<400> SEQUENCE: 26
aagctttaaa gaaattcaag aagaaacatc ggtaactagc cataaattaa ccaaagttct    60
aatctcgctt gaagagaaca aactgattga aaaaattgga caatctagag caacaaaata  120
```

```
caaattaatt gaatctacag aggaatatct aaccaatctt caacacacat ttcgaaaaat      180
tgttcaattt tatgttgaaa atgataaata aaaatatgaa tgttttttta tttgttagta      240
gtgtaacttt ccatgcgaga ggagaacgga aatgaaggca gctatttata tacgcgtatc      300
tactcaagaa caaatagaga attactctat acaagctcaa actgaaaagc taacagcctt      360
gtgccgctcg aaggattggg acgtatacga tattttcata gacggcggat acagcggttc      420
aaacatgaat cgccccgcac taaatgaaat gctaagtaaa ttacatgaaa ttgatgctgt      480
tgttgtatat cgcttagata gactttcccg ctcacaaaga gatacgataa cgcttattga      540
agaatacttc ttaaaaaaca atgtagaatt tgttagtttg tctgaaactc ttgacacctc      600
tagcccattt gggcgcgcga tgattggtat attatccgta tttgctcaat tagagcgcga      660
aactatacgt gatcgtatgg tgatggggaa aattnagcgt attgaagcag gtcttccttt      720
aacgactgca aaaggtagaa cattcggcta tgatgttata gatactaaat tatatattaa      780
tgaagaagaa gcaaaacaat tacaaatgat ttatgatatt tttgaggaag aaaaaagcat      840
taccacttta cagaagagac taaaaaaatt aggattcaaa gtgaaatcat atagcagtta      900
caacaattgg ctaactaatg atttatactg tggttatgta tcttatgcgg ataaagtgca      960
tacaaaaggt gttcatgagc ctattatttc agaggaacaa ttttatcgag ttcaagaaat     1020
tttttctcgc atgggtaaaa atccaaatat gaatagagat tcagcatcgt tgctaaataa     1080
tttggtagtg tgtggaaaat gtgggttggg ttttgttcat cggagaaaag atactgtttc     1140
ccgcggaaaa aaatatcatt atagatatta tagttgcaag acttacaaac atactcatga     1200
actagaaaaa tgtggaaata aaatttggag agctgacaaa ctcgaggaat taattattga     1260
tcgcgtgaat aactatagtt tcgcttctag gaatgtagat aaagaagacg aattagatag     1320
cttaaatgaa aaacttaaaa cagaacacgt aaaaagaaa cggctatttg atttatatat     1380
cagcggttct tacgaagttt cagaacttga tgctatgatg gctgatatcg atgctcaaat     1440
taattattat gaagcacaaa tagaagctaa cgaagaattg aagaaaaata aaaagataca     1500
agaaaattta gctgatttag caacagttga ttttgactct ttagagttcc gagaaaagca     1560 actttatttta aaatcactaa ttaataaaat ttatattgac ggtgaacaag ttactattga     1620
atggctctag tagcttgttt atttagattg tttagttcct cgttttctct cgttggacgg     1680
aaacgaatcg agaaactaaa attataaata aaaagtaacc tgttttttcta tagattgctt     1740 tttatcaatt atatagaaga aagccgcttt ttattagatt ataattgatg ttttttgatt     1800
tatatttcac tccctgtgca aataatgata taacagcaac ctcgaacttt ttagttcggg     1860 gtatttttt gaaattaatt tataaaaaca cttgcaatta tataatacat gtattataat     1920
ataaatatag aaaggagttg agaaagtgaa agacatctta gaggaaataa aaacagtcct     1980
tgaaattgta actcttgcag tagcgctgat aacattacgc aagatagaca aaaacaagga     2040
caagtaacca gaggggtgaa actcccctcc ctctataaaa gtatatcacg tctttcataa     2100
attatgaata aatatatctg ggttatatta attgttatat gcgttaacgg actcgctagt     2160
tactttcaga acacagcatt gaccatcatt gctatactga ctacattagc ttgtttagta     2220
tatttaataa aaaataggaa gtgattaatt atgacgaaaa aaacgacctc tgacgcgcag     2280
ttgaaagcaa ataaggaatg gcaaagcaag aacaaagaac atgcaaacta tttaaaatct     2340
cgttcagctg cgcgttcttt tataaagaat aaagctacgt tggaagattt gaaggaactt     2400
gaaaaattaa ttatagaggg aaaaattaat cataaggaa tgattaagga taaatgatgc     2460
```

```
acgctaagca catgcttggc gttttttgca taaaaaaagc cctaacgttg aagttaggga   2520
ctgacatata taaaaaatag aagttgacaa ctttaaggcg actaccacga caggcagctt   2580
acaagctatg actagccttg actaatcatt tatgcgacac tcaaagaatt attatctaac   2640
ttcttaatca agaataacaa aaatcaaaca agttagcaag tatttcaggc attttattta   2700
taacaaatat ctagatcaca aaatgtcgc ggaaaataat ggtcacaacc aatattacat    2760
aaacttaaaa gttctctatt tctcttatca ggtttatgtg ctgttacgtg atttctacat   2820
actctaaaaa ctgtattagc gaataagtct acaacttgaa ttaaatcttt attttgtgaa   2880
tccttatatg atgtttcaac agaagagaaa attggatgtt ccattgtaaa tttaatagtt   2940
aaatattctt gtaagctatt taatgattca attgcggtat ttctatcatc tatttgcatt   3000
ttcaaatagt tatttgctgg gttaattggt attttagaaa tttcatttac cgttagataa   3060 ataaataat taaagacaa agatgtatta ttcaaaagat gattgactag ttggtggtta    3120
tcgactatct taaaatgaaa tttagcatct gattttgttg aaagcatatt aaatattaat   3180
ttttcatttt caaaggcat ctccgaacct tttatctctt ttgtaatatc taacttacta    3240
gatggatacc ttttaagata ttttaatttt gcatctctga actgtctaat tacattatat   3300
ggtttctctg tttctaaaaa agcaataaca aaatatctgt tattaaaatt tttattttta   3360
gttatagttc ctgattcatc tacaaaaagt ctcatcccag ttcctccact tttttactta   3420
aattatatta tactaattaa gtttgaggaa gtggaacgta tgtacttata attcgaagtt   3480
atgaaaaatc cccccatcaa tataaaacaa aaagcccccc gaaataataa tcgagggcat   3540
taaactaaat cttttaaca aacttcggtg ttagcagtga gatagtaacc agatttcgtt    3600
ttcaagcgag gtgttccgcc tttttgttttc gccattcctg taatcgtgaa gatagtgcct   3660
accggatatg tgccaccggt tttatgcttc tcagtaaagt ctactgaatt gtatagatca   3720
cactgtacta gtgttttaac ttttcgcgga ttttctgtgt agtatgtgtt tttgcttgct    3780
ggtgtgtgtg gttttcctgc ttttaacttc gctaataatg ttgtgttctg cgttgctgtt   3840
cctttataat ccttaattcc gtattgattt gctagttttt tacgattcgc aaagctt      3897
```

<210> SEQ ID NO 27
<211> LENGTH: 452
<212> TYPE: PRT
<213> ORGANISM: Bacteriophage U153
<220> FEATURE:
<221> NAME/KEY: misc_feature
<222> LOCATION: (142)..(142)
<223> OTHER INFORMATION: Xaa can be any naturally occurring amino acid

<400> SEQUENCE: 27

Met Lys Ala Ala Ile Tyr Ile Arg Val Ser Thr Gln Glu Gln Ile Glu
1               5                   10                  15

Asn Tyr Ser Ile Gln Ala Gln Thr Glu Lys Leu Thr Ala Leu Cys Arg
            20                  25                  30

Ser Lys Asp Trp Asp Val Tyr Asp Ile Phe Ile Asp Gly Gly Tyr Ser
        35                  40                  45

Gly Ser Asn Met Asn Arg Pro Ala Leu Asn Glu Met Leu Ser Lys Leu
    50                  55                  60

His Glu Ile Asp Ala Val Val Val Tyr Arg Leu Asp Arg Leu Ser Arg
65                  70                  75                  80

Ser Gln Arg Asp Thr Ile Thr Leu Ile Glu Glu Tyr Phe Leu Lys Asn
                85                  90                  95

Asn Val Glu Phe Val Ser Leu Ser Glu Thr Leu Asp Thr Ser Ser Pro

-continued

```
                100                 105                 110
    Phe Gly Arg Ala Met Ile Gly Ile Leu Ser Val Phe Ala Gln Leu Glu
            115                 120                 125
    Arg Glu Thr Ile Arg Asp Arg Met Val Met Gly Lys Ile Xaa Arg Ile
        130                 135                 140
    Glu Ala Gly Leu Pro Leu Thr Thr Ala Lys Gly Arg Thr Phe Gly Tyr
    145                 150                 155                 160
    Asp Val Ile Asp Thr Lys Leu Tyr Ile Asn Glu Glu Ala Lys Gln
                    165                 170                 175
    Leu Gln Met Ile Tyr Asp Ile Phe Glu Glu Lys Ser Ile Thr Thr
                180                 185                 190
    Leu Gln Lys Arg Leu Lys Lys Leu Gly Phe Lys Val Lys Ser Tyr Ser
            195                 200                 205
    Ser Tyr Asn Asn Trp Leu Thr Asn Asp Leu Tyr Cys Gly Tyr Val Ser
        210                 215                 220
    Tyr Ala Asp Lys Val His Thr Lys Gly Val His Glu Pro Ile Ile Ser
    225                 230                 235                 240
    Glu Glu Gln Phe Tyr Arg Val Gln Glu Ile Phe Ser Arg Met Gly Lys
                    245                 250                 255
    Asn Pro Asn Met Asn Arg Asp Ser Ala Ser Leu Leu Asn Asn Leu Val
                260                 265                 270
    Val Cys Gly Lys Cys Gly Leu Gly Phe Val His Arg Lys Asp Thr
            275                 280                 285
    Val Ser Arg Gly Lys Lys Tyr His Tyr Arg Tyr Ser Cys Lys Thr
        290                 295                 300
    Tyr Lys His Thr His Glu Leu Glu Lys Cys Gly Asn Lys Ile Trp Arg
    305                 310                 315                 320
    Ala Asp Lys Leu Glu Glu Leu Ile Ile Asp Arg Val Asn Asn Tyr Ser
                    325                 330                 335
    Phe Ala Ser Arg Asn Val Asp Lys Glu Asp Leu Asp Ser Leu Asn
                340                 345                 350
    Glu Lys Leu Lys Thr Glu His Val Lys Lys Arg Leu Phe Asp Leu
            355                 360                 365
    Tyr Ile Ser Gly Ser Tyr Glu Val Ser Glu Leu Asp Ala Met Met Ala
        370                 375                 380
    Asp Ile Asp Ala Gln Ile Asn Tyr Tyr Glu Ala Gln Ile Glu Ala Asn
    385                 390                 395                 400
    Glu Glu Leu Lys Lys Asn Lys Lys Ile Gln Glu Asn Leu Ala Asp Leu
                    405                 410                 415
    Ala Thr Val Asp Phe Asp Ser Leu Glu Phe Arg Glu Lys Gln Leu Tyr
                420                 425                 430
    Leu Lys Ser Leu Ile Asn Lys Ile Tyr Ile Asp Gly Glu Gln Val Thr
            435                 440                 445
    Ile Glu Trp Leu
        450
```

<210> SEQ ID NO 28
<211> LENGTH: 29
<212> TYPE: DNA
<213> ORGANISM: Artificial
<220> FEATURE:
<223> OTHER INFORMATION: Primer

<400> SEQUENCE: 28
gtagatctta actttccatg cgagaggag                        29

<210> SEQ ID NO 29
<211> LENGTH: 36
<212> TYPE: DNA
<213> ORGANISM: Artificial
<220> FEATURE:
<223> OTHER INFORMATION: Primer

<400> SEQUENCE: 29
gggcatgcga taaaaagcaa tctatagaaa aacagg                                    36

<210> SEQ ID NO 30
<211> LENGTH: 29
<212> TYPE: DNA
<213> ORGANISM: Artificial
<220> FEATURE:
<223> OTHER INFORMATION: Primer

<400> SEQUENCE: 30
cctaagcttt cgatcatcat aattctgtc                                            29

<210> SEQ ID NO 31
<211> LENGTH: 37
<212> TYPE: DNA
<213> ORGANISM: Artificial
<220> FEATURE:
<223> OTHER INFORMATION: Primer

<400> SEQUENCE: 31
gggcatgcag atcttttttt cagaaaatcc cagtacg                                   37

<210> SEQ ID NO 32
<211> LENGTH: 6116
<212> TYPE: DNA
<213> ORGANISM: Artificial
<220> FEATURE:
<223> OTHER INFORMATION: pPL2

<400> SEQUENCE: 32
gacgtcatta accctcacta aagggaacaa aagctggtac cgggcccccc ctcgaggtcg          60
acggtatcga taagcttgat atcgaattcc tgcagcccgg gggatccact agttctagag         120
cggccgccac cgcggtggag ctccaattcg ccctatagtg agtcgtattg acgtcgctat         180
ttaacgaccc tgccctgaac cgacgaccgg gtcgaatttg ctttcgaatt tctgccattc         240
atccgcttat tatcacttat tcaggcgtag caaccaggcg tttaagggca ccaataactg         300
ccttaaaaaa attacgcccc gccctgccac tcatcgcagt actgttgtaa ttcattaagc         360
attctgccga catggaagcc atcacaaacg gcatgatgaa cctgaatcgc cagcggcatc         420
agcaccttgt cgccttgcgt ataatatttg cccatggtga aacgggggc gaagaagttg          480 tccatattgg ccacgtttaa atcaaaactg gtgaaactca cccagggatt ggctgagacg         540
aaaaacatat tctcaataaa ccctttaggg aaataggcca ggttttcacc gtaacacgcc         600
acatcttgcg aatatatgtg tagaaactgc cggaaatcgt cgtggtattc actccagagc         660
gatgaaaacg tttcagtttg ctcatggaaa acggtgtaac aagggtgaac actatcccat         720
atcaccagct caccgtcttt cattgccata cggaattccg gatgagcatt catcaggcgg         780
gcaagaatgt gaataaaggc cggataaaac ttgtgcttat ttttctttac ggtctttaaa         840
aaggccgtaa tatccagctg aacggtctgg ttataggtac attgagcaac tgactgaaat         900
gcctcaaaat gttctttacg atgccattgg gatatatcaa cggtggtata tccagtgatt         960

```
tttttctcca ttttagcttc cttagctcct gaaaatctcg ataactcaaa aaatacgccc    1020
ggtagtgatc ttatttcatt atggtgaaag ttggaacctc ttacgtgccg atcaacgtct    1080
cattttcgcc aaaagttggc ccagggcttc ccggtatcaa caggacacc aggatttatt     1140 tattctgcga agtgatcttc cgtcacaggt atttattcgg cgcaaagtgc gtcgggtgat    1200
gctgccaact tactgattta gtgtatgatg gtgttttga ggtgctccag tggcttctgt     1260
ttctatcagc tgtccctcct gttcagctac tgacggggtg gtgcgtaacg gcaaaagcac    1320
cgccggacat cagcgctagc ggagtgtata ctggcttact atgttggcac tgatgagggt    1380
gtcagtgaag tgcttcatgt ggcaggagaa aaaaggctgc accggtgcgt cagcagaata    1440
tgtgatacag gatatattcc gcttcctcgc tcactgactc gctacgctcg gtcgttcgac    1500
tgcggcgagc ggaaatggct tacgaacggg gcggagattt cctggaagat gccaggaaga    1560
tacttaacag ggaagtgaga gggccgcggc aaagccgttt ttccataggc tccgcccccc    1620
tgacaagcat cacgaaatct gacgctcaaa tcagtggtgg cgaaacccga caggactata    1680
aagataccag gcgttttccc ctggcggctc cctcgtgcgc tctcctgttc ctgcctttcg    1740
gtttaccggt gtcattccgc tgttatggcc gcgtttgtct cattccacgc tgacactca     1800 gttccgggta ggcagttcgc tccaagctgg actgtatgca cgaaccccc  gttcagtccg    1860 accgctgcgc cttatccggt aactatcgtc ttgagtccaa cccggaaaga catgcaaaag    1920
caccactggc agcagccact ggtaattgat ttagaggagt tagtcttgaa gtcatgcgcc    1980
ggttaaggct aaactgaaag gacaagtttt ggtgactgcg ctcctccaag ccagttacct    2040
cggttcaaag agttggtagc tcagagaacc ttcgaaaaac cgccctgcaa ggcggttttt    2100
tcgttttcag agcaagagat tacgcgcaga ccaaaacgat ctcaagaaga tcatcttatt    2160
aatcagataa atatttccta gatttcagtg caatttatct cttcaaatgt agcacctgaa    2220
gtcagcccca tacgatataa gttgtaattc tccgccgctt gccctcatct gttacgccgg    2280
cggtagccgg ccagcctcgc agagcaggat tcccgttgag caccgccagg tgcgaataag    2340
ggacagtgaa gaggaacac  ccgctcgcgg gtgggcctac ttacctatc  ctgcccggct    2400 gacgccgttg gatacaccaa ggaaagtcta cacgaaccct ttgcaaaat  cctgtatatc    2460 gtgcgaaaaa ggatggatat accgaaaaaa tcgctataat gaccccgaag cagggttatg    2520
cagcggaaaa gcgctgcttc cctgctgttt tgtggaatat ctaccgactg gaaacaggca    2580
aatgcaggaa attactgaac tgaggggaca ggcgagaggc atgcgtggag ggaaagaaga    2640
acgctgttga aaaaatcttc tctggactac ttgaaacaaa agaattaaag tcatttata     2700 aaaaccttga gaaaaacat  cttgatataa aaactattta taacgaatat ttatttcaat    2760
gtaataataa ataatattta ttattacata aaatgtttgt ggtattattt gtggtatata    2820
tatcctaaat ggctttatat cagtgtgtgt taatccctct caggacgtta aatagtaatg    2880
taaagaaatc tctaaaacgt tgaaaagcct tgatattaaa gggcggatga atgttttgga    2940
gtttttttta tatcgtataa tacccgtttt attccgttgt ttttgtggca tttgtggtaa    3000
aatttgtggt attttcatct gtttttagtg tgaaaaaagc atctactttg gactgattat    3060
gttgtcttaa attagagctt agatgactat agtattttaa tgttgtatta atgtcatcat    3120
gaccaagcct atcagctaca taaataatat ccatacccgc ttctacacat aagcctgtat    3180
gcgtatgtcg tagcttgtgt aatgtcactg gttcagaatt gattgtacta catatcttct    3240
tcaaagcttt attacaagac gcgttgtcta ctggcttatt gtggtaagtg atgaataata    3300
acatcaatgg attcttaata gcatgttcct tcatatattc agtatgccaa tttaaatacg    3360
```

```
aatgtaaata ttgagcggta gagttatcaa tatagatcac tcgtgatttt tttgttttgg   3420
tatcaatgaa tgtattagtg tacttgtaat cccaagcttt attcacagtt attgaacgtt   3480
tagtgaaatt aatatccttc tttgttagtg caataatttc ttcgaacctc atgcctgtct   3540
ggacagctag aaagataact gctcgtgata tagaatgaaa ttttgcaagt tcttctaata   3600
gtaaatgaac tttgtctgtt tccataaatt gtgctttatt tttcgctacg tcctgtccgc   3660
ttatatgagc ccctatagtg gggttttttct tcatgtaacc taaatgaaca gccttgttaa   3720
aaatcgctct aattttgcgg tgtctggtgt ctacagtgga tattgcatag tctacagata   3780
aatgattaat aaattgttga tattgaaccg catcaatcga attaaattta attttttcat   3840
cgaaataatc aacgaattga ttataagcaa gatcgtataa attaatagta gattgactac   3900
ttttcccatc tttaaatgtt ttcatgaata gcgtataaaa ttctttgaag ttccattctt   3960
tcagagaact actatcatgc tgaacttgtt ttaataattt agatgcttta tacattaagt   4020
ttgtttcact tgtatctgtc aaacgctttt cttttccattc accatcgact tttatacgta   4080
ggcgaacaca atatttaccg tttgctaatt tttttatctt cattaatacc accacctgtt   4140 tattttttgga gatcttttttt tcagaaaatc ccagtacgta attaagtatt tgagaattaa   4200
ttttatattg attaatacta agtttaccca gttttcacct aaaaaacaaa tgatgagata   4260
atagctccaa aggctaaaga ggactatacc aactatttgt aataattctg taacagttga   4320
aaagcgaacg tgtattctta gggcttgaga tgtattgctg ggtaaacctt tatagtgtaa   4380
gtgggatgtg aacgttaatc aacaactttc gctatgggaa acctattgtt ttttgttaat   4440
agaaaaactt aatacatttg taatataaaa accggcagtt tttccgttct tcgtgactcg   4500
aaatgaattg ccagatgagt ttatggtatt ctataataga aggtatggag gatgttatat   4560
aatgagacag aattatgatg atcgaaagct agcttggcac tggccgtcgt tttacaacgt   4620
cgtgactggg aaaaccctgg cgttacccaa cttaatcgcc ttgcagcaca tccccctttc   4680
gccagctggc gtaatagcga agaggcccgc accgatcgcc cttcccaaca gttgcgcagc   4740
ctgaatggcg aatggcgcct gatgcggtat tttctcctta cgcatctgtg cggtatttca   4800
caccgcatat gatcccggat ctggagctgt aatataaaaa ccttcttcaa ctaacggggc   4860
aggttagtga cattagaaaa ccgactgtaa aaagtacagt cggcattatc tcatattata   4920
aaagccagtc attaggccta tctgacaatt cctgaataga gttcataaac aatcctgcat   4980
gataaccatc acaaacagaa tgatgtacct gtaaagatag cggtaaatat attgaattac   5040
ctttattaat gaatttttcct gctgtaataa tgggtagaag gtaattacta ttattattga   5100
tatttaagtt aaacccagta aatgaagtcc atggaataat agaaagagaa aaagcatttt   5160
caggtatagg tgttttggga aacaatttcc ccgaaccatt atatttctct acatcagaaa   5220
ggtataaatc ataaaactct ttgaagtcat tctttacagg agtccaaata ccagagaatg   5280
ttttagatac accatcaaaa attgtataaa gtggctctaa cttatcccaa taacctaact   5340
ctccgtcgct attgtaacca gttctaaaag ctgtatttga gtttatcacc cttgtcacta   5400
agaaaataaa tgcagggtaa aatttatatc cttcttgttt tatgtttcgg tataaaacac   5460
taatatcaat ttctgtggtt atactaaaag tcgtttgttg gttcaaataa tgattaaata   5520
tctcttttct cttccaattg tctaaatcaa ttttattaaa gttcatttga tatgcctcct   5580 aaattttat ctaaagtgaa tttaggaggc ttacttgtct gctttcttca ttagaatcaa   5640
tcctttttta aaagtcaata ttactgtaac ataaatatat attttaaaaa tatcccactt   5700
```

-continued

```
tatccaattt tcgtttgttg aactaatggg tgctttagtt gaagaataaa agaccacatt    5760
aaaaaatgtg gtcttttgtg ttttttttaaa ggatttgagc gtagcgaaaa atccttttct   5820
ttcttatctt gataataagg gtaactattg cccagatccg ggatcatatg gtgcactctc    5880
agtacaatct gctctgatgc cgcatagtta agccagcccc gacacccgcc aacacccgct    5940
gacgcgccct gacgggcttg tctgctcccg gcatccgctt acagacaagc tgtgaccgtc    6000
tccgggagct gcatgtgtca gaggttttca ccgtcatcac cgaaacgcgc gagacgaaag    6060
ggcctcgtga tacgcctatt tttataggtt aatgtcatga taataatggt ttctta        6116
```

<210> SEQ ID NO 33
<211> LENGTH: 24
<212> TYPE: DNA
<213> ORGANISM: Artificial
<220> FEATURE:
<223> OTHER INFORMATION: PL95 primer

<400> SEQUENCE: 33
acataatcag tccaaagtag atgc    24

<210> SEQ ID NO 34
<211> LENGTH: 21
<212> TYPE: DNA
<213> ORGANISM: Artificial
<220> FEATURE:
<223> OTHER INFORMATION: Primer

<400> SEQUENCE: 34
acgaatgtaa atattgagcg g    21

<210> SEQ ID NO 35
<211> LENGTH: 29
<212> TYPE: DNA
<213> ORGANISM: Artificial
<220> FEATURE:
<223> OTHER INFORMATION: Primer

<400> SEQUENCE: 35
catgcatgcg tggagggaaa gaagaacgc    29

<210> SEQ ID NO 36
<211> LENGTH: 18
<212> TYPE: DNA
<213> ORGANISM: Artificial
<220> FEATURE:
<223> OTHER INFORMATION: PL94 primer

<400> SEQUENCE: 36
ggagggaaag aagaacgc    18

<210> SEQ ID NO 37
<211> LENGTH: 24
<212> TYPE: DNA
<213> ORGANISM: Artificial
<220> FEATURE:
<223> OTHER INFORMATION: PL102 primer

<400> SEQUENCE: 37
tatcagacct aacccaaacc ttcc    24

<210> SEQ ID NO 38
<211> LENGTH: 24
<212> TYPE: DNA
<213> ORGANISM: Artificial

```
<220> FEATURE:
<223> OTHER INFORMATION: PL103 primer

<400> SEQUENCE: 38
aatcgcaaaa taaaaatctt ctcg                                          24

<210> SEQ ID NO 39
<211> LENGTH: 21
<212> TYPE: DNA
<213> ORGANISM: Artificial
<220> FEATURE:
<223> OTHER INFORMATION: NC16 primer

<400> SEQUENCE: 39
gtcaaaacat acgctcttat c                                             21

<210> SEQ ID NO 40
<211> LENGTH: 43
<212> TYPE: DNA
<213> ORGANISM: Artificial
<220> FEATURE:
<223> OTHER INFORMATION: Primer

<400> SEQUENCE: 40
atccctcgag ctcagagcgg ccgcactagt cccggggagc tcg                     43

<210> SEQ ID NO 41
<211> LENGTH: 54
<212> TYPE: DNA
<213> ORGANISM: Artificial
<220> FEATURE:
<223> OTHER INFORMATION: Primer

<400> SEQUENCE: 41
tcgacgagct ccccgggact agtgcggccg ctctgagctc gagggatccg acgt         54

<210> SEQ ID NO 42
<211> LENGTH: 50
<212> TYPE: DNA
<213> ORGANISM: Bacteriophage A118

<400> SEQUENCE: 42 tttagttct cgtttcttct tcttccaacg agagaaaacg aggaactaaa               50

<210> SEQ ID NO 43
<211> LENGTH: 95
<212> TYPE: DNA
<213> ORGANISM: Bacteriophage PSA

<400> SEQUENCE: 43
ttacataaaa tgtttgtggt attatttgtg gtatatatat cctaaatggc tttatatcag   60
tgtgtgttaa tccctctcag gacgttaaat agtaa                              95

<210> SEQ ID NO 44
<211> LENGTH: 1698
<212> TYPE: DNA
<213> ORGANISM: Listeria monocytogenes
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (1534)..(1534)
<223> OTHER INFORMATION: n is a, c, g, or t
```

<400> SEQUENCE: 44

```
ttacataaaa tgtttgtggt attatttgtg gtattccaaa aaaacttaag aaggttctta       60
cnattcttag tttttcatat attcttactc caaaaagcta ggcatttccc tgtgaatttt      120
attcatttt  tctgtaagtt tcataaattc cgctttgttc ctattatcga gagctttatc      180
aatttcagct ctaagttgtt ctaattttct ctcttctagg agcatcgtca ggaagcattc      240
gataaaaacg tttgttaatt cttttcacc  cttaaggaca cccacctgat tcatcaacga      300
attagaaaaa tcacgcattt ccacgactac cactccttca ctcatatta ttacaatctt       360
aaaaaattgt aatatgccaa gaaaaacag aaacagctt  gaaatacaa ctttactaat        420
atctaatgac ttgcaaatta ccatgtgcta taatgacaaa aaataactca taactaactt      480
tgatgcttag tcgttactta gaagttttgc ttattaggca ataactctag gtttcttctt      540
agacataaat acaaacatag aggagttgaa tgaaatgaaa aagaacaaa  tcagtactca      600
gttttatgaa gtaaacccgc acacgatgat tattttttca aaaaaatctg gaagtatagt      660
ctattcagaa atttatgaag ttgattctca ttatacttct aaatttaccc cgtttgagct      720
aattaaaacc agctgtaact ttttcggatc aagctatgaa ggacgcaaag agggaactaa      780
acacttaatt ggtgttaccc ataagccacc cattatcatt gacccagtca cttctactta      840
tgtatttcca actgtagcac caagttcaac agaatgcatt tggattttcc cacaacatat      900
taaagattat catgcaattg gatttaacca cactttaata acattttcta atatggaaac      960
ctttgagatt gatatgtctt tagcatcttt taataatcag attgccagaa cctccatgtt     1020
acatatgaaa ttttctcaaa aaatgcgtat gatggagagt aatttcccct caatgaatag     1080
gttttttccca ccaaccactc ttgctgctga acctaagacg ttattacagc accatgcttc    1140
caaataatga agaacctaat gatcctcaag atcccgagca ataaatttaa aactaaataa     1200
aagccagcta cgtaatagta gctggctttt ccttaaaatc attttttatt ctcaatcgca     1260
tctgcaattc gttttaacat taataactca tcctctgagt atgtataagg tagttctaaa     1320
taccattct  cgagttcagg atttccaatt aaaggaaagg cgtttaccga attctttct       1380
cgcaaaccag ctacatcatc taataagaaa tcggttgttg ttccaagaat ttctgctaat     1440
ttagccaaaa taaaaattgg cggtcggtgg ttatcatttt catacttgct tattgtggat     1500
gcagttgtcc cgatttttcgc cgccagttgt ttttntgtgtt aacctatttt tctttcgtaa   1560
atgaattaat ttttctccaa attccaatac gcccacctca cttccttcca gtatagcaat     1620
ttttcggaaa gaattcgaga aattctaaaa agaaatcgct tttttaggtttt caaaagacat   1680
tttcccgtat ttatacag                                                    1698
```

<210> SEQ ID NO 45
<211> LENGTH: 90
<212> TYPE: DNA
<213> ORGANISM: Listeria monocytogenes

<400> SEQUENCE: 45

```
tgtcctgata gctcagctgg atagagcaac ggccttctaa gccgtcggtc gggggttcga       60
atccctctca ggacgtaaat agctatatta                                       90
```

<210> SEQ ID NO 46
<211> LENGTH: 1155
<212> TYPE: DNA
<213> ORGANISM: Bacteriophage PSA

<400> SEQUENCE: 46

```
ttattccgtt gttttttgtgg catttgtggt aaaatttgtg gtattttcat ctgtttttag      60
tgtgaaaaaa gcatctactt tggactgatt atgttgtctt aaattagagc ttagatgact     120
atagtatttt aatgttgtat taatgtcatc atgaccaagc ctatcagcta cataaataat     180
atccataccc gcttctacac ataagcctgt atgcgtatgt cgtagcttgt gtaatgtcac     240
tggttcagaa ttgattgtac tacatatctt cttcaaagct ttattacaag acgcgttgtc     300
tactggctta ttgtggtaag tgatgaataa taacatcaat ggattcttaa tagcatgttc     360
cttcatataa tcagtatgcc aatttaaata cgaatgtaaa tattgagcgg tagagttatc     420
aatatagatc actcgtgatt tttttgtttt ggtatcaatg aatgtattag tgtacttgta     480
atcccaagct ttattcacag ttattgaacg tttagtgaaa ttaatatcct tctttgttag     540
tgcaataatt tcttcgaacc tcatgcctgt ctggacagct agaaagataa ctgctcgtga     600
tatagaatga aattttgcaa gttcttctaa tagtaaatga actttgtctg tttccataaa     660
ttgtgcttta ttttttcgcta cgtcctgtcc gcttatatga gcccctatag tggggttttt     720
cttcatgtaa cctaaatgaa cagccttgtt aaaaatcgct ctaattttgc ggtgtctggt     780
gtctacagtg gatattgcat agtctacaga taaatgatta ataaattgtt gatattgaac     840
cgcatcaatc gaattaagtt taattttttc atcgaaataa tcaacgaatt gattataagc     900
aagatcgtat aaattaatag tagattgact acttttccca tctttaaatg ttttcatgaa     960
tagcgtataa aattctttga agttccattc tttcagagaa ctactatcat gctgaacttg    1020
ttttaataat ttagatgctt tatacattaa gtttgtttca cttgtatctg tcaaacgctt    1080
ttctttccat tcaccatcga cttttatacg taggcgaaca caatatttac cgtttgctaa    1140 ttttttatc ttcat                                                      1155

<210> SEQ ID NO 47
<211> LENGTH: 384
<212> TYPE: PRT
<213> ORGANISM: Bacteriophage PSA

<400> SEQUENCE: 47

Met Lys Ile Lys Lys Leu Ala Asn Gly Lys Tyr Cys Val Arg Leu Arg
1               5                   10                  15

Ile Lys Val Asp Gly Glu Trp Lys Glu Lys Arg Leu Thr Asp Thr Ser
            20                  25                  30

Glu Thr Asn Leu Met Tyr Lys Ala Ser Lys Leu Leu Lys Gln Val Gln
        35                  40                  45

His Asp Ser Ser Ser Leu Lys Glu Trp Asn Phe Lys Glu Phe Tyr Thr
    50                  55                  60

Leu Phe Met Lys Thr Phe Lys Asp Gly Lys Ser Ser Gln Ser Thr Ile
65                  70                  75                  80

Asn Leu Tyr Asp Leu Ala Tyr Asn Gln Phe Val Asp Tyr Phe Asp Glu
                85                  90                  95

Lys Ile Lys Leu Asn Ser Ile Asp Ala Val Gln Tyr Gln Gln Phe Ile
            100                 105                 110

Asn His Leu Ser Val Asp Tyr Ala Ile Ser Thr Val Asp Thr Arg His
        115                 120                 125

Arg Lys Ile Arg Ala Ile Phe Asn Lys Ala Val His Leu Gly Tyr Met
    130                 135                 140

Lys Lys Asn Pro Thr Ile Gly Ala His Ile Ser Gly Gln Asp Val Ala
145                 150                 155                 160
```

```
Lys Asn Lys Ala Gln Phe Met Glu Thr Asp Lys Val His Leu Leu Leu
                165                 170                 175
Glu Glu Leu Ala Lys Phe His Ser Ile Ser Arg Ala Val Ile Phe Leu
            180                 185                 190
Ala Val Gln Thr Gly Met Arg Phe Glu Glu Ile Ala Leu Thr Lys
        195                 200                 205
Lys Asp Ile Asn Phe Thr Lys Arg Ser Ile Thr Val Asn Lys Ala Trp
210                 215                 220
Asp Tyr Lys Tyr Thr Asn Thr Phe Ile Asp Thr Lys Thr Lys Ser
225                 230                 235                 240
Arg Val Ile Tyr Ile Asp Asn Ser Thr Ala Gln Tyr Leu His Ser Tyr
                245                 250                 255
Leu Asn Trp His Thr Asp Tyr Met Lys Glu His Ala Ile Lys Asn Pro
            260                 265                 270
Leu Met Leu Leu Phe Ile Thr Tyr His Asn Lys Pro Val Asp Asn Ala
        275                 280                 285
Ser Cys Asn Lys Ala Leu Lys Lys Ile Cys Ser Thr Ile Asn Ser Glu
290                 295                 300
Pro Val Thr Leu His Lys Leu Arg His Thr His Thr Gly Leu Cys Val
305                 310                 315                 320
Glu Ala Gly Met Asp Ile Ile Tyr Val Ala Asp Arg Leu Gly His Asp
                325                 330                 335
Asp Ile Asn Thr Thr Leu Lys Tyr Tyr Ser His Leu Ser Ser Asn Leu
            340                 345                 350
Arg Gln His Asn Gln Ser Lys Val Asp Ala Phe Phe Thr Leu Lys Thr
        355                 360                 365
Asp Glu Asn Thr Thr Asn Phe Thr Thr Asn Ala Thr Lys Thr Thr Glu
370                 375                 380

<210> SEQ ID NO 48
<211> LENGTH: 1370
<212> TYPE: DNA
<213> ORGANISM: Bacteriophage A118

<400> SEQUENCE: 48
caagctacta gagccattca atagtaactt gttcaccatc aatataaatt ttgttttatta      60
gtgattttaa ataaagttgc ttttctctga actctaaaga gtcaaaatca actgttgcta     120
aatcagctaa attttcttgt atctttttgt ttttcttcaa ttcttcgtta gcttctattt     180
gtgattcata ataattaatt tgagcatcaa tatcattcat catagaatca agttctgaaa     240
cttcatacga gccatttata tataaatcaa ataatcgttt tttctttgca tgttctattt     300
taagcttttc atttaagcta tctaattcat cttctttatc tacatttctg gaagcgaaac     360
tataattatt cacacgatta ataattaatt cttcaagttt gtcagctctc caaattttat     420
tcccgcattt ttcgagttca tgagtatgtt tataagtctt gcaactataa atctataat      480
gatatttttt accacgcgac attgtatctt ttctacgatg aacaaagcct aacccgcatt     540
tactacaaac tactaaatta tttagcaacg atgctgaatc tctattcatg ttcggatttt     600
tacccatacg agtaaatatt tcttgaactc tatagaattg ctcttcactg atgataggtt     660
catgaatacc ttttcatga  actttatctt tatatgaaac ataaccacaa tacaaatcat     720
tagttagcca gttgttatag cgattatatg ttctaacttt aaagcctaat ttttttagtc     780
ttttctgtaa aaaagttata ctttgttctt cttcgaaaat atcataaatc agttgtaact     840
gttttgcttc ttcttcatta atgtataatt ttgtatctat aacatcatag ccgaacgttc     900
```

-continued

```
taccttttcgc agttgttaac ggaagacctg cttcaatacg cttaattttc cccatcacca    960
tacgatctcg gattgtttcg cgctctagct gtgcgaatac tgataatata ccaatcattg   1020
cacgaccgaa aggggaacta gtatcaagcg tttcagacaa actaacaaac tctacattgt   1080
tttttaagaa gtattcttca ataagcgtta ttgtgtctct ttgtgagcgg gatagtctgt   1140
ctaatcgata tacgactaca gcatcaattt cgtgtagttt acttagcatt tcatttaatg   1200
cgggacgatt catatttgag ccggagtatc cgccgtcaat gaaaatatcg tatacgtccc   1260
agtccttcga gcggcacaat gctgttagtt tttcagtttg agcttgtatt gaataatttt   1320
ctacttgctc ttgagtagaa acacgtatat aaatagctgc cttcatttcc              1370
```

<210> SEQ ID NO 49
<211> LENGTH: 452
<212> TYPE: PRT
<213> ORGANISM: Bacteriophage A118

<400> SEQUENCE: 49

```
Met Lys Ala Ala Ile Tyr Ile Arg Val Ser Thr Gln Glu Gln Val Glu
1               5                   10                  15

Asn Tyr Ser Ile Gln Ala Gln Thr Glu Lys Leu Thr Ala Leu Cys Arg
            20                  25                  30

Ser Lys Asp Trp Asp Val Tyr Asp Ile Phe Ile Asp Gly Gly Tyr Ser
        35                  40                  45

Gly Ser Asn Met Asn Arg Pro Ala Leu Asn Glu Met Leu Ser Lys Leu
    50                  55                  60

His Glu Ile Asp Ala Val Val Tyr Arg Leu Asp Arg Leu Ser Arg
65                  70                  75                  80

Ser Gln Arg Asp Thr Ile Thr Leu Ile Glu Glu Tyr Phe Leu Lys Asn
                85                  90                  95

Asn Val Glu Phe Val Ser Leu Ser Glu Thr Leu Asp Thr Ser Ser Pro
            100                 105                 110

Phe Gly Arg Ala Met Ile Gly Ile Leu Ser Val Phe Ala Gln Leu Glu
        115                 120                 125

Arg Glu Thr Ile Arg Asp Arg Met Val Met Gly Lys Ile Lys Arg Ile
    130                 135                 140

Glu Ala Gly Leu Pro Leu Thr Thr Ala Lys Gly Arg Thr Phe Gly Tyr
145                 150                 155                 160

Asp Val Ile Asp Thr Lys Leu Tyr Ile Asn Glu Glu Glu Ala Lys Gln
                165                 170                 175

Leu Gln Leu Ile Tyr Asp Ile Phe Glu Glu Glu Gln Ser Ile Thr Phe
            180                 185                 190

Leu Gln Lys Arg Leu Lys Lys Leu Gly Phe Lys Val Arg Thr Tyr Asn
        195                 200                 205

Arg Tyr Asn Asn Trp Leu Thr Asn Asp Leu Tyr Cys Gly Tyr Val Ser
    210                 215                 220

Tyr Lys Asp Lys Val His Val Lys Gly Ile His Glu Pro Ile Ile Ser
225                 230                 235                 240

Glu Glu Gln Phe Tyr Arg Val Gln Glu Ile Phe Thr Arg Met Gly Lys
                245                 250                 255

Asn Pro Asn Met Asn Arg Asp Ser Ala Ser Leu Leu Asn Asn Leu Val
            260                 265                 270

Val Cys Ser Lys Cys Gly Leu Gly Phe Val His Arg Arg Lys Asp Thr
        275                 280                 285
```

```
Met Ser Arg Gly Lys Lys Tyr His Tyr Arg Tyr Tyr Ser Cys Lys Thr
    290                 295                 300
Tyr Lys His Thr His Glu Leu Glu Lys Cys Gly Asn Lys Ile Trp Arg
305                 310                 315                 320
Ala Asp Lys Leu Glu Glu Leu Ile Ile Asn Arg Val Asn Asn Tyr Ser
                325                 330                 335
Phe Ala Ser Arg Asn Val Asp Lys Glu Asp Glu Leu Asp Ser Leu Asn
            340                 345                 350
Glu Lys Leu Lys Ile Glu His Ala Lys Lys Lys Arg Leu Phe Asp Leu
        355                 360                 365
Tyr Ile Asn Gly Ser Tyr Glu Val Ser Glu Leu Asp Ser Met Met Asn
    370                 375                 380
Asp Ile Asp Ala Gln Ile Asn Tyr Tyr Glu Ser Gln Ile Glu Ala Asn
385                 390                 395                 400
Glu Glu Leu Lys Lys Asn Lys Lys Ile Gln Glu Asn Leu Ala Asp Leu
                405                 410                 415
Ala Thr Val Asp Phe Asp Ser Leu Glu Phe Arg Glu Lys Gln Leu Tyr
            420                 425                 430
Leu Lys Ser Leu Ile Asn Lys Ile Tyr Ile Asp Gly Glu Gln Val Thr
        435                 440                 445
Ile Glu Trp Leu
    450
```

<210> SEQ ID NO 50
<211> LENGTH: 1107
<212> TYPE: DNA
<213> ORGANISM: Listeria monocytogenes

<400> SEQUENCE: 50

```
atggtgacag gctggcatcg tccaacatgg attgaaatag accgcgcagc aattcgcgaa      60
aatataaaaa atgaacaaaa taaactcccg gaaagtgtcg acttatgggc agtagtcaaa     120
gctaatgcat atggtcacgg aattatcgaa gttgctagga cggcgaaaga agctggagca     180
aaaggtttct gcgtagccat tttagatgag gcactggctc ttagagaagc tggatttcaa     240
gatgacttta ttcttgtgct tggtgcaacc agaaagaag atgctaatct ggcagccaaa      300
aaccacattt cacttactgt ttttagaaa gattggctag agaatctaac gctagaagca      360
acacttcgaa ttcatttaaa agtagatagc ggtatggggc gtctcggtat tcgtacgact     420
gaagaagcac ggcgaattga agcaaccagt actaatgatc accaattaca actggaaggt     480
atttacacgc attttgcaac agccgaccag ctagaaacta gttattttga caacaatta      540
gctaagttcc aaacgatttt aacgagttta aaaaaacgac caactatgt tcatacagcc      600
aattcagctg cttcattgtt acagccacaa atcgggtttg atgcgattcg ctttggtatt     660
tcgatgtatg gattaactcc ctccacagaa atcaaaacta gcttgccgtt tgagcttaaa     720
cctgcacttg cactctatac cgagatggtt catgtgaaag aacttgcacc aggcgatagc     780
gttagctacg gagcaactta tacagcaaca gagcgagaat gggttgcgac attaccaatt     840
ggctatgcgg atggattgat tcgtcattac agtggtttcc atgttttagt agacggtgaa     900
ccagctccaa tcattggtcg agtttgtatg gatcaaacca tcataaaact accacgtgaa     960
tttcaaactg gttcaaaagt aacgataatt ggcaaagatc atggtaacac ggtaacagca    1020
gatgatgccg ctcaatattt agatacaatt aattatgagg taacttgttt gttaaatgag    1080
cgcataccta gaaaatacat ccattag                                        1107
```

<210> SEQ ID NO 51
<211> LENGTH: 368
<212> TYPE: PRT
<213> ORGANISM: Listeria monocytogenes

<400> SEQUENCE: 51

Met Val Thr Gly Trp His Arg Pro Thr Trp Ile Glu Ile Asp Arg Ala
1               5                   10                  15

Ala Ile Arg Glu Asn Ile Lys Asn Glu Gln Asn Lys Leu Pro Glu Ser
            20                  25                  30

Val Asp Leu Trp Ala Val Val Lys Ala Asn Ala Tyr Gly His Gly Ile
        35                  40                  45

Ile Glu Val Ala Arg Thr Ala Lys Glu Ala Gly Ala Lys Gly Phe Cys
    50                  55                  60

Val Ala Ile Leu Asp Glu Ala Leu Ala Leu Arg Glu Ala Gly Phe Gln
65                  70                  75                  80

Asp Asp Phe Ile Leu Val Leu Gly Ala Thr Arg Lys Glu Asp Ala Asn
                85                  90                  95

Leu Ala Ala Lys Asn His Ile Ser Leu Thr Val Phe Arg Glu Asp Trp
            100                 105                 110

Leu Glu Asn Leu Thr Leu Glu Ala Thr Leu Arg Ile His Leu Lys Val
        115                 120                 125

Asp Ser Gly Met Gly Arg Leu Gly Ile Arg Thr Thr Glu Glu Ala Arg
    130                 135                 140

Arg Ile Glu Ala Thr Ser Thr Asn Asp His Gln Leu Gln Leu Glu Gly
145                 150                 155                 160

Ile Tyr Thr His Phe Ala Thr Ala Asp Gln Leu Glu Thr Ser Tyr Phe
                165                 170                 175

Glu Gln Gln Leu Ala Lys Phe Gln Thr Ile Leu Thr Ser Leu Lys Lys
            180                 185                 190

Arg Pro Thr Tyr Val His Thr Ala Asn Ser Ala Ala Ser Leu Leu Gln
        195                 200                 205

Pro Gln Ile Gly Phe Asp Ala Ile Arg Phe Gly Ile Ser Met Tyr Gly
    210                 215                 220

Leu Thr Pro Ser Thr Glu Ile Lys Thr Ser Leu Pro Phe Glu Leu Lys
225                 230                 235                 240

Pro Ala Leu Ala Leu Tyr Thr Glu Met Val His Val Lys Glu Leu Ala
                245                 250                 255

Pro Gly Asp Ser Val Ser Tyr Gly Ala Thr Tyr Thr Ala Thr Glu Arg
            260                 265                 270

Glu Trp Val Ala Thr Leu Pro Ile Gly Tyr Ala Asp Gly Leu Ile Arg
        275                 280                 285

His Tyr Ser Gly Phe His Val Leu Val Asp Gly Glu Pro Ala Pro Ile
    290                 295                 300

Ile Gly Arg Val Cys Met Asp Gln Thr Ile Ile Lys Leu Pro Arg Glu
305                 310                 315                 320

Phe Gln Thr Gly Ser Lys Val Thr Ile Ile Gly Lys Asp His Gly Asn
                325                 330                 335

Thr Val Thr Ala Asp Asp Ala Ala Gln Tyr Leu Asp Thr Ile Asn Tyr
            340                 345                 350

Glu Val Thr Cys Leu Leu Asn Glu Arg Ile Pro Arg Lys Tyr Ile His
        355                 360                 365

<210> SEQ ID NO 52

```
<211> LENGTH: 870
<212> TYPE: DNA
<213> ORGANISM: Listeria monocytogenes

<400> SEQUENCE: 52
atgaaagtat tagtaaataa ccatttagtt gaaagagaag atgccacagt tgacattgaa    60
gaccgcggat atcagtttgg tgatggtgta tatgaagtag ttcgtctata taatggaaaa   120
ttctttactt ataatgaaca cattgatcgc ttatatgcta gtgcagcaaa aattgactta   180
gttattcctt attccaaaga agagctacgt gaattacttg aaaaattagt tgccgaaaat   240
aatatcaata cagggaatgt ctatttacaa gtgactcgtg gtgttcaaaa cccacgtaat   300
catgtaatcc ctgatgattt ccctctagaa ggcgttttaa cagcagcagc tcgtgaagta   360
cctagaaacg agcgtcaatt cgttgaaggt ggaacggcga ttacagaaga agatgtgcgc   420
tggttacgct gtgatattaa gagcttaaac cttttaggaa atattctagc aaaaaataaa   480
gcacatcaac aaaatgcttt ggaagctatt ttacatcgcg gggaacaagt aacagaatgt   540
tctgcttcaa acgtttctat tattaaagat ggtgtattat ggacgcatgc ggcagataac   600
ttaatcttaa atggtatcac tcgtcaagtt atcattgatg ttgcgaaaaa gaatggcatt   660
cctgttaaag aagcggattt cactttaaca gaccttcgtg aagcggatga agtgttcatt   720
tcaagtacaa ctattgaaat tacacctatt acgcatattg acggagttca gtagctgac    780 ggaaaacgtg gaccaattac agcgcaactt catcaatatt ttgtagaaga aatcactcgt   840
gcatgtggcg aattagagtt tgcaaaataa                                    870

<210> SEQ ID NO 53
<211> LENGTH: 289
<212> TYPE: PRT
<213> ORGANISM: Listeria monocytogenes

<400> SEQUENCE: 53

Met Lys Val Leu Val Asn Asn His Leu Val Glu Arg Glu Asp Ala Thr
1               5                   10                  15

Val Asp Ile Glu Asp Arg Gly Tyr Gln Phe Gly Asp Gly Val Tyr Glu
            20                  25                  30

Val Val Arg Leu Tyr Asn Gly Lys Phe Phe Thr Tyr Asn Glu His Ile
        35                  40                  45

Asp Arg Leu Tyr Ala Ser Ala Ala Lys Ile Asp Leu Val Ile Pro Tyr
    50                  55                  60

Ser Lys Glu Glu Leu Arg Glu Leu Leu Glu Lys Leu Val Ala Glu Asn
65                  70                  75                  80

Asn Ile Asn Thr Gly Asn Val Tyr Leu Gln Val Thr Arg Gly Val Gln
                85                  90                  95

Asn Pro Arg Asn His Val Ile Pro Asp Asp Phe Pro Leu Glu Gly Val
            100                 105                 110

Leu Thr Ala Ala Ala Arg Glu Val Pro Arg Asn Glu Arg Gln Phe Val
        115                 120                 125

Glu Gly Gly Thr Ala Ile Thr Glu Glu Asp Val Arg Trp Leu Arg Cys
    130                 135                 140

Asp Ile Lys Ser Leu Asn Leu Leu Gly Asn Ile Leu Ala Lys Asn Lys
145                 150                 155                 160

Ala His Gln Gln Asn Ala Leu Glu Ala Ile Leu His Arg Gly Glu Gln
                165                 170                 175

Val Thr Glu Cys Ser Ala Ser Asn Val Ser Ile Ile Lys Asp Gly Val
            180                 185                 190
```

```
Leu Trp Thr His Ala Ala Asp Asn Leu Ile Leu Asn Gly Ile Thr Arg
            195                 200                 205

Gln Val Ile Ile Asp Val Ala Lys Lys Asn Gly Ile Pro Val Lys Glu
        210                 215                 220

Ala Asp Phe Thr Leu Thr Asp Leu Arg Glu Ala Asp Glu Val Phe Ile
225                 230                 235                 240

Ser Ser Thr Thr Ile Glu Ile Thr Pro Ile Thr His Ile Asp Gly Val
                245                 250                 255

Gln Val Ala Asp Gly Lys Arg Gly Pro Ile Thr Ala Gln Leu His Gln
            260                 265                 270

Tyr Phe Val Glu Glu Ile Thr Arg Ala Cys Gly Glu Leu Glu Phe Ala
        275                 280                 285

Lys

<210> SEQ ID NO 54
<211> LENGTH: 24
<212> TYPE: DNA
<213> ORGANISM: Artificial
<220> FEATURE:
<223> OTHER INFORMATION: Primer

<400> SEQUENCE: 54
ggtctagatc aagcacatac ctag                                              24

<210> SEQ ID NO 55
<211> LENGTH: 25
<212> TYPE: DNA
<213> ORGANISM: Artificial
<220> FEATURE:
<223> OTHER INFORMATION: Primer

<400> SEQUENCE: 55
cgggatcctg aagcttggga agcag                                             25

<210> SEQ ID NO 56
<211> LENGTH: 529
<212> TYPE: PRT
<213> ORGANISM: Listeria monocytogenes

<400> SEQUENCE: 56

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140
```

```
Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
            165                 170                 175

Asn Val Asn Asn Ala Val Asn Thr Leu Val Glu Arg Trp Asn Glu Lys
        180                 185                 190

Tyr Ala Gln Ala Tyr Pro Asn Val Ser Ala Lys Ile Asp Tyr Asp Asp
    195                 200                 205

Glu Met Ala Tyr Ser Glu Ser Gln Leu Ile Ala Lys Phe Gly Thr Ala
210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
            245                 250                 255

Asn Val Asn Val Asn Glu Pro Thr Arg Pro Ser Arg Phe Phe Gly Lys
        260                 265                 270

Ala Val Thr Lys Glu Gln Leu Gln Ala Leu Gly Val Asn Ala Glu Asn
    275                 280                 285

Pro Pro Ala Tyr Ile Ser Ser Val Ala Tyr Gly Arg Gln Val Tyr Leu
290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu

<210> SEQ ID NO 57
<211> LENGTH: 441
<212> TYPE: PRT
```

<213> ORGANISM: Listeria monocytogenes

<400> SEQUENCE: 57

| | | | | | | | | | | | | | | | |
|---|---|---|---|---|---|---|---|---|---|---|---|---|---|---|---|
| Met | Lys | Lys | Ile | Met | Leu | Val | Phe | Ile | Thr | Leu | Ile | Leu | Val | Ser | Leu |
| 1 | | | | 5 | | | | | 10 | | | | | 15 | |
| Pro | Ile | Ala | Gln | Gln | Thr | Glu | Ala | Lys | Asp | Ala | Ser | Ala | Phe | Asn | Lys |
| | | | 20 | | | | | 25 | | | | | 30 | | |
| Glu | Asn | Ser | Ile | Ser | Ser | Val | Ala | Pro | Pro | Ala | Ser | Pro | Pro | Ala | Ser |
| | | | 35 | | | | 40 | | | | | 45 | | | |
| Pro | Lys | Thr | Pro | Ile | Glu | Lys | Lys | His | Ala | Asp | Glu | Ile | Asp | Lys | Tyr |
| | 50 | | | | | 55 | | | | | 60 | | | | |
| Ile | Gln | Gly | Leu | Asp | Tyr | Asn | Lys | Asn | Asn | Val | Leu | Val | Tyr | His | Gly |
| 65 | | | | | 70 | | | | | 75 | | | | | 80 |
| Asp | Ala | Val | Thr | Asn | Val | Pro | Pro | Arg | Lys | Gly | Tyr | Lys | Asp | Gly | Asn |
| | | | | 85 | | | | | 90 | | | | | 95 | |
| Glu | Tyr | Ile | Val | Val | Glu | Lys | Lys | Lys | Ser | Ile | Asn | Gln | Asn | Asn | |
| | | | | 100 | | | | | 105 | | | | | 110 | |
| Ala | Asp | Ile | Gln | Val | Val | Asn | Ala | Ile | Ser | Ser | Leu | Thr | Tyr | Pro | Gly |
| | | | 115 | | | | | 120 | | | | | 125 | | |
| Ala | Leu | Val | Lys | Ala | Asn | Ser | Glu | Leu | Val | Glu | Asn | Gln | Pro | Asp | Val |
| | 130 | | | | | 135 | | | | | 140 | | | | |
| Leu | Pro | Val | Lys | Arg | Asp | Ser | Leu | Thr | Leu | Ser | Ile | Asp | Leu | Pro | Gly |
| 145 | | | | | 150 | | | | | 155 | | | | | 160 |
| Met | Thr | Asn | Gln | Asp | Asn | Lys | Ile | Val | Val | Lys | Asn | Ala | Thr | Lys | Ser |
| | | | | 165 | | | | | 170 | | | | | 175 | |
| Asn | Val | Asn | Asn | Ala | Val | Asn | Thr | Leu | Val | Glu | Arg | Trp | Asn | Glu | Lys |
| | | | 180 | | | | | 185 | | | | | 190 | | |
| Tyr | Ala | Gln | Ala | Tyr | Ser | Asn | Val | Ser | Ala | Lys | Ile | Asp | Tyr | Asp | Asp |
| | | | 195 | | | | | 200 | | | | | 205 | | |
| Glu | Met | Ala | Tyr | Ser | Glu | Ser | Gln | Leu | Ile | Ala | Lys | Phe | Gly | Thr | Ala |
| | 210 | | | | | 215 | | | | | 220 | | | | |
| Phe | Lys | Ala | Val | Asn | Asn | Ser | Leu | Asn | Val | Asn | Phe | Gly | Ala | Ile | Ser |
| 225 | | | | | 230 | | | | | 235 | | | | | 240 |
| Glu | Gly | Lys | Met | Gln | Glu | Glu | Val | Ile | Ser | Phe | Lys | Gln | Ile | Tyr | Tyr |
| | | | | 245 | | | | | 250 | | | | | 255 | |
| Asn | Val | Asn | Val | Asn | Glu | Pro | Thr | Arg | Pro | Ser | Arg | Phe | Phe | Gly | Lys |
| | | | 260 | | | | | 265 | | | | | 270 | | |
| Ala | Val | Thr | Lys | Glu | Gln | Leu | Gln | Ala | Leu | Gly | Val | Asn | Ala | Glu | Asn |
| | | | 275 | | | | | 280 | | | | | 285 | | |
| Pro | Pro | Ala | Tyr | Ile | Ser | Ser | Val | Ala | Tyr | Gly | Arg | Gln | Val | Tyr | Leu |
| | 290 | | | | | 295 | | | | | 300 | | | | |
| Lys | Leu | Ser | Thr | Asn | Ser | His | Ser | Thr | Lys | Val | Lys | Ala | Ala | Phe | Asp |
| 305 | | | | | 310 | | | | | 315 | | | | | 320 |
| Ala | Ala | Val | Ser | Gly | Lys | Ser | Val | Ser | Gly | Asp | Val | Glu | Leu | Thr | Asn |
| | | | | 325 | | | | | 330 | | | | | 335 | |
| Ile | Ile | Lys | Asn | Ser | Ser | Phe | Lys | Ala | Val | Ile | Tyr | Gly | Gly | Ser | Ala |
| | | | 340 | | | | | 345 | | | | | 350 | | |
| Lys | Asp | Glu | Val | Gln | Ile | Ile | Asp | Gly | Asn | Leu | Gly | Asp | Leu | Arg | Asp |
| | | | 355 | | | | | 360 | | | | | 365 | | |
| Ile | Leu | Lys | Lys | Gly | Ala | Thr | Phe | Asn | Arg | Glu | Thr | Pro | Gly | Val | Pro |
| | 370 | | | | | 375 | | | | | 380 | | | | |
| Ile | Ala | Tyr | Thr | Thr | Asn | Phe | Leu | Lys | Asp | Asn | Glu | Leu | Ala | Val | Ile |
| 385 | | | | | 390 | | | | | 395 | | | | | 400 |

```
Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp
        435                 440

<210> SEQ ID NO 58
<211> LENGTH: 416
<212> TYPE: PRT
<213> ORGANISM: Listeria monocytogenes

<400> SEQUENCE: 58

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Ala Ser Pro Ala Ser
        35                  40                  45

Pro Lys Thr Pro Ile Glu Lys Lys His Ala Asp Glu Ile Asp Lys Tyr
50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
            115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335
```

-continued

```
Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
            405                 410                 415

<210> SEQ ID NO 59
<211> LENGTH: 390
<212> TYPE: PRT
<213> ORGANISM: Listeria monocytogenes

<400> SEQUENCE: 59

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn Asn Ser Glu Gln Thr Glu Asn Ala Ala Ile Asn Glu
            100                 105                 110

Glu Ala Ser Gly Ala Asp Arg Pro Ala Ile Gln Val Glu Arg Arg His
        115                 120                 125

Pro Gly Leu Pro Ser Asp Ser Ala Ala Glu Ile Lys Lys Arg Arg Lys
    130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
            180                 185                 190

Ser Ser Pro Gln Pro Leu Lys Ala Asn Gln Gln Pro Phe Phe Pro Lys
        195                 200                 205

Val Phe Lys Lys Ile Lys Asp Ala Gly Lys Trp Val Arg Asp Lys Ile
    210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Pro Thr Asp Glu Glu Leu Arg
```

```
              290                 295                 300
Leu Ala Leu Pro Glu Thr Pro Met Leu Leu Gly Phe Asn Ala Pro Ala
305                 310                 315                 320

Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
            340                 345                 350

Thr Arg Gly Asp Leu Ala Ser Leu Arg Asn Ala Ile Asn Arg His Ser
                355                 360                 365

Gln Asn Phe Ser Asp Phe Pro Pro Ile Pro Thr Glu Glu Leu Asn
        370                 375                 380

Gly Arg Gly Gly Arg Pro
385                 390

<210> SEQ ID NO 60
<211> LENGTH: 100
<212> TYPE: PRT
<213> ORGANISM: Listeria monocytogenes

<400> SEQUENCE: 60

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Glu Lys Thr Glu Gln Pro Ser Glu
        35                  40                  45

Val Asn Thr Gly Pro Arg Tyr Glu Thr Ala Arg Glu Val Ser Ser Arg
    50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
                85                  90                  95

Ile Asn Asn Asn
            100

<210> SEQ ID NO 61
<211> LENGTH: 1170
<212> TYPE: DNA
<213> ORGANISM: Listeria monocytogenes

<400> SEQUENCE: 61
atgcgtgcga tgatggtggt tttcattact gccaattgca ttacgattaa ccccgacata    60
atatttgcag cgacagatag cgaagattct agtctaaaca cagatgaatg ggaagaagaa   120
aaaacagaag agcaaccaag cgaggtaaat acgggaccaa gatacgaaac tgcacgtgaa   180
gtaagttcac gtgatattaa agaactagaa aaatcgaata aagtgagaaa tacgaacaaa   240
gcagacctaa tagcaatgtt gaaagaaaaa gcagaaaaag gtccaaatat caataataac   300
aacagtgaac aaactgagaa tgcggctata aatgaagagg cttcaggagc cgaccgacca   360
gctatacaag tggagcgtcg tcatccagga ttgccatcgg atagcgcagc ggaaattaaa   420
aaaagaagga agccatagc atcatcggat agtgagcttg aaagccttac ttatccggat   480
aaaccaacaa aagtaaataa gaaaaagtg gcgaaagagt cagttgcgga tgcttctgaa   540
agtgacttag attctagcat gcagtcagca gatgagtctt caccacaacc tttaaaagca   600
aaccaacaac cattttttccc taagtatttt aaaaaaaata aagatgcggg gaatgggta   660
```

-continued

```
cgtgataaaa tcgacgaaaa tcctgaagta aagaaagcga ttgttgataa aagtgcaggg      720
ttaattgacc aattattaac caaaagaaa agtgaagagg taaatgcttc ggacttcccg       780
ccaccaccta cggatgaaga gttaagactt gctttgccag agacaccaat gcttcttggt     840
tttaatgctc ctgctacatc agaaccgagc tcattcgaat tccaccacc acctacggat      900 gaagagttaa acttgctttt gccagagacg ccaatgcttc ttggttttaa tgctcctgct     960
acatcggaac cgagctcgtt cgaatttcca ccgcctccaa cagaagatga actagaaatc    1020
atccgggaaa cagcatcctc gctagattct agtttacaa gagggatttt agctagtttg    1080
agaaatgcta ttaatcgcca tagtcaaaat ttctctgatt tcccaccaat cccaacagaa    1140
gaagagttga acgggagagg cggtagacca                                      1170
```

<210> SEQ ID NO 62
<211> LENGTH: 32
<212> TYPE: PRT
<213> ORGANISM: Listeria monocytogenes

<400> SEQUENCE: 62

Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30

<210> SEQ ID NO 63
<211> LENGTH: 19
<212> TYPE: PRT
<213> ORGANISM: Listeria monocytogenes

<400> SEQUENCE: 63

Lys Glu Asn Ser Ile Ser Ser Met Ala Pro Pro Ala Ser Pro Pro Ala
1               5                   10                  15

Ser Pro Lys

<210> SEQ ID NO 64
<211> LENGTH: 14
<212> TYPE: PRT
<213> ORGANISM: Listeria monocytogenes

<400> SEQUENCE: 64

Lys Thr Glu Glu Gln Pro Ser Glu Val Asn Thr Gly Pro Arg
1               5                   10

<210> SEQ ID NO 65
<211> LENGTH: 28
<212> TYPE: PRT
<213> ORGANISM: Listeria monocytogenes

<400> SEQUENCE: 65

Lys Ala Ser Val Thr Asp Thr Ser Glu Gly Asp Leu Asp Ser Ser Met
1               5                   10                  15

Gln Ser Ala Asp Glu Ser Thr Pro Gln Pro Leu Lys
            20                  25

<210> SEQ ID NO 66
<211> LENGTH: 20
<212> TYPE: PRT
<213> ORGANISM: Listeria monocytogenes

<400> SEQUENCE: 66

Lys Asn Glu Glu Val Asn Ala Ser Asp Phe Pro Pro Pro Pro Thr Asp

-continued

```
                1               5                  10                 15
Glu Glu Leu Arg
            20

<210> SEQ ID NO 67
<211> LENGTH: 33
<212> TYPE: PRT
<213> ORGANISM: Listeria monocytogenes

<400> SEQUENCE: 67

Arg Gly Gly Ile Pro Thr Ser Glu Glu Phe Ser Ser Leu Asn Ser Gly
1               5                  10                 15

Asp Phe Thr Asp Asp Glu Asn Ser Glu Thr Thr Glu Glu Glu Ile Asp
            20                  25                  30

Arg

<210> SEQ ID NO 68
<211> LENGTH: 19
<212> TYPE: PRT
<213> ORGANISM: Listeria seeligeri

<400> SEQUENCE: 68

Arg Ser Glu Val Thr Ile Ser Pro Ala Glu Thr Pro Glu Ser Pro Pro
1               5                  10                 15

Ala Thr Pro

<210> SEQ ID NO 69
<211> LENGTH: 17
<212> TYPE: PRT
<213> ORGANISM: Streptococcus sp.

<400> SEQUENCE: 69

Lys Gln Asn Thr Ala Ser Thr Glu Thr Thr Thr Thr Asn Glu Gln Pro
1               5                  10                 15

Lys

<210> SEQ ID NO 70
<211> LENGTH: 17
<212> TYPE: PRT
<213> ORGANISM: Streptococcus equisimilis

<400> SEQUENCE: 70

Lys Gln Asn Thr Ala Asn Thr Glu Thr Thr Thr Thr Asn Glu Gln Pro
1               5                  10                 15

Lys

<210> SEQ ID NO 71
<211> LENGTH: 29
<212> TYPE: DNA
<213> ORGANISM: Artificial
<220> FEATURE:
<223> OTHER INFORMATION: Primer

<400> SEQUENCE: 71
gaagatctcc aaaaataaac aggtggtgg                                    29
```